(12) United States Patent
Hebeisen et al.

(10) Patent No.: US 8,729,105 B2
(45) Date of Patent: May 20, 2014

(54) HETEROARYLMETHYL AMIDES

(75) Inventors: Paul Hebeisen, Basel (CH); Hugues Matile, Basel (CH); Stephan Roever, Inzlingen (DE); Matthew Wright, Basel (CH); Sannah Zoffmann Jensen, Basel (CH)

(73) Assignee: Hoffmann La-Roche Inc., Nutley, NJ (US)

( * ) Notice: Subject to any disclaimer, the term of this patent is extended or adjusted under 35 U.S.C. 154(b) by 2 days.

(21) Appl. No.: 13/226,521

(22) Filed: Sep. 7, 2011

(65) Prior Publication Data

US 2012/0065212 A1 Mar. 15, 2012

(30) Foreign Application Priority Data

Sep. 9, 2010 (EP) ..................... 10175984

(51) Int. Cl.
*C07D 413/12* (2006.01)
*A61K 31/4418* (2006.01)

(52) U.S. Cl.
USPC ........ 514/340; 514/341; 514/342; 546/272.1; 546/283.4; 546/280.4

(58) Field of Classification Search
USPC ......... 546/272.1, 283.4, 280.4; 514/341, 342, 514/340
See application file for complete search history.

(56) References Cited

U.S. PATENT DOCUMENTS 7,897,621 B2 * 3/2011 Hebeisen et al. ............. 514/335
2012/0157476 A1 * 6/2012 Hebeisen et al. ........ 514/255.06

FOREIGN PATENT DOCUMENTS

| WO | 03/051850 | 6/2003 |
|---|---|---|
| WO | 2006/106054 | 10/2006 |
| WO | 2007/147746 | 12/2007 |
| WO | 2008/040649 | 4/2008 |
| WO | 2008/040651 | 4/2008 |
| WO | 2009/121740 | 10/2009 |
| WO | 2009/121741 | 10/2009 |
| WO | 2010/051188 | 5/2010 |
| WO | 2011/029827 | 3/2011 |

OTHER PUBLICATIONS

"International Search Report PCT/EP2011/065341 mailed Nov. 28, 2011".

* cited by examiner

*Primary Examiner* — Emily Bernhardt
*Assistant Examiner* — Cecilia M Jaisle

(57) ABSTRACT

The present invention relates to compounds of the formula wherein $A^1$, $A^2$, $A^3$ and $R^1$ to $R^8$ are defined in the description, and to pharmaceutically acceptable salts thereof, their manufacture, pharmaceutical compositions containing them and their use as medicaments for the treatment and/or prophylaxis of diseases which can be treated with HDL-cholesterol raising agents, such as particularly dyslipidemia, atherosclerosis and cardiovascular diseases.

9 Claims, No Drawings

HETEROARYLMETHYL AMIDES

PRIORITY TO RELATED APPLICATIONS

This application claims the benefit of European Patent Application No. 10175984.3, filed Sep. 9, 2010, which is hereby incorporated by reference in its entirety.

FIELD OF THE INVENTION

The present invention is concerned with heteroarylmethyl amide compounds as HDL-cholesterol raising agents, their manufacture, pharmaceutical compositions containing them and their use as therapeutically active substances. The compounds of the present invention can be used in the therapeutic and/or prophylactic treatment of diseases and disorders such as dyslipidemia, atherosclerosis and cardiovascular diseases.

BACKGROUND OF THE INVENTION

Atherosclerosis and its associated coronary heart disease are the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are 3 different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well tolerated agent which can significantly elevate plasma HDL levels.

Thus, HDL-cholesterol raising agents can be useful as medicaments for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, HDL-cholesterol raising agents may be used in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesteryl ester transfer protein (CETP) inhibitor, a cholesterol absorption inhibitor, a cholesterol synthesis inhibitor, a fibrate, niacin, preparations containing niacin or other HM74a agonists, an ion-exchange resin, an antioxidant, an ACAT inhibitor or a bile acid sequestrant.

It has been found that the compounds of the present invention are useful for the treatment and/or prophylaxis of diseases and disorders which can be treated with HDL-cholesterol raising agents, i.e. the compounds are especially useful for the treatment and/or prevention of dyslipidemia, atherosclerosis and cardiovascular diseases.

SUMMARY OF THE INVENTION

The present invention relates to a compound of formula I,

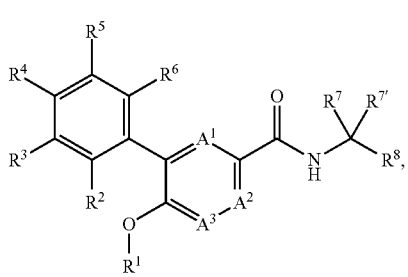

wherein
$A^1$, $A^2$ and $A^3$ are each selected from N and CH, provided that at least one of $A^1$, $A^2$ and $A^3$ is N and at least one of $A^1$, $A^2$ and $A^3$ is CH;
$R^1$ is selected from the group consisting of lower alkyl,
cycloalkyl,
lower cycloalkylalkyl,
lower hydroxyalkyl,
lower alkoxyalkyl,
lower halogenalkyl,
lower carbamoylalkyl,
lower alkylcarbonylaminoalkyl,
lower phenylalkyl,
lower heterocyclylalkyl wherein the heterocyclyl group is unsubstituted or substituted by oxo,
lower heteroarylalkyl wherein the heteroaryl group is unsubstituted or mono- or di-substituted by lower alkyl, and
phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkoxy, halogen, lower halogenalkyl, lower halogenalkoxy and cyano;
or $R^4$ and $R^5$ together with the C atoms they are attached to form a five- or six-membered carbocycle or a five- or six-membered heterocycle containing one, two or three heteroatoms selected from the group consisting of N, O and S, said carbocycle or heterocycle being unsubstituted or substituted by one or two substituents independently selected from the group consisting of lower alkyl, lower alkoxy, halogen, lower halogenalkyl, lower halogenalkoxy and cyano;
$R^7$ and $R^{7'}$ independently from each other are hydrogen or lower alkyl; and
$R^8$ is a five- or six-membered heteroaryl group containing one, two or three heteroatoms selected from the group consisting of N, O and S, said heteroaryl group being unsubstituted or substituted by one or two substituents independently selected from the group consisting of lower alkyl, lower alkoxy, halogen, lower halogenalkyl and cycloalkyl;
or a pharmaceutically acceptable salt thereof.

The present invention also relates to a pharmaceutical composition comprising a compound as described above and a pharmaceutically acceptable carrier and/or adjuvant.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "alkyl", alone or in combination with other groups, refers to a branched or straight-chain monovalent saturated aliphatic hydrocarbon radical of one to twenty carbon atoms, preferably one to sixteen carbon atoms, in particular one to ten carbon atoms.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular ethyl, propyl, isopropyl and tert-butyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, in particular methoxy.

The term "lower alkoxyalkyl" or "$C_{1-7}$-alkoxy-$C_{1-7}$-alkyl" refers to a lower alkyl group as defined above which is mono- or multiply substituted with a lower alkoxy group as defined above. Examples of lower alkoxyalkyl groups are e.g. —$CH_2$—O—$CH_3$, —$CH_2$—$CH_2$—O—$CH_3$, —$CH_2$—O—$CH_2$—$CH_3$ and the groups specifically exemplified herein. More particularly, lower alkoxyalkyl is methoxyethyl.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Of particular interest are $C_{3-7}$-hydroxyalkyl groups. Examples of lower hydroxyalkyl groups are 2-hydroxybutyl, 3-hydroxy-2,2-dimethylpropyl and the groups specifically exemplified therein.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl, more particularly cyclopropyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by a cycloalkyl group. Among the lower cycloalkylalkyl groups of particular interest resides cyclopropylmethyl.

The term "halogen" refers to fluoro, chloro, bromo and iodo, with fluoro, chloro and bromo being of particular interest. More particularly, halogen refers to fluoro and chloro.

The term "lower halogenalkyl" or "halogen-$C_{1-7}$-alkyl" refers to lower alkyl groups which are mono- or multiply substituted with halogen, preferably with fluoro or chloro, most preferably with fluoro. Examples of lower halogenalkyl groups are e.g. —$CF_3$, —$CHF_2$, —$CH_2Cl$, —$CH_2CF_3$, —$CH(CF_3)_2$, —$CF_2$—$CF_3$, —$CH(CH_3)$—$CF_3$ and the groups specifically exemplified herein. Of particular interest are the groups trifluoromethyl (—$CF_3$), 2,2,2-trifluoroethyl (—$CH_2CF_3$) and 1,1,1-trifluoro-propan-2-yl (—$CH(CH_3)$—$CF_3$).

The term "carbamoyl" refers to the group —CO—$NH_2$.

The term "lower carbamoylalkyl" or "carbamoyl-$C_{1-7}$-alkyl" refers to lower alkyl groups as defined above wherein one of the hydrogen atoms of the lower alkyl group is replaced by a carbamoyl group. Examples of lower carbamoylalkyl groups are 3-carbamoylpropyl, 4-carbamoylbutyl and 5-carbamoylpentyl, more particularly 4-carbamoylbutyl.

The term "lower alkylcarbonyl" refers to the group —CO—R", wherein R" is lower alkyl as defined herein before. "Lower alkylcarbonylamino" refers to the group —NH—CO—R", wherein R" is lower alkyl as defined herein before.

The term "lower alkylcarbonylaminoalkyl" or "$C_{1-7}$-alkylcarbonylamino-$C_{1-7}$-alkyl" refers to lower alkyl groups as defined above wherein one of the hydrogen atoms of the lower alkyl group is replaced by a lower alkylcarbonylamino group. An example for a lower alkylcarbonylaminoalkyl group is ethylcarbonylaminoethyl.

The term "lower phenylalkyl" or "phenyl-$C_{1-7}$-alkyl" refers to lower alkyl groups as defined above wherein at least one of the hydrogen atoms of the lower alkyl group is replaced by a phenyl group. In particular, lower phenylalkyl means benzyl.

The term "heterocyclyl" refers to a saturated or partly unsaturated 3-, 4-, 5-, 6- or 7-membered ring which can comprise one, two or three heteroatoms selected from N, O and S. Examples of heterocyclyl rings include piperidinyl, piperazinyl, azetidinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, oxiranyl, thiadiazolylidinyl, oxetanyl, dioxolanyl, dihydrofuryl, tetrahydrofuryl, dihydropyranyl, tetrahydropyranyl, and thiomorpholinyl.

The term "lower heterocyclylalkyl" or "heterocyclyl-$C_{1-7}$-alkyl" refers to lower alkyl groups as defined above wherein at least one of the hydrogen atoms of the lower alkyl group is replaced by a heterocyclyl group as defined above.

The term "heteroaryl" refers to an aromatic 5- or 6-membered ring which can comprise one, two or three atoms selected from N, O and S. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, pyrazolyl, triazolyl, oxadiazolyl, oxatriazolyl, tetrazolyl, pentazolyl, or pyrrolyl. The heteroaryl group can optionally be mono- or disubstituted by lower alkyl, lower alkoxy, halogen, lower halogenalkyl or cycloalkyl. Heteroaryl groups of particular interest are oxazolyl, isoxazolyl, pyrazolyl, thiazolyl and [1,2,4]oxadiazolyl.

The term "lower heteroarylalkyl" or "heteroaryl-$C_{1-7}$-alkyl" refers to lower alkyl groups as defined above wherein at least one of the hydrogen atoms of the lower alkyl group is replaced by a heteroaryl group as defined above.

The term "carbocycle" refers to non-aromatic or aromatic ring system in which all ring atoms are carbon atoms. Carbocycles are cycloalkyl groups, but also aromatic groups such as phenyl.

The term "heterocycle" refers to heterocyclyl and heteroaryl groups as defined herein before.

"Isomeric forms" are all forms of a compound characterized by having an identical molecular formula but that differ in the nature or the sequence of bonding of their atoms or in the arrangement of their atoms in space. Preferably, the isomeric forms differ in the arrangement of their atoms in space and can also be termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

The term "pharmaceutically acceptable salts" refers to those salts which retain the biological effectiveness and properties of the free bases or free acids, and which do not possess any own properties that are undesirable. The salts are formed with inorganic acids such as hydrochloric acid, hydrobromic acid, sulfuric acid, nitric acid, phosphoric acid and the like, preferably hydrochloric acid, and organic acids such as formic acid, acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. Thus, preferred "pharmaceutically acceptable salts" include the acetate, bromide, chloride, formate, fumarate, maleate, mesylate, nitrate, oxalate, phosphate, sulfate, tartrate and tosylate salt of compounds of formula I. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, diethylamine, lysine, arginine, N-ethylpiperidine, piperidine, piperazine and the like. The compound of formula I can also be present in the form of zwitterions or in the form of hydrates. Particularly preferred pharmaceutically acceptable salts of compounds of formula I are the hydrochloride salts.

The present invention relates to compounds of formula I,

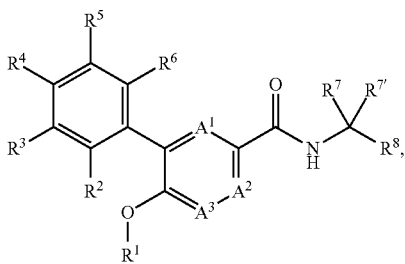

wherein
$A^1$, $A^2$ and $A^3$ are each selected from N and CH, provided that at least one of $A^1$, $A^2$ and $A^3$ is N and at least one of $A^1$, $A^2$ and $A^3$ is CH;
$R^1$ is selected from the group consisting of lower alkyl,
cycloalkyl,
lower cycloalkylalkyl,
lower hydroxyalkyl,
lower alkoxyalkyl,
lower halogenalkyl,
lower carbamoylalkyl,
lower alkylcarbonylaminoalkyl,
lower phenylalkyl,
lower heterocyclylalkyl wherein the heterocyclyl group is unsubstituted or substituted by oxo,
lower heteroarylalkyl wherein the heteroaryl group is unsubstituted or mono- or di-substituted by lower alkyl, and
phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkoxy, halogen, lower halogenalkyl, lower halogenalkoxy and cyano;
or $R^4$ and $R^5$ together with the C atoms they are attached to form a five- or six-membered carbocycle or a five- or six-membered heterocycle containing one, two or three heteroatoms selected from the group consisting of N, O and S, said carbocycle or heterocycle being unsubstituted or substituted by one or two substituents independently selected from the group consisting of lower alkyl, lower alkoxy, halogen, lower halogenalkyl, lower halogenalkoxy and cyano;
$R^7$ and $R^{7'}$ independently from each other are hydrogen or lower alkyl; and
$R^8$ is a five- or six-membered heteroaryl group containing one, two or three heteroatoms selected from the group consisting of N, O and S, said heteroaryl group being unsubstituted or substituted by one or two substituents independently selected from the group consisting of lower alkyl, lower alkoxy, halogen, lower halogenalkyl and cycloalkyl;
and pharmaceutically acceptable salts thereof.

In particular, compounds of the present invention are those according to formula I, wherein
$A^1$, $A^2$ and $A^3$ are each selected from N and CH, provided that at least one of $A^1$, $A^2$ or $A^3$ is N and at least one of $A^1$, $A^2$ or $A^3$ is CH;
$R^1$ is selected from the group consisting of
lower alkyl,
cycloalkyl,
lower cycloalkylalkyl,
lower hydroxyalkyl,
lower alkoxyalkyl,
lower halogenalkyl,
lower carbamoylalkyl,
lower alkylcarbonylaminoalkyl,
lower phenylalkyl,
lower heterocyclylalkyl wherein the heterocyclyl group is unsubstituted or substituted by oxo,
lower heteroarylalkyl wherein the heteroaryl group is unsubstituted or mono- or di-substituted by lower alkyl, and
phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkoxy, halogen, lower halogenalkyl, lower halogenalkoxy and cyano;
$R^7$ and $R^{7'}$ independently from each other are hydrogen or lower alkyl; and
$R^8$ is a five- or six-membered heteroaryl group containing one, two or three heteroatoms selected from the group consisting of N, O and S, said heteroaryl group being unsubstituted or substituted by one or two substituents independently selected from the group consisting of lower alkyl, lower alkoxy, halogen, lower halogenalkyl and cycloalkyl;
and pharmaceutically acceptable salts thereof.

One group of compounds according to the invention are those of formula I, wherein one of $A^1$, $A^2$ or $A^3$ is N and two of $A^1$, $A^2$ or $A^3$ are CH.

Thus, the invention relates to pyridine compounds of formula I, wherein $A^1$ is N and $A^2$ and $A^3$ are CH. A further group of compounds of the present invention are pyridine compounds of formula I, wherein $A^2$ is N and $A^1$ and $A^3$ are CH. The invention is also concerned with pyridine compounds of formula I, wherein $A^3$ is N and $A^1$ and $A^2$ are CH.

Another group of compounds of the present invention are those of formula I, wherein two of $A^1$, $A^2$ or $A^3$ are N and one of $A^1$, $A^2$ or $A^3$ is CH.

The invention thus also relates to compounds of formula I, wherein $A^1$ and $A^2$ are N and $A^3$ is CH, i.e. to pyrimidine compounds of formula I.

A further group of compounds of the invention are those of formula I, wherein $A^2$ and $A^3$ are N and $A^1$ is CH, i.e. to pyridazine compounds of formula I.

In addition, the invention relates to compounds of formula I, wherein $A^1$ and $A^3$ are N and $A^2$ is CH, i.e. to pyrazine compounds of formula I.

The invention relates to compounds of formula I, wherein $R^1$ is selected from the group consisting of lower alkyl, cycloalkyl, lower cycloalkylalkyl, lower hydroxyalkyl, lower alkoxyalkyl, lower halogenalkyl, lower carbamoylalkyl, lower alkylcarbonylaminoalkyl, lower phenylalkyl, lower heterocyclylalkyl wherein the heterocyclyl group is unsubstituted or substituted by oxo, lower heteroarylalkyl wherein the heteroaryl group is unsubstituted or mono- or di-substituted by lower alkyl, and phenyl which is unsubstituted or mono- or di-substituted by halogen.

In particular, the invention relates to compounds of formula I, wherein $R^1$ is lower cycloalkylalkyl or lower halogenalkyl. More particularly, $R^1$ is cyclopropylmethyl or lower halogenalkyl. Most particularly, $R^1$ is selected from the group consisting of cyclopropylmethyl, 2,2,2-trifluoroethyl and 1,1,1-trifluoropropan-2-yl.

Compounds of formula I of the invention are those, wherein $R^2$ and $R^6$ are independently from each other hydrogen or halogen. Compounds of formula I, wherein $R^2$ and $R^6$ are hydrogen, are of particular interest.

The invention further relates to compounds of formula I, wherein $R^3$ and $R^5$ are independently from each other selected from the group consisting of hydrogen, lower alkyl, lower alkoxy, halogen, lower halogenalkyl, lower halogenalkoxy and cyano. In particular, the invention relates to compounds of formula I, wherein $R^3$ and $R^5$ are hydrogen.

Furthermore, the invention is concerned with compounds of formula I, wherein $R^4$ is selected from the group consisting of hydrogen, lower alkoxy, halogen, lower halogenalkyl, lower halogenalkoxy and cyano. More particularly, $R^4$ is halogen. Most particularly, $R^4$ is chloro.

The invention also relates to compounds of formula I, wherein $R^4$ and $R^5$ together with the C atoms they are attached to form a five- or six-membered carbocycle or a five- or six-membered heterocycle containing one, two or three heteroatoms selected from the group consisting of N, O and S, said carbocycle or heterocycle being unsubstituted or substituted by one or two substituents independently selected from the group consisting of lower alkyl, lower alkoxy, halogen, lower halogenalkyl, lower halogenalkoxy and cyano. In particular, the invention relates to compounds of formula I, wherein $R^4$ and $R^5$ together with the C atoms they are attached to form a five- or six-membered carbocycle, more particularly a cycloalkyl ring such as cyclopentyl or cylohexyl. More particularly, the invention relates to compounds of formula I wherein $R^4$ and $R^5$ together with the C atoms they are attached to form a five- or six-membered heterocycle containing one, two or three heteroatoms selected from the group consisting of N, O and S, for example a [1,2,5]oxadiazolyl ring.

Compounds of formula I of the invention are further those, wherein $R^7$ and $R^{7'}$ independently from each other are hydrogen or lower alkyl. More particularly, $R^7$ and $R^{7'}$ are hydrogen.

In addition, compounds of formula I of the present invention are those, wherein $R^8$ is a five- or six-membered heteroaryl group containing one, two or three heteroatoms selected from the group consisting of N, O and S, said heteroaryl group being unsubstituted or substituted by one or two substituents independently selected from the group consisting of lower alkyl, lower alkoxy, halogen, lower halogenalkyl and cycloalkyl. In particular, the invention relates to compounds of formula I, wherein $R^8$ is a five-membered heteroaryl group containing one, two or three heteroatoms selected from the group consisting of N, O and S, said heteroaryl group being unsubstituted or substituted by one or two substituents independently selected from the group consisting of lower alkyl, lower alkoxy, halogen, lower halogenalkyl and cycloalkyl.

More particularly, the invention relates to compounds of formula I, wherein $R^8$ is a five-membered heteroaryl group is selected from the group consisting of oxazolyl, isoxazolyl, pyrazolyl, thiazolyl and [1,2,4]oxadiazolyl, said heteroaryl group being unsubstituted or substituted by one or two substituents independently selected from the group consisting of lower alkyl, lower alkoxy, halogen, lower halogenalkyl and cycloalkyl. Most particularly, $R^8$ is a five-membered heteroaryl group selected from oxazolyl, isoxazolyl and [1,2,4]oxadiazolyl, said heteroaryl group being unsubstituted or substituted by one or two substituents independently selected from the group consisting of lower alkyl, lower alkoxy, halogen, lower halogenalkyl and cycloalkyl.

Particular compounds of formula I of the present invention are the following:

4-(4-chloro-phenyl)-5-(2,2,2-trifluoro-ethoxy)-pyridine-2-carboxylic acid (3-methoxy-isoxazol-5-ylmethyl)-amide, 4-(4-chloro-phenyl)-5-(2,2,2-trifluoro-ethoxy)-pyridine-2-carboxylic acid (3-isopropyl-isoxazol-5-ylmethyl)-amide, 4-(4-chloro-phenyl)-5-(2,2,2-trifluoro-ethoxy)-pyridine-2-carboxylic acid (3-ethyl-isoxazol-5-ylmethyl)-amide, 4-(4-chloro-phenyl)-5-(2,2,2-trifluoro-ethoxy)-pyridine-2-carboxylic acid (1-propyl-1H-pyrazol-3-ylmethyl)-amide, 5-(4-chloro-phenyl)-N-(3-methoxy-isoxazol-5-ylmethyl)-6-(2,2,2-trifluoro-ethoxy)-nicotinamide, 4-(4-chloro-phenyl)-5-(2,2,2-trifluoro-ethoxy)-pyridine-2-carboxylic acid (2-isopropyl-thiazol-4-ylmethyl)-amide, 5-(4-chloro-phenyl)-N-(2-ethyl-thiazol-4-ylmethyl)-6-(2,2,2-trifluoro-ethoxy)-nicotinamide, 5-(4-chloro-phenyl)-N-(2-isopropyl-thiazol-4-ylmethyl)-6-(2,2,2-trifluoro-ethoxy)-nicotinamide, 5-(4-chloro-phenyl)-N-(2-propyl-thiazol-4-ylmethyl)-6-(2,2,2-trifluoro-ethoxy)-nicotinamide, 5-(4-chloro-phenyl)-6-cyclopropylmethoxy-N-(2-ethyl-thiazol-4-ylmethyl)-nicotinamide, 5-(4-chloro-phenyl)-6-cyclopropylmethoxy-N-(2-propyl-thiazol-4-ylmethyl)-nicotinamide, 5-(4-chloro-phenyl)-6-(2,2,2-trifluoro-ethoxy)-N-(5-trifluoromethyl-[1,2,4]oxadiazol-3-ylmethyl)-nicotinamide, 4-(4-chloro-phenyl)-5-cyclopropylmethoxy-pyrimidine-2-carboxylic acid (5-cyclopropyl-[1,2,4]oxadiazol-3-ylmethyl)-amide, 5-(4-chloro-phenyl)-N-(1-propyl-1H-pyrazol-3-ylmethyl)-6-(2,2,2-trifluoro-ethoxy)-nicotinamide, 5-(4-chloro-phenyl)-6-(2,2,2-trifluoro-ethoxy)-N-(3-trifluoromethyl-[1,2,4]oxadiazol-5-ylmethyl)-nicotinamide, 4-(4-chloro-phenyl)-5-(2,2,2-trifluoro-ethoxy)-pyrimidine-2-carboxylic acid (3-trifluoromethyl-[1,2,4]oxadiazol-5-ylmethyl)-amide,
4-(4-chloro-phenyl)-5-cyclopropylmethoxy-pyrimidine-2-carboxylic acid (3-cyclopropyl-[1,2,4]oxadiazol-5-ylmethyl)-amide,
4-(4-chlorophenyl)-5-(cyclopropylmethoxy)-N-((3-(trifluoromethyl)-1,2,4-oxadiazol-5-yl)methyl)picolinamide,
4-(4-chlorophenyl)-N-((5-methylisoxazol-3-yl)methyl)-5-(2,2,2-trifluoroethoxy)picolinamide,
5-(4-chloro-phenyl)-6-cyclopropylmethoxy-pyridazine-3-carboxylic acid (3-trifluoromethyl-[1,2,4]oxadiazol-5-ylmethyl)-amide,
4-(4-chloro-phenyl)-5-cyclopropylmethoxy-pyrimidine-2-carboxylic acid (3-trifluoromethyl-[1,2,4]oxadiazol-5-ylmethyl)-amide,
6-(4-chloro-phenyl)-5-(2,2,2-trifluoro-ethoxy)-pyridine-2-carboxylic acid (3-trifluoromethyl-[1,2,4]oxadiazol-5-ylmethyl)-amide.
5-(4-chlorophenyl)-N-((3-methoxyisoxazol-5-yl)methyl)-6-(2,2,2-trifluoroethoxy)pyridazine-3-carboxamide,
(S)-5-(4-chlorophenyl)-N-((3-methoxyisoxazol-5-yl)methyl)-6-(1,1,1-trifluoropropan-2-yloxy)pyridazine-3-carboxamide,
4-(3,4-dichlorophenyl)-N-((3-methoxyisoxazol-5-yl)methyl)-5-(2,2,2-trifluoroethoxy)pyrimidine-2-carboxamide,
N-(4-chloro-1-methyl-1H-pyrazol-3-ylmethyl)-5-(4-chlorophenyl)-6-(2,2,2-trifluoro-ethoxy)-nicotinamide,
4-(4-chlorophenyl)-N-((5-isopropylisoxazol-3-yl)methyl)-5-(2,2,2-trifluoroethoxy)picolinamide,
4-(4-chlorophenyl)-N-((5-cyclopropylisoxazol-3-yl)methyl)-5-(2,2,2-trifluoroethoxy)picolinamide,
(S)-6-(4-chlorophenyl)-N-((3-methoxyisoxazol-5-yl)methyl)-5-(1,1,1-trifluoropropan-2-yloxy)pyrazine-2-carboxamide,
5-(4-chloro-phenyl)-N-(5-cyclopropyl-isoxazol-3-ylmethyl)-6-cyclopropylmethoxy-nicotinamide,
5-(4-chlorophenyl)-N-((5-isopropylisoxazol-3-yl)methyl)-6-(2,2,2-trifluoroethoxy)nicotinamide,
5-(4-chlorophenyl)-6-(cyclopropylmethoxy)-N-((5-isopropylisoxazol-3-yl)methyl)nicotinamide,
4-(4-chlorophenyl)-N-((3-cyclopropylisoxazol-5-yl)methyl)-5-(2,2,2-trifluoroethoxy)picolinamide,
(S)-5-(4-chlorophenyl)-N-((3-methoxyisoxazol-5-yl)methyl)-6-(1,1,1-trifluoropropan-2-yloxy)nicotinamide,
(S)-4-(4-chlorophenyl)-N-((3-(trifluoromethyl)-1,2,4-oxadiazol-5-yl)methyl)-5-(1,1,1-trifluoropropan-2-yloxy)pyrimidine-2-carboxamide,
(S)-6-(4-chlorophenyl)-N-((3-(trifluoromethyl)-1,2,4-oxadiazol-5-yl)methyl)-5-(1,1,1-trifluoropropan-2-yloxy)pyrazine-2-carboxamide,
(S)-4-(4-chlorophenyl)-N-((3-methoxyisoxazol-5-yl)methyl)-5-(1,1,1-trifluoropropan-2-yloxy)picolinamide,
(S)-5-(4-chlorophenyl)-N-((3-(trifluoromethyl)-1,2,4-oxadiazol-5-yl)methyl)-6-(1,1,1-trifluoropropan-2-yloxy)nicotinamide,
4-(4-chlorophenyl)-N-((5-isopropyl-1,2,4-oxadiazol-3-yl)methyl)-5-(2,2,2-trifluoroethoxy)picolinamide,
4-(4-chlorophenyl)-N-((3-isopropyl-1,2,4-oxadiazol-5-yl)methyl)-5-(2,2,2-trifluoroethoxy)picolinamide,
5-(4-chloro-phenyl)-6-(2,2,2-trifluoro-ethoxy)-pyridazine-3-carboxylic acid (5-cyclopropyl-[1,2,4]oxadiazol-3-ylmethyl)-amide,
5-(4-chloro-phenyl)-6-(2,2,2-trifluoro-ethoxy)-pyridazine-3-carboxylic acid (5-isopropyl-isoxazol-3-ylmethyl)-amide,
5-(4-chloro-phenyl)-6-(2,2,2-trifluoro-ethoxy)-pyridazine-3-carboxylic acid (3-isopropyl-isoxazol-5-ylmethyl)-amide,
4-(4-chloro-phenyl)-5-(2,2,2-trifluoro-ethoxy)-pyrimidine-2-carboxylic acid (3-isopropyl-isoxazol-5-ylmethyl)-amide,
4-(4-chlorophenyl)-5-(2,2,2-trifluoroethoxy)-N-((5-(trifluoromethyl)isoxazol-3-yl)methyl)picolinamide,
5-(4-chloro-phenyl)-6-(2,2,2-trifluoro-ethoxy)-pyridazine-3-carboxylic acid (3-trifluoromethyl-[1,2,4]oxadiazol-5-ylmethyl)-amide,
6-(4-chloro-phenyl)-5-(2,2,2-trifluoro-ethoxy)-pyridine-2-carboxylic acid (3-cyclopropyl-isoxazol-5-ylmethyl)-amide,
5-(4-chloro-phenyl)-6-(2,2,2-trifluoro-ethoxy)-pyridazine-3-carboxylic acid (3-cyclopropyl-[1,2,4]oxadiazol-5-ylmethyl)-amide,
5-(4-chloro-phenyl)-6-(2,2,2-trifluoro-ethoxy)-pyridazine-3-carboxylic acid (3-cyclopropyl-isoxazol-5-ylmethyl)-amide,
5-(4-chloro-phenyl)-6-(2,2,2-trifluoro-ethoxy)-N-(5-trifluoromethyl-isoxazol-3-ylmethyl)-nicotinamide,
5-(4-chloro-phenyl)-6-cyclopropylmethoxy-N-(5-isopropyl-[1,2,4]oxadiazol-3-ylmethyl)-nicotinamide,
6-(4-chloro-phenyl)-5-cyclopropylmethoxy-pyridine-2-carboxylic acid (2-isopropyl-thiazol-4-ylmethyl)-amide,
6-(4-chloro-phenyl)-5-(2,2,2-trifluoro-ethoxy)-pyridine-2-carboxylic acid (5-isopropyl-isoxazol-3-ylmethyl)-amide,
N-((2-tert-butylthiazol-4-yl)methyl)-4-(4-chlorophenyl)-5-(cyclopropylmethoxy)picolinamide,
6-(4-chloro-phenyl)-5-cyclopropylmethoxy-pyridine-2-carboxylic acid (5-isopropyl-isoxazol-3-ylmethyl)-amide,
6-(4-chloro-phenyl)-5-cyclopropylmethoxy-pyridine-2-carboxylic acid (2-cyclopropyl-oxazol-4-ylmethyl)-amide,
6-(4-chloro-phenyl)-5-cyclopropylmethoxy-pyridine-2-carboxylic acid (2-cyclopropyl-thiazol-4-ylmethyl)-amide,
6-(4-chloro-phenyl)-5-cyclopropylmethoxy-pyridine-2-carboxylic acid (5-trifluoromethyl-isoxazol-3-ylmethyl)-amide,
5-(4-chloro-phenyl)-6-(2,2,2-trifluoro-ethoxy)-N-(3-trifluoromethyl-isoxazol-5-ylmethyl)-nicotinamide,
5-(4-chloro-phenyl)-6-(2,2,2-trifluoro-ethoxy)-pyridazine-3-carboxylic acid (3-trifluoromethyl-isoxazol-5-ylmethyl)-amide,
4-(4-chloro-phenyl)-5-(2,2,2-trifluoro-ethoxy)-pyrimidine-2-carboxylic acid (3-trifluoromethyl-isoxazol-5-ylmethyl)-amide,
4-(4-chloro-phenyl)-5-cyclopropylmethoxy-pyrimidine-2-carboxylic acid (3-trifluoromethyl-isoxazol-5-ylmethyl)-amide,
6-(4-chloro-phenyl)-5-cyclopropylmethoxy-pyridine-2-carboxylic acid (2-tert-butyl-thiazol-4-ylmethyl)-amide,
6-(4-chloro-phenyl)-5-(2,2,2-trifluoro-ethoxy)-pyridine-2-carboxylic acid (3-isopropyl-isoxazol-5-ylmethyl)-amide,
5-(4-chloro-phenyl)-6-(2,2,2-trifluoro-ethoxy)-pyridazine-3-carboxylic acid (2-tert-butyl-thiazol-4-ylmethyl)-amide,
5-(4-chloro-phenyl)-6-cyclopropylmethoxy-N-(5-trifluoromethyl-isoxazol-3-ylmethyl)-nicotinamide,
5-(4-chloro-phenyl)-6-(2,2,2-trifluoro-ethoxy)-pyridazine-3-carboxylic acid (5-trifluoromethyl-isoxazol-3-ylmethyl)-amide,
(S)-4-(4-chlorophenyl)-N-((3-(trifluoromethyl)isoxazol-5-yl)methyl)-5-(1,1,1-trifluoropropan-2-yloxy)pyrimidine-2-carboxamide,
(S)-6-(4-chlorophenyl)-N-(pyridin-2-ylmethyl)-5-(1,1,1-trifluoropropan-2-yloxy)pyrazine-2-carboxamide, 4-(4-chlorophenyl)-N-((2-cyclopropyloxazol-4-yl)methyl)-5-(2,2,2-trifluoroethoxy)picolinamide,
5-(4-chloro-3-methylphenyl)-N-((2-cyclopropylthiazol-4-yl)methyl)-6-(2,2,2-trifluoroethoxy)nicotinamide,
5-(4-chloro-3-methylphenyl)-6-(2,2,2-trifluoroethoxy)-N-((3-(trifluoromethyl)-1,2,4-oxadiazol-5-yl)methyl)nicotinamide,
4-(3-chloro-4-methylphenyl)-N-((3-methoxyisoxazol-5-yl)methyl)-5-(2,2,2-trifluoroethoxy)picolinamide,
4-(4-chloro-3-methylphenyl)-N-((3-methoxyisoxazol-5-yl)methyl)-5-(2,2,2-trifluoroethoxy)picolinamide,
4-(3,4-dimethylphenyl)-N-((3-methoxyisoxazol-5-yl)methyl)-5-(2,2,2-trifluoroethoxy)picolinamide,
4-(4-chloro-3-methylphenyl)-N-((2-cyclopropylthiazol-4-yl)methyl)-5-(2,2,2-trifluoroethoxy)picolinamide,
4-(4-chloro-3-methylphenyl)-5-(2,2,2-trifluoroethoxy)-N-((3-(trifluoromethyl)-1,2,4-oxadiazol-5-yl)methyl)picolinamide,
4-(3,4-dimethylphenyl)-5-(2,2,2-trifluoroethoxy)-N-((3-(trifluoromethyl)-1,2,4-oxadiazol-5-yl)methyl)picolinamide,
5-p-tolyl-6-(2,2,2-trifluoroethoxy)-N-((3-(trifluoromethyl)-1,2,4-oxadiazol-5-yl)methyl)nicotinamide,
5-(3-chloro-4-methylphenyl)-6-(2,2,2-trifluoroethoxy)-N-((3-(trifluoromethyl)-1,2,4-oxadiazol-5-yl)methyl)nicotinamide,
5-(3-chloro-4-fluorophenyl)-6-(2,2,2-trifluoroethoxy)-N-((3-(trifluoromethyl)-1,2,4-oxadiazol-5-yl)methyl)nicotinamide,
5-(4-chloro-3-fluorophenyl)-6-(2,2,2-trifluoroethoxy)-N-((3-(trifluoromethyl)-1,2,4-oxadiazol-5-yl)methyl)nicotinamide,
5-(4-ethylphenyl)-6-(2,2,2-trifluoroethoxy)-N-((3-(trifluoromethyl)-1,2,4-oxadiazol-5-yl)methyl)nicotinamide,
5-(4-chloro-2-fluorophenyl)-6-(2,2,2-trifluoroethoxy)-N-((3-(trifluoromethyl)-1,2,4-oxadiazol-5-yl)methyl)nicotinamide,
5-(2,3-dihydro-1H-inden-5-yl)-6-(2,2,2-trifluoroethoxy)-N-((3-(trifluoromethyl)-1,2,4-oxadiazol-5-yl)methyl)nicotinamide,
5-(4-chloro-3-fluorophenyl)-N-((3-methoxyisoxazol-5-yl)methyl)-6-(2,2,2-trifluoroethoxy)nicotinamide,
5-(4-cyanophenyl)-6-(2,2,2-trifluoroethoxy)-N-((3-(trifluoromethyl)-1,2,4-oxadiazol-5-yl)methyl)nicotinamide,
5-(4-chlorophenyl)-N-((1-(cyclopropylmethyl)-1H-pyrazol-3-yl)methyl)-6-(2,2,2-trifluoroethoxy)nicotinamide,
5-(3,4-difluorophenyl)-6-(2,2,2-trifluoroethoxy)-N-((3-(trifluoromethyl)-1,2,4-oxadiazol-5-yl)methyl)nicotinamide,
5-(4-chlorophenyl)-N-((3-methyl-1,2,4-oxadiazol-5-yl)methyl)-6-(2,2,2-trifluoroethoxy)nicotinamide,
6-cyclobutoxy-5-(3,4-difluorophenyl)-N-((3-(trifluoromethyl)-1,2,4-oxadiazol-5-yl)methyl)nicotinamide,
5-(4-chlorophenyl)-6-cyclobutoxy-N-((3-(trifluoromethyl)-1,2,4-oxadiazol-5-yl)methyl)nicotinamide
5-(4-chloro-3-fluorophenyl)-6-cyclobutoxy-N-((3-(trifluoromethyl)-1,2,4-oxadiazol-5-yl)methyl)nicotinamide,
5-(4-chloro-3-methylphenyl)-6-cyclobutoxy-N-((3-(trifluoromethyl)-1,2,4-oxadiazol-5-yl)methyl)nicotinamide,
6-(cyclopropylmethoxy)-5-(3,4-difluorophenyl)-N-((3-(trifluoromethyl)-1,2,4-oxadiazol-5-yl)methyl)nicotinamide,
5-(3,4-difluorophenyl)-6-(2-methoxyethoxy)-N-((3-(trifluoromethyl)-1,2,4-oxadiazol-5-yl)methyl)nicotinamide,
5-(4-chloro-3-fluorophenyl)-6-(2-methoxyethoxy)-N-((3-(trifluoromethyl)-1,2,4-oxadiazol-5-yl)methyl)nicotinamide,
5-(4-chloro-3-methylphenyl)-6-(2-methoxyethoxy)-N-((3-(trifluoromethyl)-1,2,4-oxadiazol-5-yl)methyl)nicotinamide,
5-(3,4-difluorophenyl)-N-((3-methoxyisoxazol-5-yl)methyl)-6-(2,2,2-trifluoroethoxy)nicotinamide,
5-benzo[1,2,5]oxadiazol-5-yl-6-(2,2,2-trifluoro-ethoxy)-N-(3-trifluoromethyl-[1,2,4]oxadiazol-5-ylmethyl)-nicotinamide,
5-(4-chlorophenyl)-6-cyclobutoxy-N-(pyridin-2-ylmethyl)nicotinamide,
5-(4-chlorophenyl)-6-(2-hydroxyethoxy)-N-((3-(trifluoromethyl)-1,2,4-oxadiazol-5-yl)methyl)nicotinamide,
(R)-5-(4-chlorophenyl)-6-(tetrahydrofuran-3-yloxy)-N-((3-(trifluoromethyl)-1,2,4-oxadiazol-5-yl)methyl)nicotinamide,
(SR)-5-(4-chlorophenyl)-6-((tetrahydrofuran-3-yl)methoxy)-N-((3-(trifluoromethyl)-1,2,4-oxadiazol-5-yl)methyl)nicotinamide, and
(RS)-5-(4-chloro-phenyl)-6-[(R)-1-(tetrahydro-furan-3-yl)methoxy]-N-(3-trifluoromethyl-[1,2,4]oxadiazol-5-ylmethyl)-nicotinamide,
or pharmaceutically acceptable salts thereof.

Particularly advantageous compounds of formula I of the present invention are the following:
4-(4-chloro-phenyl)-5-(2,2,2-trifluoro-ethoxy)-pyridine-2-carboxylic acid (3-methoxy-isoxazol-5-ylmethyl)-amide,
5-(4-chloro-phenyl)-6-(2,2,2-trifluoro-ethoxy)-N-(3-trifluoromethyl-[1,2,4]oxadiazol-5-ylmethyl)-nicotinamide,
6-(4-chloro-phenyl)-5-(2,2,2-trifluoro-ethoxy)-pyridine-2-carboxylic acid (3-trifluoromethyl-[1,2,4]oxadiazol-5-ylmethyl)-amide,
5-(4-chlorophenyl)-N-((3-methoxyisoxazol-5-yl)methyl)-6-(2,2,2-trifluoroethoxy)pyridazine-3-carboxamide,
4-(4-chlorophenyl)-N-((5-cyclopropylisoxazol-3-yl)methyl)-5-(2,2,2-trifluoroethoxy)picolinamide,
(S)-6-(4-chlorophenyl)-N-((3-(trifluoromethyl)-1,2,4-oxadiazol-5-yl)methyl)-5-(1,1,1-trifluoropropan-2-yloxy)pyrazine-2-carboxamide,
(S)-5-(4-chlorophenyl)-N-((3-(trifluoromethyl)-1,2,4-oxadiazol-5-yl)methyl)-6-(1,1,1-trifluoropropan-2-yloxy)nicotinamide,
4-(4-chlorophenyl)-N-((3-isopropyl-1,2,4-oxadiazol-5-yl)methyl)-5-(2,2,2-trifluoroethoxy)picolinamide,
5-(4-chloro-phenyl)-6-(2,2,2-trifluoro-ethoxy)-pyridazine-3-carboxylic acid (3-cyclopropyl-[1,2,4]oxadiazol-5-ylmethyl)-amide, and
6-(4-chloro-phenyl)-5-(2,2,2-trifluoro-ethoxy)-pyridine-2-carboxylic acid (3-isopropyl-isoxazol-5-ylmethyl)-amide,
5-(4-chloro-phenyl)-6-(2,2,2-trifluoro-ethoxy)-pyridazine-3-carboxylic acid (5-trifluoromethyl-isoxazol-3-ylmethyl)-amide,
4-(4-chlorophenyl)-N-((2-cyclopropyloxazol-4-yl)methyl)-5-(2,2,2-trifluoroethoxy)picolinamide,
5-(4-chloro-3-methylphenyl)-6-(2,2,2-trifluoroethoxy)-N-((3-(trifluoromethyl)-1,2,4-oxadiazol-5-yl)methyl)nicotinamide, 5-(3-chloro-4-methylphenyl)-6-(2,2,2-trifluoroethoxy)-N-((3-(trifluoromethyl)-1,2,4-oxadiazol-5-yl)methyl)nicotinamide, 5-(3-chloro-4-fluorophenyl)-6-(2,2,2-trifluoroethoxy)-N-((3-(trifluoromethyl)-1,2,4-oxadiazol-5-yl)methyl)nicotinamide, 5-(3,4-difluorophenyl)-6-(2,2,2-trifluoroethoxy)-N-((3-(trifluoromethyl)-1,2,4-oxadiazol-5-yl)methyl)nicotinamide, 6-cyclobutoxy-5-(3,4-difluorophenyl)-N-((3-(trifluoromethyl)-1,2,4-oxadiazol-5-yl)methyl)nicotinamide, 5-(4-chloro-3-fluorophenyl)-6-cyclobutoxy-N-((3-(trifluoromethyl)-1,2,4-oxadiazol-5-yl)methyl)nicotinamide, 5-(4-chloro-3-methylphenyl)-6-cyclobutoxy-N-((3-(trifluoromethyl)-1,2,4-oxadiazol-5-yl)methyl)nicotinamide, 5-(3,4-difluorophenyl)-N-((3-methoxyisoxazol-5-yl)methyl)-6-(2,2,2-trifluoroethoxy)nicotinamide, 5-benzo[1,2,5]oxadiazol-5-yl-6-(2,2,2-trifluoro-ethoxy)-N-(3-trifluoromethyl-[1,2,4]oxadiazol-5-ylmethyl)-nicotinamide, and 5-(4-chlorophenyl)-6-(2-hydroxyethoxy)-N-((3-(trifluoromethyl)-1,2,4-oxadiazol-5-yl)methyl)nicotinamide, or pharmaceutically acceptable salts thereof.

The compounds of formula I can be prepared by a process, which process comprises coupling a compound of formula

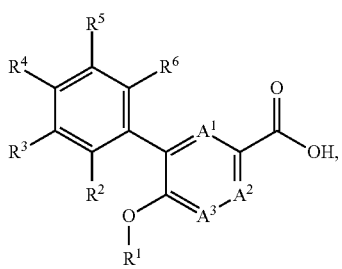

II wherein $A^1$, $A^2$, $A^3$ and $R^1$ to $R^6$ are as defined herein before, with an amine of the formula

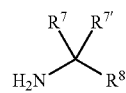

III wherein $R^7$, $R^{7'}$ and $R^8$ are as defined herein before, with the help of a coupling agent under basic conditions, and, if desired, converting the resulting compound of formula I into a pharmaceutically acceptable salt thereof.

Coupling agents for the reaction of compounds of formula II with amines of formula III are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU). In particular, the coupling agent is TBTU. Suitable bases include triethylamine, diisopropylethylamine and, preferably, Hünig's base. Alternative methods known in the art may commence by preparing the acid chloride from II and coupling with an amine of formula III in the presence of a suitable base.

The synthesis of the compounds with the general structure I can be accomplished according to the following schemes.

Following the procedure according to scheme 1, compound AA (6-chloro-5-hydroxy-4-iodo-2-pyridinemethanol, CAN 208519-37-3) can be used as starting material. AA is commercially available or can alternatively be prepared by a two step sequence from 2-chloro-3-pyridinol following literature procedures.

Scheme 1

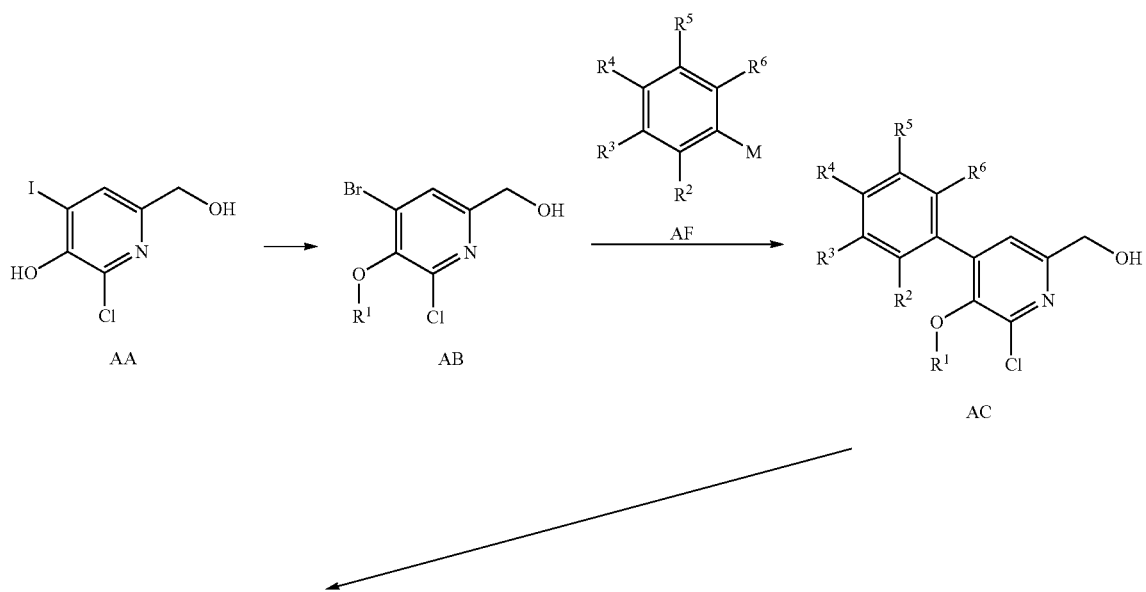

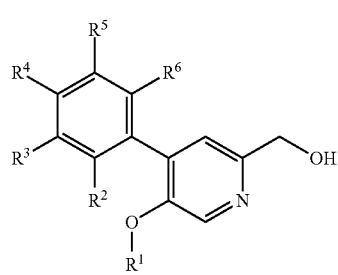

AD

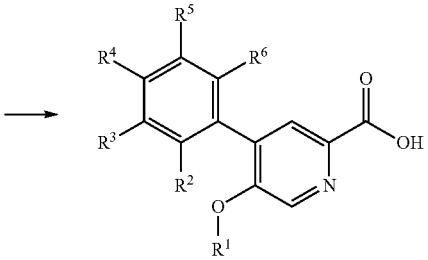

II-a

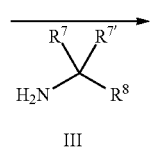

III

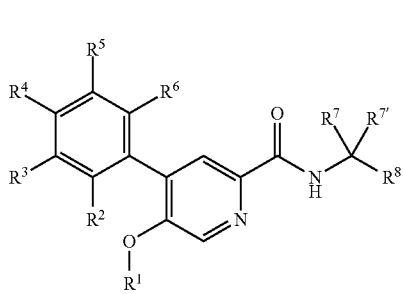

I-a

Compound AB can be prepared from AA by reaction with a suitably substituted primary or secondary alkylhalide $R^1$—X or primary or secondary alkyltrifluoromethanesulfonate $R^1$—OTf in the presence of a base, for example sodium hydride, in a inert solvent, for example hexamethylphosphoramide, at temperatures from room temperature to reflux temperature of the solvent, preferably at elevated temperature e.g. 120° C.

Compound AC can be prepared from AB by coupling a suitably substituted aryl metal species of formula AF, preferably an arylboronic acid or arylboronic acid ester, with AB in the presence of a suitable catalyst, preferably a palladium catalyst and more preferably palladium(II)acetate/triphenylphosphine mixtures or palladium(II) chloride-dppf (1,1'-bis(diphenylphosphino)ferrocene) complexes and a base, preferably triethylamine or sodium carbonate in an inert solvent such as dimethylformamide or toluene.

Compound AD can be obtained by selective hydrogenation of compound AC by methods known in the art, for example by hydrogenation with zinc in acetic acid in the presence of tetramethylammonium bromide at temperatures from room temperature to reflux temperature of the solvent, preferably at a temperature of 50° C.

Compound II-a can be prepared from AD by oxidation using the vast array of possibilities known in the art. A convenient method is the use of a TEMPO catalyzed oxidation with a sodiumchlorite-sodiumhypochlorite mixture in a suitable solvent mixture, preferably in acetonitrile/phosphate buffer mixtures, at temperatures from room temperature to elevated temperatures, preferably at 35° C.

Compound I-a can be prepared from II-a and the corresponding amine of formula III by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformations. A convenient method is to use for example TBTU and a base, for example Hünig's base (N-ethyldiisopropylamine) in an inert solvent such as for example dimethylformamide at room temperature.

Following the procedure according to scheme 2, compound BA (5-bromo-6-chloro-3-pyridinecarboxylic acid methylester, CAN 78686-77) can be used as starting material. BA is commercially available or can alternatively be prepared by a multi step sequence from 6-hydroxy-3-pyridinecarboxylic acid following literature procedures.

Compound BB can be prepared from BA by coupling a suitably substituted aryl metal species of formula AF, preferably a arylboronic acid or arylboronic acid ester, with BA in the presence of a suitable catalyst, preferably a palladium catalyst and more preferably palladium(II)acetate/triphenylphosphine mixtures or palladium(II) chloride-dppf (1,1'-bis(diphenylphosphino)ferrocene) complexes and a base, preferably triethylamine or sodium carbonate in an inert solvent such as dimethylformamide or toluene.

Compound BC can be obtained by saponification of compound BB by methods known in the art, for example by saponification with an alkalimetal hydroxide, for example lithium hydroxide, in a suitable solvent, for example a mixture of THF and water.

Scheme 2

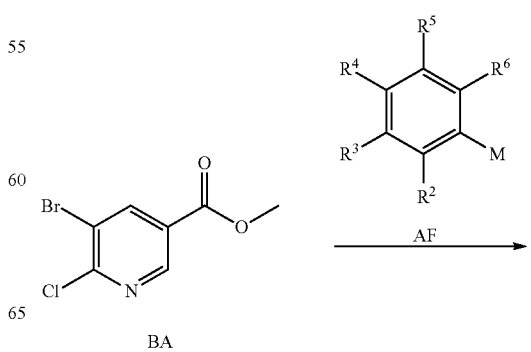

BA

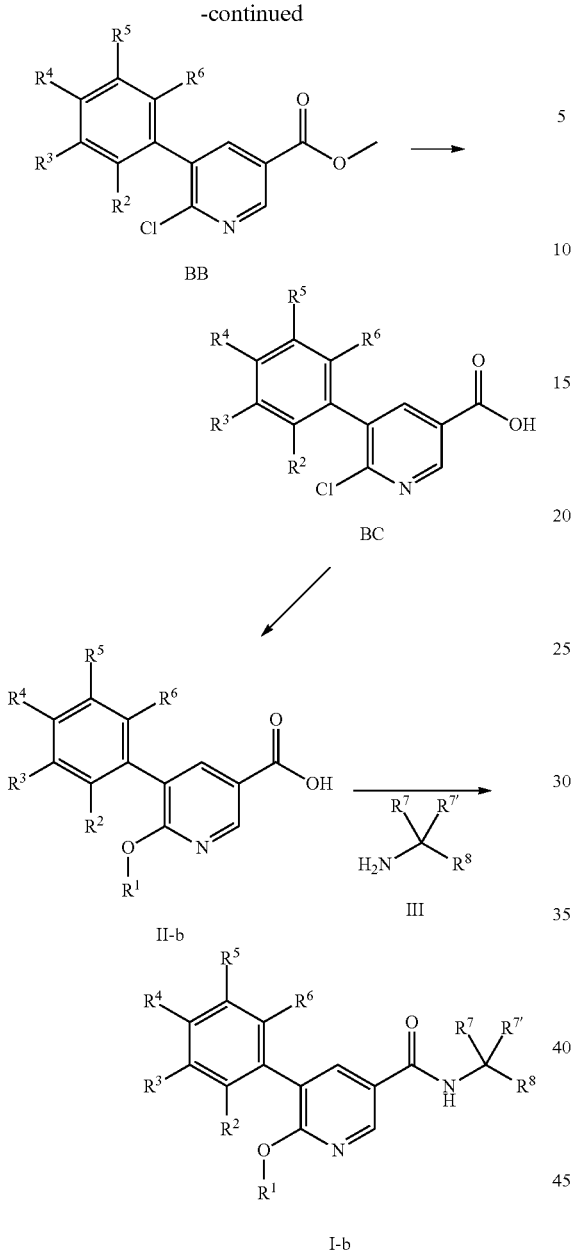

Following the procedure according to scheme 3 compound CA (2,6-dichloro-3-fluoro-pyridine CAN 52208-50-1) can be used as starting material. CA is commercially available.

Scheme 3

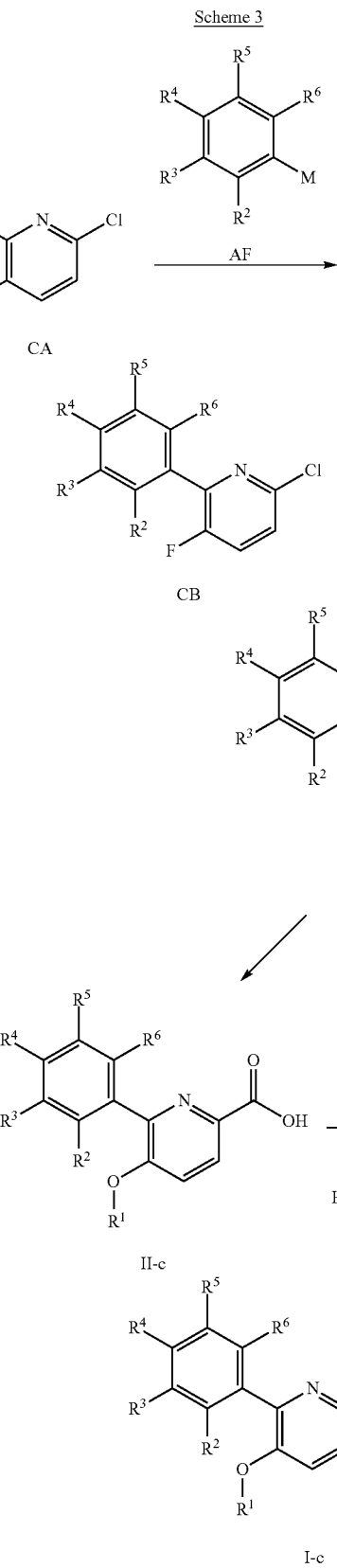

Compound II-b can be prepared from BC by reaction with a suitably substituted primary or secondary alcohol $R^1$—OH in the presence of a base, for example potassium hydroxide, in a inert solvent, for example dimethylsulfoxide, at temperatures from room temperature to reflux temperature of the solvent, preferably at room temperature.

Compound I-b can be prepared from II-b and the corresponding amine of formula III by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformations. A convenient method is to use for example TBTU and a base, for example Hünig's base (N-ethyldiisopropylamine) in an inert solvent such as for example dimethylformamide at room temperature.

Compounds of the general formula CB can be prepared from compound CA by coupling a suitably substituted aryl metal species of the general formula AF, preferably an arylboronic acid or arylboronic acid ester, with compounds of the general formula CA in the presence of a suitable catalyst, preferably a palladium catalyst and more preferably palladium(II)acetate/triphenylphosphine mixtures or palladium (II) chloride-dppf (1,1'-bis(diphenylphosphino) ferrocene) complexes and a base, preferably triethylamine or sodium carbonate in an inert solvent such as dimethylformamide, toluene, tetrahydrofuran, water or acetonitrile preferably tetrahydrofuran and mixtures of tetrahydrofuran and water.

Compounds of the general formula CC can be obtained from compounds of the general formula CB by reaction with an alcohol of the general formula $R^3OH$ more specifically with 2,2,2-trifluoroethanol and cyclopropylmethanol in the presence of a suitable base such as sodium hydroxide, sodium hydride and cesium carbonate in an inert solvent such as tetrahydrofuran, dimethylformamide or dimethylsulfoxide, in particular dimethylsulfoxide, at a temperature between −20° C. to reflux, preferably at room temperature.

Compounds of the general formula II-c can be obtained from compounds of the general formula CC by transition metal catalyzed, more specifically palladium catalyzed, preferentially palladium(II) chloride-dppf catalyzed reaction with carbon monoxide in a suitable solvent such as a primary alcohol, particularly methanol, at pressures of carbon monoxide of 1 to 200 bar, in particular 1 to 70 bar and temperatures of 0 to 150° C., particularly 1 to 100° C. followed by saponification of the resulting ester by methods well known to the ones skilled in the art.

Compounds of the general formula I-c can be prepared from compounds of the general formula II-c and the corresponding amine of the general formula III by suitable amide bond forming reactions described above.

Following the procedure according to scheme 4 certain compounds of the general formula DA (e.g. 3-chloro-6-methoxy-pyridazine, CAN 1722-10-7) are commercially available and can be used as starting materials. Alternatively, compounds of the general formula DA can be obtained from 3,6-dichloro-pyridazine (CAN 141-30-0) by reaction with an alcohol of the general formula $R^1OH$ more specifically with cyclopropylmethanol in the presence of a suitable base such as sodium hydroxide, sodium hydride and cesium carbonate in an inert solvent such as tetrahydrofuran, dimethylformamide or dimethylsulfoxide, particularly dimethylsulfoxide, at temperatures between −20° C. to reflux, in particular at room temperature.

Compounds of the general formula DB can be obtained from compounds of the general formula DA by ortho directed metalation using a suitable base such as LDA or lithium 2,2,6,6-tetramethylpiperidide in an inert solvent such as tetrahydrofuran at low temperatures, particularly −110° C. to −78° C. followed by reaction with iodine at low temperatures, particularly at −110° C. to −78° C.

Compounds of the general formula DC can be obtained by coupling a suitably substituted aryl metal species of the general formula AF, preferably an arylboronic acid or arylboronic acid ester, with compounds of the general formula DB in the presence of a suitable catalyst, preferably a palladium catalyst and more preferably palladium(II)acetate/triphenylphosphine mixtures or palladium(II) chloride-dppf (1,1'-bis(diphenylphosphino)ferrocene) complexes and a base, particularly triethylamine or sodium carbonate in an inert solvent such as dimethylformamide, toluene, tetrahydrofuran or acetonitrile, in particular tetrahydrofuran.

Compounds of the general formula II-d can be obtained from compounds of the general formula DC by palladium acetate catalyzed reaction with carbon monoxide in a suitable solvent such as a primary alcohol, particularly methanol, at pressures of carbon monoxide of 1 to 200 bar, particularly 1 to 70 bar and temperatures of 0° C. to 150° C., in particular 1° C. to 100° C. followed by saponification of the resulting ester by methods well known to the ones skilled in the art.

Ether side chains $R^1O$ that are incompatible with the above described ortho directed metallation protocol, such as trifluoroethyl ethers can alternatively be introduced according to scheme 4 by reactions of compounds with the formula DC, in which $R^1$ represents a simple alkyl group such as methyl or cyclopropylmethyl, with suitable acids such as hydrochloric acid in an inert solvent such as dioxane to yield compounds of the general formula DD.

Scheme 4

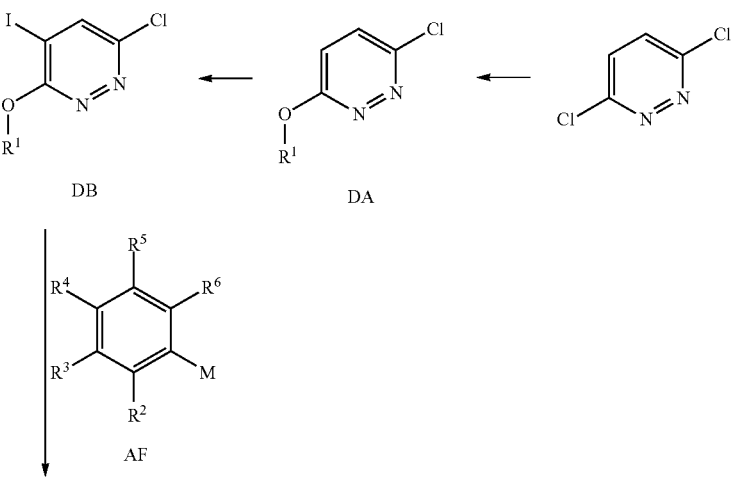

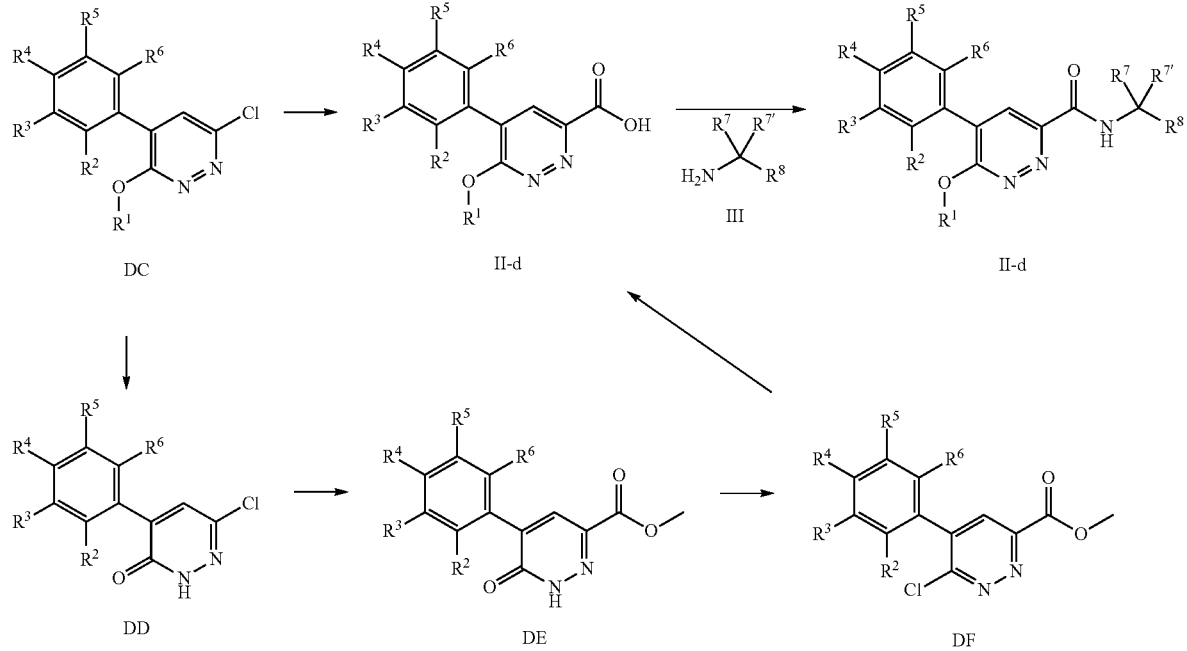

Compounds of the general formula DE can be obtained from compounds of the general formula DD by Pd catalyzed, preferentially PdCl$_2$.dppf catalyzed reaction with carbon monoxide in a suitable solvent such as a primary alcohol, particularly methanol, at pressures of carbon monoxide of 1 to 200 bar, in particular 1 to 70 bar and temperatures of 0° C. to 150° C., particularly 0 to 120° C.

Compounds of the general formula DF can be obtained from compounds of the general formula DE by reaction with a chlorinating agent such as phosphoroxychloride in a suitable solvent or neat at temperatures ranging from room temperature to reflux.

Compounds of the general formula II-d can be obtained from compounds of the general formula DF by reaction with an alcohol of the general formula R$^1$OH, more specifically with 2,2,2-trifluoroethanol, in the presence of a suitable base such cesium carbonate in an inert solvent such as 2,2,2-trifluoroethanol, tetrahydrofuran, dimethylformamide or dimethylsulfoxide, particularly dimethylsulfoxide, at temperatures between −20° C. to reflux, in particular at room temperature, followed by saponification of the resulting ester by methods well known to the ones skilled in the art.

Compounds of the general formula I-d can be prepared from compounds of the general formula II-d and the corresponding amine of the general formula III by suitable amide bond forming reactions described above.

Following the procedure according to scheme 5, 2,4-dichloro-5-fluoro-pyrimidine (CAS RN 2927-71-1) can be used as starting material for the preparation of compounds of the general formula EA by coupling with a suitably substituted aryl metal species of the general formula AF, particularly an arylboronic acid or arylboronic acid ester in the presence of a suitable catalyst, in particular a palladium catalyst and more particularly palladium(II)acetate/triphenylphosphine mixtures or palladium(II) chloride-dppf (1,1'-bis(diphenylphosphino)ferrocene) complexes and a base such as triethylamine or sodium carbonate in an inert solvent such as dimethylformamide, toluene, tetrahydrofuran or acetonitrile, particularly in mixtures of tetrahydrofuran and water.

Compounds of the general formula EB can be obtained from compounds of the general formula EA by reaction with an alcohol of the general formula R$^1$OH more specifically with 2,2,2-trifluoroethanol and cyclopropylmethanol in the presence of a suitable base such as sodium hydroxide, sodium hydride and cesium carbonate in an inert solvent such as tetrahydrofuran, dimethylformamide or dimethylsulfoxide, particularly dimethylsulfoxide, at temperatures between −20° C. to reflux, in particular at room temperature.

Compounds of the general formula II-e can be obtained from compounds of the general formula EB by palladium (preferentially PdCl$_2$.dppf) catalyzed reaction with carbon monoxide in a suitable solvent such as a primary alcohol, particularly methanol, at pressures of carbon monoxide of 1 to 200 bar, particularly 1 to 70 bar and temperatures of 0 to 150° C., particularly 0° C. to 120° C., followed by saponification of the resulting ester by methods well known to the ones skilled in the art.

Compounds of the general formula I-e can be prepared from compounds of the general formula II-e and the corresponding amine of the general formula III by suitable amide bond forming reactions described above.

Scheme 5

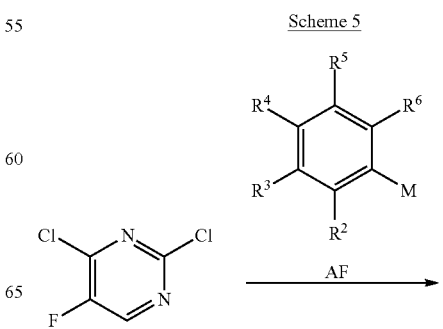

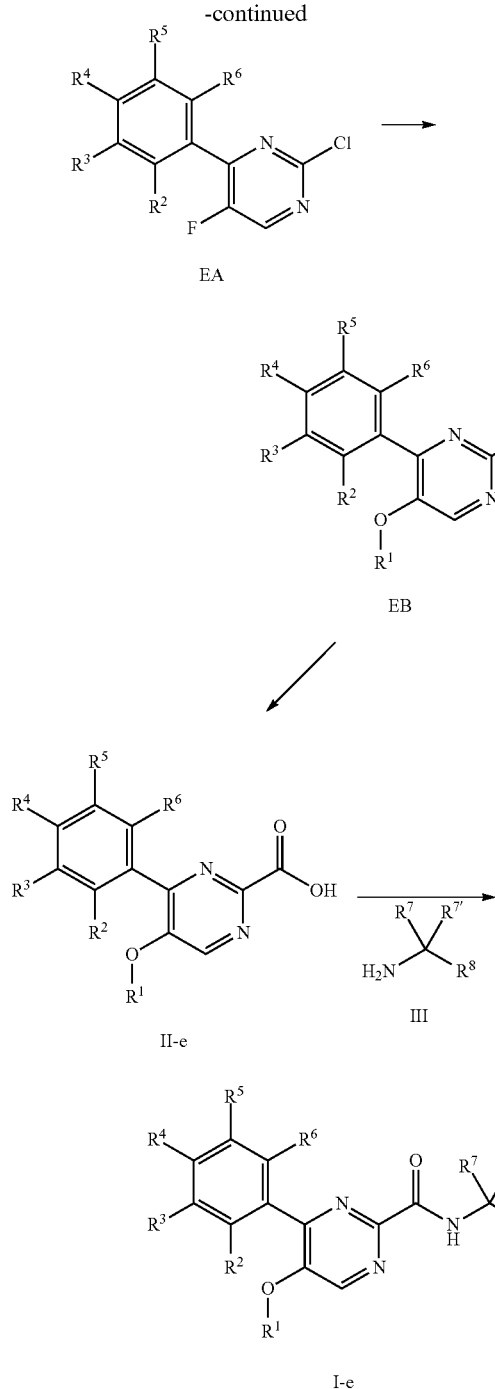

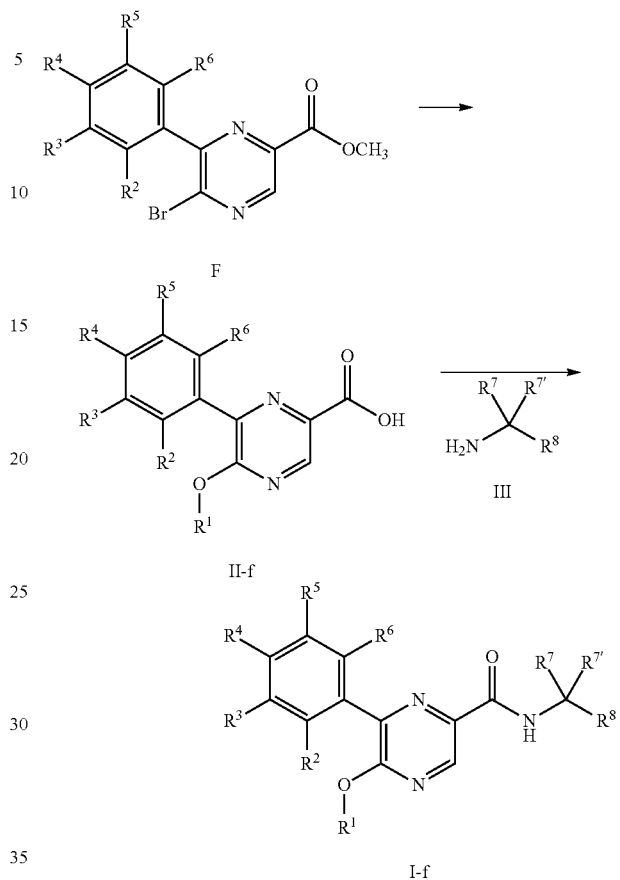

Scheme 6

Following the procedure according to scheme 6 compounds of the general formula IIf can be obtained from compound F (CAN 960247-79-4,2-pyrazinecarboxylic acid, 5-bromo-6-(4-chlorophenyl)-, methyl ester) by reaction with an alcohol of the general formula R¹OH, more specifically with 2,2,2-trifluoroethanol, (S)-1,1,1-trifluoro-propan-2-ol and cyclopropylmethanol in the presence of a suitable base such as sodium hydroxide, sodium hydride and cesium carbonate in an inert solvent such as tetrahydrofuran, dimethylformamide or dimethylsulfoxide, particularly dimethylsulfoxide, at temperatures between −20° C. to reflux, in particular at room temperature.

As described above, the compounds of formula I of the present invention, or pharmaceutically acceptable salts thereof, can be used as medicaments for the treatment and/or prophylaxis of diseases which can be treated with HDL-cholesterol raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia. The use as medicament for the treatment and/or prevention of dyslipidemia, atherosclerosis and cardiovascular diseases is of particular interest.

The invention therefore also relates to pharmaceutical compositions comprising a compound of formula I as defined above, or a pharmaceutically acceptable salt thereof, and a pharmaceutically acceptable carrier and/or adjuvant. The pharmaceutical compositions are useful in the treatment and/or prophylaxis of diseases which can be treated with HDL-cholesterol raising agents.

Thus, the invention relates to a pharmaceutical composition as defined above for use in the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which can be treated with HDL-cholesterol raising agents, which method comprises administering a therapeutically effective amount of a compound of formula I, or a pharmaceutically acceptable salt thereof, to a patient in need thereof. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia. A method for the treatment and/or prophylaxis of dyslipidemia, atherosclerosis and cardiovascular diseases is preferred.

The invention also relates to the compounds of formula I, or pharmaceutically acceptable salts thereof, for use as medicaments. More specifically, the invention relates to compounds of formula I, or pharmaceutically acceptable salts thereof, for use as HDL-cholesterol raising agents. Thus, the invention is concerned with compounds of formula I, or pharmaceutically acceptable salts thereof, for use in the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia, in particular for use in the treatment and/or prophylaxis of dyslipidemia, atherosclerosis and cardiovascular diseases.

In addition, the invention relates to the use of compounds of formula I as defined above, or pharmaceutically acceptable salts thereof, for the preparation of a medicament for the treatment and/or prophylaxis of diseases can be treated with HDL raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia. The use of compounds of formula I as defined above, or pharmaceutically acceptable salts thereof, for the preparation of medicaments for the treatment and/or prophylaxis of dyslipidemia, atherosclerosis and cardiovascular diseases is of particular interest.

In addition, HDL raising agents of formula I, or pharmaceutically acceptable salts thereof, are useful in combination or association with another compound, said compound being selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

The invention therefore also relates to pharmaceutical compositions comprising a compound of formula I as defined above, or a pharmaceutically acceptable salt thereof, in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant, as well as a pharmaceutically acceptable carrier and/or adjuvant.

The invention further relates to compounds of formula I as defined above, or pharmaceutically acceptable salts thereof, in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant for use in the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

The invention also relates to a method for the treatment and/or prophylaxis of diseases which can be treated with HDL-cholesterol raising agents, which method comprises administration of a therapeutically effective amount of a compound according to formula I, or a pharmaceutically acceptable salt thereof, in combination or association with a therapeutically effective amount of a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

Pharmaceutical Compositions

The compounds of formula I and/or their pharmaceutically acceptable salts can be used in the form of pharmaceutical compositions for enteral, parenteral or topical administration. They can be administered, for example, perorally, e.g. in the form of tablets, coated tablets, dragées, hard and soft gelatine capsules, solutions, emulsions or suspensions, orally, e.g. in the form of buccal cavities, rectally, e.g. in the form of suppositories, parenterally, e.g. in the form of injection solutions or infusion solutions for intramuscular, intravenous or subcutaneous injection, or topically, e.g. in the form of ointments, creams or oils. Oral administration is of particular interest.

The production of the pharmaceutical compositions can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The therapeutically effective amount or dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 100 mg, especially about 1 to 50 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 1-100 mg, preferably 5-50 mg, of a compound of formula I.

The following examples C1 to C3 illustrate typical compositions of the present invention, but serve merely as representative thereof.

Example C1

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example C2

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C3

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Pharmacological Tests

The following tests were carried out in order to determine the activity of the compounds of formula I and their valuable pharmacological properties.

Detection of Upregulation of ABCA1 Protein in Cells

The ability of compounds of the invention to increase the level of ABCA1 protein is determined in replicate cultures of THP-1 macrophage cells in 96-well microplates. Cells are plated at an initial density of 100,000 cells/well in 100 µl medium and differentiated to adherent macrophages with the addition of PMA (100 nM) for 68 hrs in 10% fetal bovine serum, 3 µl/L of b-mercaptoethanol, RPMI-1640 medium. Then, cells are incubated with RPMI-1640 medium containing 1% FCS, 25 µg/ml acetylated LDL, for 24 hours at 37°. Following incubation with acetylated LDL, cells are washed twice with 50 µl PBS and incubated with 100 µl of RPMI-1640 medium containing the compound of interest solubilized in DMSO for an additional 24 hrs. The final DMSO concentration in presence of cells is maintained at 0.5%. ApoA-I binding assay using High Content Image Analysis is initiated by replacing with fresh medium, RPMI without Phenol Red, 0.2% BSA containing AlexaFluor®647 labeled ApoA-I for 2 h/37° C./5% CO2. Then, cells are fixed with 4% Formaldehyde in PBS (15 min, RT). Following Nuclei are stained with Hoechst solution (3 µM PBS) and Cytoplasm with Cell Mask Blue (2 µg/ml PBS), 15 min, RT. Finally the stained cells are fixed with a second round of formaldehyde treatment. Fixed stained cells are washed and kept in PBS at 4° C. and can be read immediately until one month after preparation. That the binding of ApoA-I indeed reflected the level of ABCA1 in the cell, was demonstrated by loss of signal when ABCA1 expression was artificially reduced by transfection with small interfering RNA's.

The Alexa Fluor 647-labeled Apolipoprotein A-I (20 nM) was prepared as follows: Human recombinant Apolipoprotein A-I (ApoA-I) was exchanged to a buffer of 0.02 M NaHCO$_3$ at pH 8.2 on an NAP desalting column (GE Healthcare) and brought to a concentration to 40 µM (1.13 mg/ml) by adjustment with the same buffer. The ApoA-I was fluorescently labeled by incubation with Alexa Fluor carboxylic acid succimidyl ester. (Alexa Fluor 647, Invitrogen A-20006) at a 2:1 molar ratio (Alexa to ApoA-I) for 1 h under shaking at RT. The remaining unconjugated label was removed by buffer exchange to 0.02M NaHCO$_3$ at pH 8.2.

Imaging and data collection were performed on an OPERA confocal microplate imaging reader using a 20× water immersion objective and UV360 or 405 laser to identify the cell nuclei and a 635 laser to identify the fluorescent ApoA-I. Eight fields of view are captured per well. Image capture and analysis was performed with the Acapella software. Background fluorescence detected in control wells without ApoA-I was subtracted.

Using XLfit3 program (ID Business Solutions Ltd. UK), the model 205 for Dose Response One Site is used to calculate the EC$_{50}$ values. The compounds of the present invention exhibit EC$_{50}$ values in a range of 0.1 µM to 10 µM in the ABCA1 protein detection assay. Preferably, the compounds of the present invention have EC$_{50}$ values in a range of 0.1 µM to 3 µM.

TABLE 1

| ABCA1 protein increasing efficacy | |
|---|---|
| Example | EC$_{50}$ [µM] |
| 1 | 2.01 |
| 2 | 1.09 |
| 3 | 1.24 |
| 4 | 2.8 |
| 5 | 2.1 |
| 6 | 7.8 |
| 7 | 1.5 |
| 8 | 0.9 |
| 9 | 0.9 |
| 11 | 1.5 |
| 12 | 1.18 |
| 14 | 0.95 |
| 15 | 0.84 |
| 18 | 6.91 |
| 22 | 2.27 |
| 23 | 0.93 |
| 25 | 1.47 |
| 27 | 0.97 |
| 28 | 0.87 |
| 29 | 1.87 |
| 31 | 0.53 |
| 34 | 0.77 |
| 38 | 0.95 |
| 42 | 0.8 |
| 44 | 1.02 |
| 46 | 0.78 |
| 48 | 0.73 |
| 60 | 0.75 |
| 61 | 0.82 |
| 64 | 0.86 |
| 67 | 0.78 |
| 70 | 1.56 |
| 71 | 4.29 |

TABLE 1-continued

| ABCA1 protein increasing efficacy | |
|---|---|
| Example | EC$_{50}$ [µM] |
| 72 | 0.5 |
| 74 | 1.3 |
| 76 | 1.64 |
| 77 | 0.33 |
| 79 | 1.17 |
| 80 | 3.13 |
| 81 | 0.89 |
| 89 | 1.96 |
| 91 | 0.62 |
| 94 | 0.31 |
| 99 | 1.25 |
| 100 | 0.58 |

Cholesterol Efflux Assay

The ability of compounds of the invention to stimulate cholesterol efflux is determined in replicate cultures of THP-1 cells in 96-well microplates. Cells are plated at an initial density of 150,000 cells/well and differentiated to macrophages with the addition of PMA (100 ng/ml) for 72 hrs in 10% fetal bovine serum, 3 µl/L of b-mercaptoethanol, RPMI-1640 medium. Cells are washed once with RPMI-1640 and loaded with RPMI-1640 medium containing 2% FCS, 50 µg/ml acetylated LDL, and 10 µCi/ml [$^3$H]cholesterol for 48 hours at 37° C. After loading the cells are washed once with RPMI-1640 and incubated with the compound of interest from DMSO solutions for an additional 24 hrs in RPMI-1640 medium containing 1 mg/ml fatty acid free-bovine serum albumin (BSA). Upon incubation cells are washed once, and cholesterol efflux is induced by the addition of 10 µg/ml Apolipoprotein AI in RPMI-1640 containing 1 mg/ml BSA and in the presence of the compound for an additional 6 hrs. Following incubation radioactivity is determined in the supernatants and cholesterol efflux is expressed as the percent stimulation over replicate cultures treated only with DMSO. Sigmoidal curves were fitted using the XLfit3 program (ID Business Solutions Ltd. UK) and EC$_{50}$ values were determined.

The compounds of the present invention exhibit EC$_{50}$ values in a range of 0.1 µM to 3.0 µM in the cholesterol efflux assay. Preferably, the compounds of the present invention have EC$_{50}$ values in a range of 0.1 µM to 1.5 µM.

CB1 and CB2 Receptor Affinity

The affinity of the compounds of the invention for cannabinoid receptors was determined using membrane preparations of human embryonic kidney (HEK) cells in which the human CB1 receptor is transiently transfected using a Semliki Forest Virus system in conjunction with [3H]-CP-55,940 as radioligand. After incubation of freshly prepared cell membrane preparation with the [$^3$H]-ligand, with or without addition of compounds of the invention, separation of bound and free ligand was performed by filtration over glass fiber filters. Radioactivity on the filter was measured by scintillation counting.

The affinity of the compounds of the invention for cannabinoid CB2 receptors was determined using membrane preparations of human embryonic kidney (HEK) cells in which the human CB2 receptor is transiently transfected using a Semliki Forest Virus system in conjunction with [$^3$H]-CP-55,940 as radioligand. After incubation of freshly prepared cell membrane preparation with the [$^3$H]-ligand, with or without addition of compounds of the invention, separation of bound and free ligand was performed by filtration over glass fiber filters. Radioactivity on the filter was measured by scintillation counting.

The ability of the compounds to displace the radioligand [$^3$H]-CP-55,940 was measured at a concentration of 10 μM and values provided as [% inhibition @ 10 μM] both for the CB 1 and CB2 receptor assay, The lower % inhibition is, the lower the likelihood of side effects based on CB1 or CB2 receptor inhibition is.

The compounds of the present invention exhibit values below 50% inhibition in both the CB1 and CB2 receptor assay at a concentration of 10 μM. Preferably, the compounds of the present invention exhibit values below 35% inhibition in both the CB1 and CB2 receptor assays and even more preferably below 20% in both assays.

TABLE 2

| | CB1 and CB2-receptor affinity | |
|---|---|---|
| Example | CB1 receptor affinity [% inhibition @ 10 μM] | CB2 receptor affinity [% inhibition @ 10 μM] |
| 1 | 32 | 28 |
| 2 | 30 | 14 |
| 3 | 38 | 18 |
| 4 | 26 | 33 |
| 5 | 48 | 5 |
| 6 | 5 | 15 |
| 7 | 22 | 6 |
| 8 | 24 | 10 |
| 9 | 18 | 1 |
| 10 | 28 | 28 |
| 11 | 25 | 12 |
| 12 | 43 | −4 |
| 13 | 35 | 46 |
| 14 | 48 | 12 |
| 15 | 45 | −6 |
| 16 | 38 | 15 |
| 17 | 48 | 45 |
| 18 | 28 | 24 |
| 19 | 30 | 43 |
| 20 | 33 | 34 |
| 21 | 44 | 35 |
| 22 | 40 | 6 |
| 23 | 18 | 7 |
| 24 | 39 | 16 |
| 25 | 11 | 17 |
| 26 | 40 | 22 |
| 27 | 40 | 24 |
| 28 | 42 | 29 |
| 29 | 27 | 17 |
| 30 | 48 | 38 |
| 31 | 47 | 11 |
| 32 | 47 | 26 |
| 33 | 33 | 26 |
| 34 | 33 | 14 |
| 35 | 50 | 22 |
| 36 | 36 | 14 |
| 37 | 40 | 20 |
| 38 | 32 | −2 |
| 39 | 26 | 21 |
| 40 | 29 | 19 |
| 41 | 23 | 19 |
| 42 | 34 | 13 |
| 43 | 37 | 14 |
| 44 | 29 | 8 |
| 45 | 37 | −2 |
| 46 | 30 | 0 |
| 47 | 46 | 16 |
| 48 | 35 | 19 |
| 49 | 36 | 13 |
| 50 | 38 | −5 |
| 51 | 47 | 2 |
| 52 | 38 | 43 |
| 53 | 43 | 23 |
| 54 | 20 | 12 |
| 55 | 44 | 33 |
| 56 | 38 | 32 |
| 57 | 31 | 36 |
| 58 | 42 | 19 |
| 59 | 49 | −2 |
| 60 | 30 | −3 |
| 61 | 32 | 17 |
| 62 | 44 | 24 |
| 63 | 36 | 38 |
| 64 | 33 | 7 |
| 65 | 18 | missing |
| 66 | 49 | 18 |
| 67 | 25 | 3 |
| 68 | 45 | 3 |
| 69 | 34 | 40 |
| 70 | 28 | 14 |
| 71 | 2 | −7 |
| 72 | 34 | −1 |
| 73 | 22 | 45 |
| 74 | 11 | 22 |
| 75 | 19 | 34 |
| 76 | 8 | 9 |
| 77 | 4 | 11 |
| 78 | 17 | 5 |
| 79 | 42 | 4 |
| 80 | 15 | −4 |
| 81 | 4 | 7 |
| 82 | 30 | 27 |
| 83 | 44 | −2 |
| 84 | 49 | 21 |
| 85 | 7 | 8 |
| 86 | 37 | 9 |
| 87 | 45 | 3 |
| 88 | 48 | 11 |
| 89 | 28 | 4 |
| 90 | 50 | 14 |
| 91 | 23 | 12 |
| 92 | 43 | 9 |
| 93 | 18 | 7 |
| 94 | 19 | 2 |
| 95 | 39 | 21 |
| 96 | 45 | 8 |
| 97 | 48 | 25 |
| 98 | 41 | 16 |
| 99 | 20 | 9 |
| 100 | 15 | 8 |
| 101 | 45 | 37 |
| 102 | 26 | −4 |
| 103 | 47 | 24 |
| 104 | 39 | 9 |
| 105 | 47 | 17 |

Further demonstration of biological activities of the compounds of the present invention may be accomplished through the following in vivo assays that are well known in the art.

Effects on Plasma Lipid Levels in Lean, Chow Fed Rats

The effects of compounds of compounds of formula I on plasma lipid levels were determined in lean, chow-fed Sprague-Dawley rats with compounds administered by p.o. gavage. After one week of acclimation, blood samples were collected from 4 hour-fasted animals for plasma lipid determination. Animals were then assigned to treatment groups based on HDL-cholesterol levels. Compounds of formula I were administered by gavage, once daily for five days. Control animals received vehicle alone. Blood was collected on day five from 4 hour-fasted rats, 2 hours after a final treatment, for plasma lipid analysis. Total cholesterol, HDL-cholesterol, and triglycerides were determined by measuring total cholesterol, HDL-cholesterol, and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Obese, High Fat Diet Fed Rats

Efficacy of compounds in modulating plasma lipid levels was determined also in obese male Sprague Dawley rats after 28-29 days administration of compounds. Male Sprague-Dawley rats of 10 weeks of age were fed a high fat diet during 3 weeks. Obese rats were distributed in groups according to homogeneous BW and FI evaluated a week before the start of the treatment. Treatment was administered as food-Admix. On day 29, blood was taken in the morning under slight anesthesia (retro-orbital method) in post-prandial conditions i.e. 4 h after food was removed. Plasma was separated from blood by low speed centrifugation and selected organs were taken (e.g liver, fat). Total cholesterol, HDL-cholesterol, and triglycerides were determined by measuring total cholesterol, HDL-cholesterol, LDL-cholesterol and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Hamsters

Efficacy of compounds in modulating plasma lipid levels was determined in hamsters after 5 days of daily administration of compounds. Male hamsters of 6-8 weeks of age were used in the studies. After one week of acclimation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol, LDL-cholesterol, and VLDL-cholesterol levels were also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Cholesterol/Fat Fed Hamsters

Efficacy of compounds in modulating plasma lipid levels was determined in hamsters after 5 days of daily administration of compounds. Male hamsters of 6-8 weeks of age were used in the studies. After one week of acclimation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol was also determined after selective precipitation of HDL from plasma by standard procedures.

EXAMPLES

MS=mass spectrometry; EI=electron ionization; ESI=electrospray; NMR data are reported in parts per million (δ) relative to internal tetramethylsilane and are referenced to the deuterium lock signal from the sample solvent ($d_6$-DMSO unless otherwise stated); coupling constants (J) are in Hertz, mp=melting point; bp=boiling point; HPLC=LC=high performance liquid chromatography, Rt=retention time, TLC=thin layer chromatography, RT=room temperature, TBTU=O-(Benzotriazol-1-yl)-N,N',N'-tetramethyl-uronium-tetrafluoroborate; TEMPO=2,2,6,6-tetra-methylpiperidine 1-oxyl radical, DMF=dimethylformamide, DMSO=dimethyl-sulfoxide, THF=tetrahydrofuran, CAN=CAS Registry Number.

Preparation of Intermediates

Example A

Preparation of [6-chloro-4-iodo-5-(2,2,2-trifluoro-ethoxy)-pyridin-2-yl]-methanol

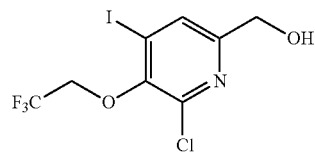 [SMILES: OCc1cc(I)c(OCC(F)(F)F)c(Cl)n1]

6-Chloro-5-hydroxy-4-iodo-2-pyridinemethanol (CAS Registry No. 208519-37-3) (21.5 g, 75 mmol) was dissolved in hexamethylphosphoramide (210 mL). Over a period of 30 min sodium hydride (3.0 g of 60% dispersion in oil, ~75 mmol) was added with stirring at room temperature. The mixture was stirred for another 45 min at room temperature and 2,2,2-trifluoroethyl trifluoromethane sulfonate (12.5 mL, 90 mmol) was added drop wise with stirring and temperature control (<40° C.). The mixture was stirred for 18 h at 120° C., cooled to room temperature and poured into water (800 mL). The mixture was acidified with 2N—HCl (50 mL) and extracted with ethyl acetate (2×350 mL). Organic phases were washed with water (2×400 mL), pooled and dried with $Na_2SO_4$. Solvents were evaporated and the brown, solid residue (27.9 g) was purified by chromatography on silica with ethyl acetate/n-heptane (1:1) to give the title compound as a white solid (24.8 g, 90%), LC-MS (UV peak area/ESI) 100%, 367.916 (M+H)$^+$.

Example B

Preparation of 6-chloro-4-(4-chloro-phenyl)-5-(2,2,2-trifluoro-ethoxy)-pyridin-2-yl]-methanol

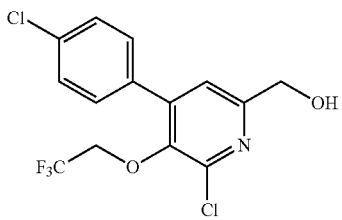 [SMILES: OCc1cc(-c2ccc(Cl)cc2)c(OCC(F)(F)F)c(Cl)n1]

[4-Iodo-6-chloro-5-(2,2,2-trifluoro-ethoxy)-pyridin-2-yl]-methanol (24.7 g, 67 mmol) was suspended in toluene (300 mL). Under Argon was added [1,1'-bis(diphenylphosphino)-ferrocene]palladium(II) dichloride dichloromethane adduct (1.65 g, 2 mmol), 4-chlorophenyl-boronic acid (10.5 g, 67 mmol) and 2.0 M Na₂CO₃-solution (67.2 mL, 134 mmol) with stirring. The mixture was stirred for 90 min at 90° C. and cooled to room temperature. Water (150 mL) was added and the mixture was extracted with ethyl acetate (2×150 mL); organic phase were pooled and dried with Na₂SO₄. Solvents were evaporated and the brown, oily residue (27.7 g) was purified by chromatography on silica with ethyl acetate/n-heptane (1:2) to give the title compound as a brown oil (24.1 g, quant), LC-MS (UV peak area/ESI) ~100%, 352.0116 (M+H)⁺.

Example C

Preparation of [4-(4-chloro-phenyl)-5-(2,2,2-trifluoro-ethoxy)-pyridin-2-yl]-methanol

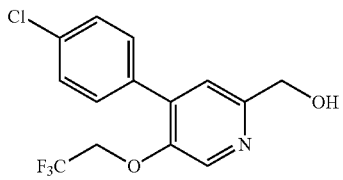 [SMILES: OCc1cc(-c2ccc(Cl)cc2)c(OCC(F)(F)F)cn1]

6-Chloro-4-(4-chloro-phenyl)-5-(2,2,2-trifluoro-ethoxy)-pyridin-2-yl]-methanol (24.1 g, 68 mmol) was dissolved in acetic acid (80 mL). The solution was warmed to 40° C., tetramethylammoniumbromide (0.105 g, 0.7 mmol) was added and activated zinc-powder (26.8 g, 410 mmol) was added in portions (2 g every 30 min) with stirring (argon atmosphere). The suspension was stirred for 16 h at 50° C. after which time another batch of activated zinc-powder (10 g, in 5 portions of 2 g each) was added. Stirring at 50° C. continued for another 3 h after which time the mixture was cooled to room temperature and poured into water (1000 mL). Concentrated NaOH solution (~150 mL) was added till pH 14 was attained. Ethyl acetate (500 mL) was added and the mixture stirred in the cold for 15 min. The suspension was filtered through Celite® was and the filter cake thoroughly washed with ethyl acetate (5×300 mL). The filtrate was collected, phases were separated, the water phase was extracted once with ethyl acetate (500 mL), and organic phases were pooled and dried with Na₂SO₄. Solvents were evaporated and the brown, solid residue (21.1 g) was purified by chromatography on silica with ethyl acetate/n-heptane (2:1) to give the title compound as a off white solid (17.4 g, 80%), LC-MS (UV peak area/ESI) 100%, 318.050 (M+H)⁺.

Example D

Preparation of 4-(4-chloro-phenyl)-5-(2,2,2-trifluoro-ethoxy)-pyridine-2-carboxylic acid

[4-(4-Chloro-phenyl)-5-(2,2,2-trifluoro-ethoxy)-pyridin-2-yl]-methanol (17.4 g, 55 mmol) was dissolved in acetonitrile (235 mL). Phosphate buffer (pH 6.7, 220 mL) and 2,2,6,6-tetra-methylpiperidine 1-oxyl radical (TEMPO, 0.6 g) was added and the solution was warmed to 35° C. To this warm solution under argon was added with stirring over 2 h simultaneously a solution of NaOCl₂ (12.4 g) in water (58 mL) and NaOCl (0.85 mL, 10% solution) in water (35 mL). Stirring was continued for 20 h at 35° C. after which time the solution was cooled to room temperature and quenched by addition of in sequence water (420 mL), 2 N NaOH solution (65 mL) and Na₂SO₃ solution (17.1 g in 285 mL water). This mixture was stirred for 30 min and acidified with 2 N HCl (175 mL). The mixture was extracted once with ethyl acetate/THF (800/150 mL), and once with ethyl acetate (500 mL). Organic phases were washed with brine (800 mL), pooled and dried with Na₂SO₄. The solvent phase was concentrated to a volume of ~100 mL, n-heptane (150 mL) was added and the solvent phase was concentrated again to ~100 mL. This was repeated twice. n-Heptane (100 mL) was added. The product precipitated upon stirring, was filtered off and dried to give the title compound as a white solid (18.4 g, quant.), LC-MS (UV peak area/ESI) ~100%, 332.029 (M+H)⁺.

Example E

Preparation of (6-chloro-4-iodo-5-cyclopropyl-methoxy-pyridin-2-yl)-methanol

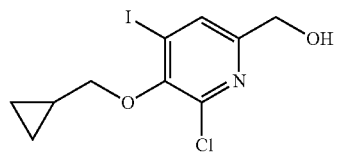 [SMILES: OCc1cc(I)c(OCC2CC2)c(Cl)n1]

The title compound was synthesized in analogy to Example A, using 6-chloro-5-hydroxy-4-iodo-2-pyridinemethanol and cyclopropylmethyl bromide as starting materials; LC-MS (UV peak area/ESI) 95.8%, 339.9584 (M+H)⁺.

Example F

Preparation of [6-Chloro-4-(4-chloro-phenyl)-5-cyclopropylmethoxy-pyridin-2-yl]-methanol

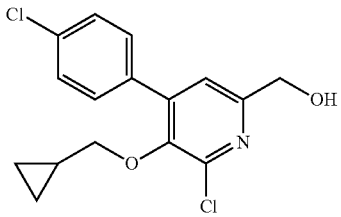 [SMILES: OCc1cc(-c2ccc(Cl)cc2)c(OCC2CC2)c(Cl)n1]

The title compound was synthesized in analogy to Example B, using 6-chloro-4-iodo-5-cyclopropylmethoxy-pyridin-2-yl)-methanol and 4-chlorophenyl-boronic acid as starting materials; LC-MS (UV peak area/ESI) 100%, 324.0551 (M+H)⁺.

Example G

Preparation of [4-(4-Chloro-phenyl)-5-cyclopropyl-methoxy-pyridin-2-yl]-methanol

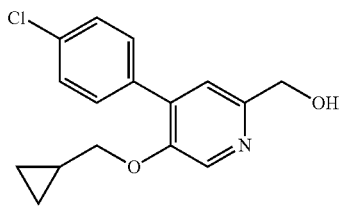 [SMILES: OCc1cc(-c2ccc(Cl)cc2)c(OCC2CC2)cn1]

The title compound was synthesized in analogy to Example C, using [6-chloro-4-(4-chloro-phenyl)-5-cyclopropylmethoxy-pyridin-2-yl]-methanol as starting material; LC-MS (UV peak area/ESI) 91.4%, 290.0933 (M+H)$^+$.

Example H

Preparation of 4-(4-chloro-phenyl)-5-cyclopropyl-methoxy-pyridine-2-carboxylic acid

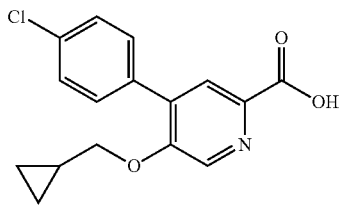 [SMILES: O=C(O)c1cc(-c2ccc(Cl)cc2)c(OCC2CC2)cn1]

The title compound was synthesized in analogy to Example D, using [4-(4-chloro-phenyl)-5-cyclopropyl-methoxy-pyridin-2-yl]-methanol as starting material; LC-MS (UV peak area/ESI)-%, 304.0742 (M+H)$^+$.

Example I

Preparation of 6-chloro-3-(2,2,2-trifluoro-ethoxy)-pyridazin-4-ylamine

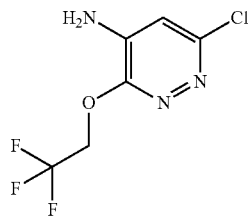 [SMILES: Nc1cc(Cl)nnc1OCC(F)(F)F]

To a solution of 3.28 g 3,6-dichloro-pyridazin-4-ylamine in 30 mL dimethylsulfoxide and 4.0 g trifluoroethanol was added 1.84 g lithium hydroxide hydrate and 3 mL water and the mixture was heated to 80° C. for 18 h. The reaction mixture was diluted with 100 mL water and stirred at ambient temperature for 2 h. The resulting solid was collected by filtration washed with water and dried to constant weight under high vacuum to yield 3.84 g of the title compound as off white crystals, MS 228.1 and 230.1 (M+H)$^+$.

Example J

Preparation of 4-bromo-6-chloro-3-(2,2,2-trifluoro-ethoxy)-pyridazine

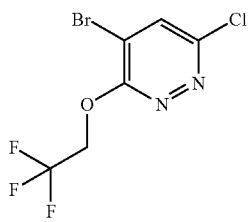 [SMILES: FC(F)(F)COc1nnc(Cl)cc1Br]

To a suspension of 2.30 g 6-chloro-3-(2,2,2-trifluoro-ethoxy)-pyridazin-4-ylamine in 23 mL dibromomethane was added 5.11 g isoamylnitrite at once and drop wise 4.642 g trimethylbromosilane at ambient temperature (during ca 10 min). A moderate exotherm was observed and a dark brown solution was obtained. The mixture was stirred at ambient temperature for 18 h. The solvents were evaporated and the residue was purified (3×) by chromatography on silica gel using a gradient of heptane to dichloromethane to yield 0.70 g of the title compound as white crystalline solid, MS 292 (M+H)$^+$.

Example K

Preparation of 6-chloro-4-(4-chloro-phenyl)-3-(2,2,2-trifluoro-ethoxy)-pyridazine

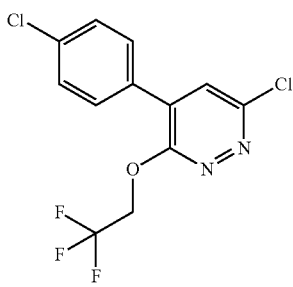 [SMILES: FC(F)(F)COc1nnc(Cl)cc1-c1ccc(Cl)cc1]

A mixture of 0.676 g 4-bromo-6-chloro-3-(2,2,2-trifluoro-ethoxy)-pyridazine, 363 mg 4-chlorophenylboronic acid, 641 mg potassium carbonate and 134 mg tetrakis(triphenylphosphine) palladium in 15 mL tetrahydrofuran and 15 mL water was heated to reflux for 18 h. The reaction mixture was partitioned between water and ethyl acetate. The phases were separated and the organic phase was purified by chromatography on silica gel using a gradient of heptane:ethyl acetate of 95:5 to 50:50 to yield 0.493 g of the title compound as white solid, MS 323.1 (M+H)$^+$.

Example L

Preparation of 5-(4-chloro-phenyl)-6-(2,2,2-trifluoro-ethoxy)-pyridazine-3-carboxylic acid methyl ester

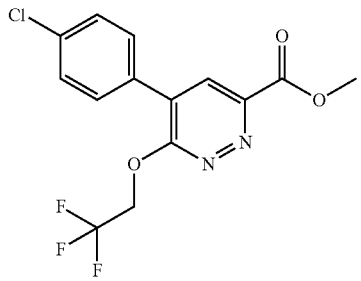 [SMILES: COC(=O)c1cc(-c2ccc(Cl)cc2)c(OCC(F)(F)F)nn1]

To a solution of 0.882 g 6-chloro-4-(4-chloro-phenyl)-3-(2,2,2-trifluoro-ethoxy)-pyridazine in methanol was added 0.626 g triethylamine and 0.081 g PdCl$_2$.dppf. CH$_2$Cl$_2$. The mixture was heated to 110° C. under an atmosphere of 70 bar carbon monoxide for 20 h. The reaction mixture was cooled to room temperature. The solids were removed by filtration and the mother liquor was evaporated and purified by chromatography on silica gel using a gradient of heptane:ethyl acetate of 95:5 to 50:50 to yield 0.870 g of the title compound as white solid, MS 347.1 (M+H)$^+$.

Example M

Preparation of 5-(4-chloro-phenyl)-6-(2,2,2-trifluoro-ethoxy)-pyridazine-3-carboxylic acid

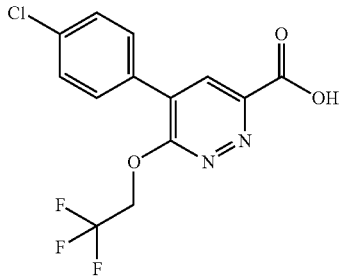 [SMILES: O=C(O)c1cc(-c2ccc(Cl)cc2)c(OCC(F)(F)F)nn1]

To a solution of 0.865 g 5-(4-chloro-phenyl)-6-(2,2,2-trifluoro-ethoxy)-pyridazine-3-carboxylic acid methyl ester in 9.0 mL tetrahydrofuran was added 3.2 mL of a 1M of lithium hydroxide in water was added and the mixture was stirred at ambient temperature for 3 h. The reaction mixture was acidified with 1M hydrochloric acid. The solid was collected by filtration washed with water and dried under high vacuum to yield 0.805 g of the title compound as white solid, 331.1 (M−H)$^−$.

Example N

Preparation of 3-chloro-6-cyclopropylmethoxy-pyridazine

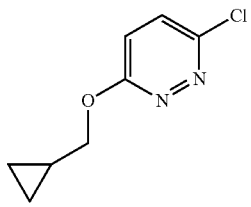 [SMILES: Clc1ccc(OCC2CC2)nn1]

To a solution of 1.016 mL cyclopropanemethanol in 10 mL dimethylsulfoxide was added 0.564 g sodium hydride 55% in mineral oil and the mixture was stirred at room temperature for 15 min. The resulting solution was added drop wise to a solution of 2.0 g 3,6-dichloropyridazine in 20 mL dry dimethylsulfoxide at room temperature and stirred at this temperature for 1 h. The reaction mixture was partitioned between water and ethyl acetate, the phases were separated and the organic phase was purified by chromatography on silica gel using a gradient of heptane:ethyl acetate=95:5 to 40:60 to yield 1.88 g of the title compound as white solid, MS 185.05 (M+H)$^+$.

Example O

Preparation of 6-chloro-3-cyclopropylmethoxy-4-iodo-pyridazine)

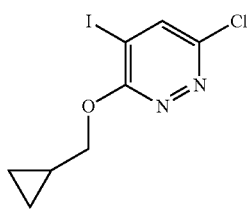 [SMILES: Clc1cc(I)c(OCC2CC2)nn1]

To a solution of 0.988 mL 2,2,6,6-tetramethylpiperidine in 10 mL tetrahydrofuran was added 3.534 mL of a 1.6M solution of n-butyl lithium in hexane at ambient temperature and the mixture was stirred at room temperature for 30 min. To this solution was added rapidly a pre-cooled (−75° C.) solution of 0.300 g 3-chloro-6-cyclopropylmethoxy-pyridazine in 10 mL tetrahydrofuran at −75° C. After 5 minutes, a pre-cooled solution of 0.701 g iodine in 10 mL THF was added rapidly. The reaction mixture was stirred at −75° C. for 30 minutes and then quenched with a saturated aqueous solution of ammonium chloride and diluted with ethyl acetate. The phases were separated and the organic phase was purified by chromatography on silica gel using a gradient of heptane: ethyl acetate=95:5 to 50:50 to yield 0.206 g of the title compound as light yellow solid, MS 310.9 (M+H)$^+$.

Example P

Preparation of 5-(4-chloro-phenyl)-6-cyclopropylmethoxy-pyridazine-3-carboxylic acid

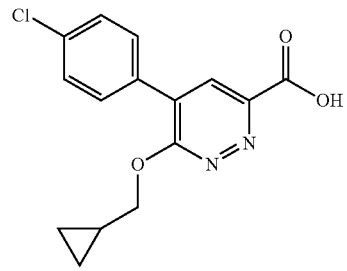 [SMILES: O=C(O)c1cc(-c2ccc(Cl)cc2)c(OCC2CC2)nn1]

The title compound was synthesized in analogy to examples J to M by substituting 4-bromo-6-chloro-3-(2,2,2-trifluoro-ethoxy)-pyridazine with 6-chloro-3-cyclopropylmethoxy-4-iodo-pyridazine the title compound was obtained as white solid, MS 303.1 (M−H)$^−$.

Example Q

Preparation of 2-chloro-4-(4-chloro-phenyl)-5-fluoro-pyrimidine

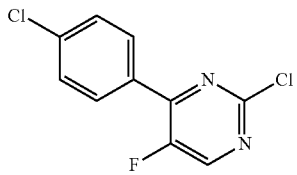 [SMILES: Fc1cnc(Cl)nc1-c1ccc(Cl)cc1]

A mixture of 5.0 g 2,4-dichloro-5-fluoropyrimidine, 4.683 g p-chlorophenylboronic acid, 1.730 g tetrakistriphenylphosphinpalladium and 8.278 g potassium carbonate in 125 mL tetrahydrofuran and 125 mL water was heated to reflux for 3 h. The reaction mixture was cooled to room temperature and diluted with ethyl acetate. The phases were separated and the organic phase was washed with brine dried over sodium sulfate and evaporated. The solid residue was triturated in ca 60 mL methanol for 30 min. The solids were collected by filtration to yield 5.2 g of an off white solid (contains some boronic acid which gives a start spot). The mother liquor was evaporated and the residue was purified by chromatography on silica gel with heptane:ethyl acetate=8:2 to 1:1 to yield 1.0 g of the product as white solid. Both crops were combined and dissolved in ca 50 mL dichloromethane and filtered over ca 50 g silica gel with dichloromethane to remove a polar start spot. The filtrate was concentrated under aspirator vacuum whereby precipitation occurred. The solid was collected by filtration to yield 5.76 g of the title compound as white crystals, MS 230.1 and 228.1 (M+H)$^+$.

Example R

Preparation of 2-chloro-4-(4-chloro-phenyl)-5-cyclopropylmethoxy-pyrimidine

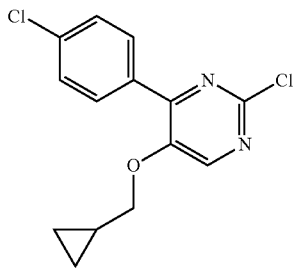 [SMILES: Clc1ccc(-c2nc(Cl)ncc2OCC2CC2)cc1]

To a solution of 0.948 mL cyclopropanemethanol in 13 mL dimethylformamide was added 0.468 g sodium hydride 55% in mineral oil and the reaction mixture was stirred at room temperature for 15 min. The resulting solution was added drop wise to a solution of 2.586 g 2-chloro-4-(4-chloro-phenyl)-5-fluoro-pyrimidine at 0° C. and the mixture was stirred at 0° C. for 30 min. The reaction mixture was partitioned between water and ethyl acetate. The phases were separated and the organic phase was purified by chromatography on silica gel using a gradient of heptane:ethyl acetate=10:90 to 80:20 to yield 2.50 g of the title compound as white solid, MS 295.2 (M+H)$^+$.

Example S

Preparation of 4-(4-chloro-phenyl)-5-cyclopropyl-methoxy-pyrimidine-2-carboxylic acid methyl ester

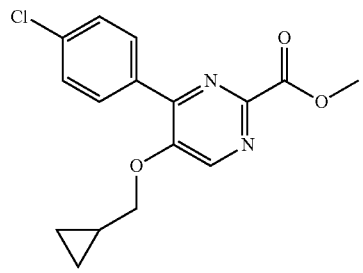 [SMILES: COC(=O)c1ncc(OCC2CC2)c(-c2ccc(Cl)cc2)n1]

The title compound was synthesized in analogy to example L by substituting 6-chloro-4-(4-chloro-phenyl)-3-(2,2,2-trifluoro-ethoxy)-pyridazine with 2-chloro-4-(4-chloro-phenyl)-5-cyclopropylmethoxy-pyrimidine the title compound was obtained as white solid, MS 319.2 (M+H)$^+$.

Example T

Preparation of 4-(4-chloro-phenyl)-5-cyclopropyl-methoxy-pyrimidine-2-carboxylic acid

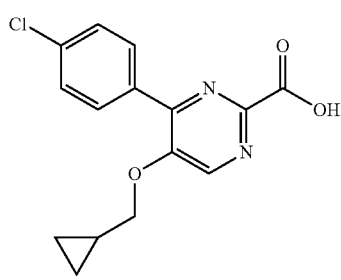 [SMILES: O=C(O)c1ncc(OCC2CC2)c(-c2ccc(Cl)cc2)n1]

To a solution of 2.655 g 4-(4-chloro-phenyl)-5-cyclopropylmethoxy-pyrimidine-2-carboxylic acid methyl ester in 27 mL tetrahydrofuran was added 11 mL of a 1M solution of lithium hydroxide in water and the mixture was stirred at room temperature for 1 h. The reaction mixture was acidified by addition of 1M hydrochloric acid. The precipitate was collected by filtration washed with water and dried to constant weight under high vacuum to yield 2.473 g of the title compound as white solid, MS 305.1 (M+H)$^+$.

Example U

Preparation of 4-(4-Chloro-phenyl)-5-fluoro-pyrimidine-2-carboxylic acid methyl ester

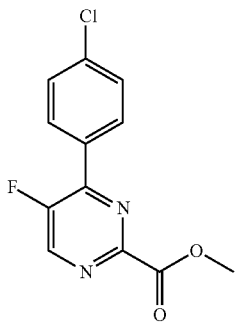 [SMILES: COC(=O)c1ncc(F)c(-c2ccc(Cl)cc2)n1]

To a solution of 0.200 g 2-chloro-4-(4-chloro-phenyl)-5-fluoro-pyrimidine was in 2 ml methanol was added 0.020 g PdCl$_2$.dppf.CH$_2$Cl$_2$ and 0.176 g triethylamine and the mixture was stirred under an atmosphere of 70 bar carbon monoxide at 130° C. for 20 hours. The solids were removed by filtration and the mother liquor was purified by chromatography on silica gel with a gradient of heptane:ethyl acetate=8:2 to ethyl acetate to yield 0.032 g (14.58%) of the title compound as off-white solid, MS 267.1 (M+H)$^+$.

Example V

Preparation of 4-(4-Chloro-phenyl)-5-(2,2,2-trifluoro-ethoxy)-pyrimidine-2-carboxylic acid methyl ester

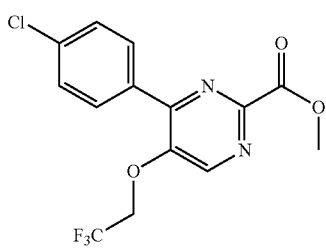 [SMILES: COC(=O)c1ncc(OCC(F)(F)F)c(-c2ccc(Cl)cc2)n1]

To a solution of 0.143 g 4-(4-chloro-phenyl)-5-fluoro-pyrimidine-2-carboxylic acid methyl ester in 1.5 ml dried DMSO was added 192 mg of cesium carbonate and 0.059 g of 2,2,2-trifluoroethanol and the mixture was stirred at 60° C. for 2 hours. The reaction mixture was partitioned between water and ethyl acetate, the phases were separated and the organic phase was dried with MgSO$_4$ and purified by chromatography on silica gel with a gradient of heptane:ethyl acetate=9:1 to 1:1 to yield 161 mg (86.60%) of the title compound as white solid, MS 347.1 (M+H)$^+$.

Example W

Preparation of 4-(4-Chloro-phenyl)-5-(2,2,2-trifluoro-ethoxy)-pyrimidine-2-carboxylic acid

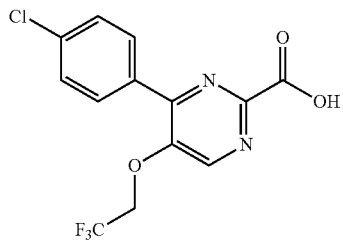 [SMILES: O=C(O)c1ncc(OCC(F)(F)F)c(-c2ccc(Cl)cc2)n1]

To a solution of 4-(4-chloro-phenyl)-5-(2,2,2-trifluoro-ethoxy)-pyrimidine-2-carboxylic acid methyl ester in 2.5 ml THF was added 937 μL of a 1M LiOH solution in water and the reaction mixture was stirred at room temperature for 30 minutes. The reaction mixture was acidified with 1M hydrochloric acid solution and the formed precipitate was collected by filtration washed with water and dried under high vacuum to yield 232 mg (96.71%) of the title compound as white solid, MS 331.1 (M+H)$^+$.

Example X

Preparation of 2-Chloro-4-(3,4-dichloro-phenyl)-5-fluoro-pyrimidine

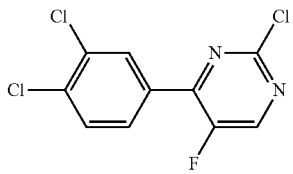 [SMILES: Fc1cnc(Cl)nc1-c1ccc(Cl)c(Cl)c1]

A mixture of 20 g 2,4-dichloro-5-fluoropyrimidine, 22.86 g 3,4-dichlorophenylboronic acid, 33.11 g potassium carbonate and 6.92 g tetrakis(triphenylphosphine)palladium were in 500 mL THF and 500 mL water was heated to reflux for 4 h. The reaction mixture was cooled to room temperature diluted with water and ethyl acetate. The phases were separated and the organic phase was purified by chromatography on silica gel with dichloromethane to yield 24.640 g (74.13%) of the title compound as white solid, MS 279.1 (M+H)$^+$.

Example Y

Preparation of 2-Chloro-4-(3,4-dichloro-phenyl)-5-(2,2,2-trifluoro-ethoxy)-pyrimidine

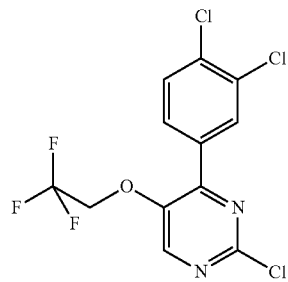 [SMILES: FC(F)(F)COc1cnc(Cl)nc1-c1ccc(Cl)c(Cl)c1]

To a mixture of 2.0 ml 2,2,2-trifluoroethanol in 35 mL dry DMF was added 1.1 g sodium hydride was added and the mixture was stirred at room temperature for 15 minutes. The resulting solution was added dropwise at −10° C. to a solution of 7 g 2-chloro-4-(3,4-dichloro-phenyl)-5-fluoro-pyrimidine in 50 mL dry DMF during 39 min. The reaction mixture was then stirred at room temperature for 2 h. The resulting brown mixture was partitioned between water and ethyl acetate, the phases were separated the organic phase was dried over MgSO$_4$ and purified by chromatography on silica gel with a gradient of heptane:dichloromethane=1:1 to dichloromethane to yield 5.575 g (61.81%) of the title compound as light yellow solid, MS 356.9 (M+H)$^+$.

Example Z

Preparation of 4-(3,4-Dichloro-phenyl)-5-(2,2,2-trifluoro-ethoxy)-pyrimidine-2-carboxylic acid methyl ester

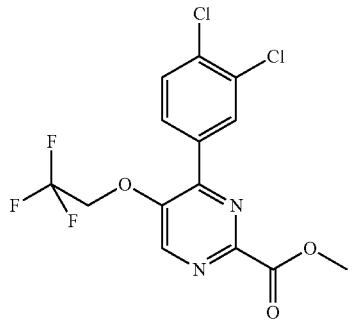 [SMILES: COC(=O)c1ncc(OCC(F)(F)F)c(-c2ccc(Cl)c(Cl)c2)n1]

To a solution of 5.470 g 2-chloro-4-(3,4-dichloro-phenyl)-5-(2,2,2-trifluoro-ethoxy)-pyrimidine was dissolved in 100 mL methanol was added 1.093 g PdCl$_2$.dppf.CH$_2$Cl$_2$ and 3.096 g triethylamine and the mixture was stirred under an atmosphere of 70 bar carbon monoxide at 110° C. for 20 hours. The solids were removed by filtration and the mother liquor was purified by chromatography on silica gel with a gradient of heptane:ethyl acetate=9:1 to 1:1 to yield 4.49 g (60.45%) of the title compound as white solid, MS 382.2 (M+H)$^+$.

Example AA

Preparation of 4-(3,4-Dichloro-phenyl)-5-(2,2,2-trifluoro-ethoxy)-pyrimidine-2-carboxylic acid

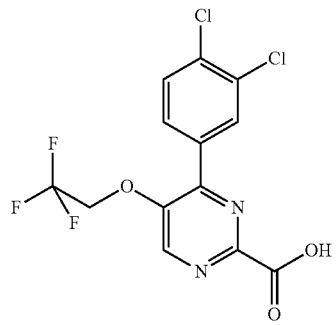 [SMILES: O=C(O)c1ncc(OCC(F)(F)F)c(-c2ccc(Cl)c(Cl)c2)n1]

To a solution of 3.79 g 4-(3,4-dichloro-phenyl)-5-(2,2,2-trifluoro-ethoxy)-pyrimidine-2-carboxylic acid methyl ester in 28 mL tetrahydrofuran was added 13 mL of a 1M solution of lithium hydroxide in water and the mixture was stirred at room temperature for 1 h. The reaction mixture was acidified by addition of 1M hydrochloric acid. The precipitate was collected by filtration washed with water and dried to constant weight under high vacuum to yield 3.561 g (97.55%) of the title compound as white solid, MS 365.0 (M−H)$^-$.

Example AB

Preparation of 6-Chloro-2-(4-chloro-phenyl)-3-(2,2,2-trifluoro-ethoxy)-pyridine

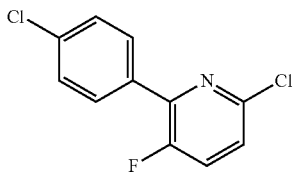 [SMILES: Fc1ccc(Cl)nc1-c1ccc(Cl)cc1]

A solution of 2.2 g 2,4-chloro-5-fluoropyridine, 2.28 g 4-chlorophenylboronic acid and 0.6 g tetrakistriphenylphosphinpalladium in 30 mL tetrahydrofuran was added 30 mL of a 10% a solution of potassium carbonate in water and the mixture was stirred at ambient temperature for 18 h. The reaction mixture was diluted with ethyl acetate and water. The phases were separated and the organic phase was washed water, 10% aqueous citric acid, 10% aqueous sodium bicarbonate and brine, dried over sodium sulfate and evaporated. The residue was purified by chromatography on silica gel with a gradient of heptane:dichloromethane=9:1 to 1:1 (only starting spot was removed) The product fractions were collected and evaporated. The residue was subjected to kugelrohr distillation at 0.03 mBar and 110° C. to yield 1.72 g of the title compound as colorless oil which solidified into white crystals, MS 241 and 243 (M+H)$^+$.

Example AC

Preparation of 6-Chloro-2-(4-chloro-phenyl)-3-(2,2,2-trifluoro-ethoxy)-pyridine

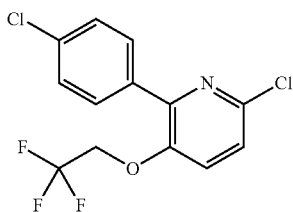 [SMILES: FC(F)(F)COc1ccc(Cl)nc1-c1ccc(Cl)cc1]

To a solution of 1.273 g trifluoroethanol in 20 mL dimethylsulfoxide was added 0.463 g sodiumhydride 55% in oil and the mixture was stirred at room temperature for 15 min. To the resulting solution was added a solution of 3.2 g 6-chloro-2-(4-chloro-phenyl)-3-(2,2,2-trifluoro-ethoxy)-pyridine in 10 mL dimethylsulfoxide and the mixture was stirred at room temperature for 3 h. The reaction mixture was partitioned between water and ethyl acetate. The phases were separated and the organic phase was purified by chromatography on silica gel with a gradient of heptane to dichloromethane to yield 3.30 g of the title compound as slightly yellow solid, at 322.1 and 324.2 (M+H)$^+$. The product was obtained as 85:15 mixture of F vs Cl substitution products that were better separable at the next step.

Example AD

Preparation of 6-(4-Chloro-phenyl)-5-(2,2,2-trifluoro-ethoxy)-pyridine-2-carboxylic acid methyl ester

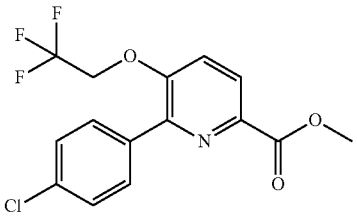 [SMILES: COC(=O)c1ccc(OCC(F)(F)F)c(-c2ccc(Cl)cc2)n1]

To a solution of 3.30 g 6-chloro-2-(4-chloro-phenyl)-3-(2,2,2-trifluoro-ethoxy)-pyridine was in 100 mL methanol was added 0.8 g PdCl$_2$.dppf.CH$_2$Cl$_2$ and 2.5 g triethylamine and the mixture was stirred under an atmosphere of 70 bar carbon monoxide at 110° C. for 20 hours. The solids were removed by filtration and the mother liquor was purified by chromatography on silica gel with a gradient of heptane:ethyl acetate=9:1 to 1:1 to yield ca 3 g of the title compound as white solid, MS 346.2 (M+H)$^+$.

Example AE

Preparation of 6-(4-Chloro-phenyl)-5-(2,2,2-trifluoro-ethoxy)-pyridine-2-carboxylic acid

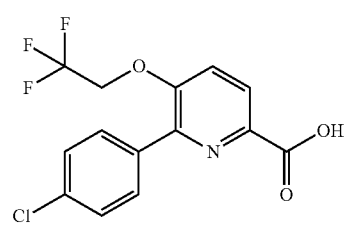 [SMILES: O=C(O)c1ccc(OCC(F)(F)F)c(-c2ccc(Cl)cc2)n1]

To a solution of 3.0 g 6-(4-chloro-phenyl)-5-(2,2,2-trifluoro-ethoxy)-pyridine-2-carboxylic acid methyl ester in 30 mL tetrahydrofuran was added 14 mL of a 1M solution of lithium hydroxide in water and the mixture was stirred at room temperature for 1 h. The reaction mixture was acidified by addition of 1M hydrochloric acid. The precipitate was collected by filtration washed with water and dried to constant weight under high vacuum to yield 2.36 g of the title compound as white solid, MS 330.3 (M−H)$^-$.

Example AF

Preparation of 5-(4-Chloro-phenyl)-6-((S)-2,2,2-trifluoro-1-methyl-ethoxy)-pyridazine-3-carboxylic acid

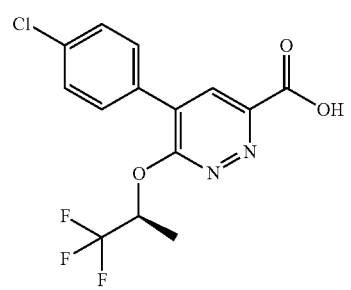 [SMILES: C[C@H](Oc1nnc(C(=O)O)cc1-c1ccc(Cl)cc1)C(F)(F)F]

The compound was prepared in analogy to Examples I to M by substituting trifluoroethanol with (S)-1,1,1-trifluoro-propan-2-ol in the etherification step. The title compound was obtained as off-white foam, MS 345.1 (M−H)$^-$.

Example AG

Preparation of (S)-methyl 6-(4-chlorophenyl)-5-(1,1,1-trifluoropropan-2-yloxy)pyrazine-2-carboxylate

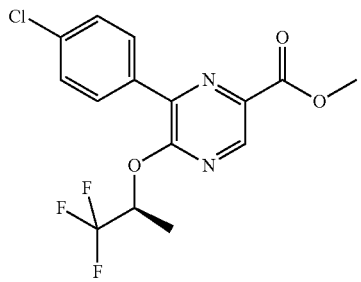 [SMILES: COC(=O)c1cnc(O[C@@H](C)C(F)(F)F)c(-c2ccc(Cl)cc2)n1]

To a solution of methyl 5-bromo-6-(4-chlorophenyl)pyrazine-2-carboxylate (0.847 g, 2.59 mmol, Eq: 1.00) in dry DMSO (8 ml) was added cesium carbonate (1.54 g, 2.84 mmol, Eq: 1.1) and (S)-1,1,1-trifluoro-2-propanol (324 mg, 233 μl, 2.84 mmol, Eq: 1.1) and the reaction mixture was stirred at room temperature for 3 hours. The reaction mixture was partitioned between water and ethyl acetate, the phases were separated and the organic phase was dried over MgSO$_4$ evaporated and purified by flash chromatography (silica gel, 100 g, 10% to 50% EtOAc in heptane) to yield the title compound as light yellow oil (0.724 g, 77.6%), MS 361.1 (M+H)$^+$.

Example AH (S)-6-(4-chlorophenyl)-5-(1,1,1-trifluoropropan-2-yloxy)pyrazine-2-carboxylic acid

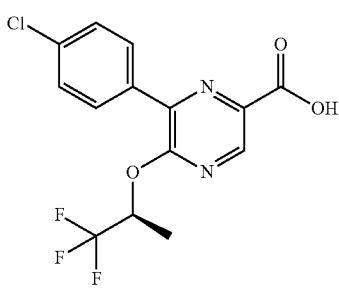 [SMILES: C[C@H](Oc1ncc(C(=O)O)nc1-c1ccc(Cl)cc1)C(F)(F)F]

To a suspension of (S)-methyl 6-(4-chlorophenyl)-5-(1,1,1-trifluoropropan-2-yloxy)pyrazine-2-carboxylate (0.72 g, 2.00 mmol, Eq: 1.00) in tetrahydrofuran (7 mL) was added a 1M LiOH solution in water (2.59 ml, 2.59 mmol, Eq: 1.3) and the reaction mixture was stirred at room temperature for 1 hour. The mixture was concentrated to remove tetrahydrofuran and diluted with water; acidified with 1M hydrochloric acid to pH 2 and extracted with ethyl acetate. The organic phase was dried with MgSO$_4$; filtered, evaporated and dried to constant weight under high vacuum to yield the title compound as white solid (0.70 g, 100%), MS 345.0 (M−H)$^-$.

Example AI

Preparation of C-(5-Trifluoromethyl-[1,2,4]oxadiazol-3-yl)-methylamine hydrochloride

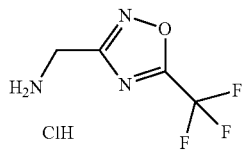 [SMILES: NCc1noc(C(F)(F)F)n1 ; Cl]

To a solution of 1.89 g (N-hydroxycarbamimidoylmethyl)-carbamic acid tert-butyl ester in 20 mL acetonitrile was added 7.746 g Huenig's base and 6.294 g trifluoroacetic acid anhydride (exotherm) and the mixture was stirred at room temperature for 2 h. The reaction mixture was partitioned between 10% citric acid and ethyl acetate. The phases were separated and the organic phase was washed with 10% sodium bicarbonate and brine dried over magnesium sulfate and evaporated. The residue was dried under high vacuum and purified by chromatography on silica gel with a gradient of heptane:ethyl acetate=9:1 to 1:1. The product fraction were combined and concentrated whereby crystallization occurred. The solid was collected by filtration and dried to constant weight to yield 1.00 g white crystals. These were dissolved up in 3 mL of a 4M solution of hydrochloric acid in dioxane and the mixture was stirred at ambient temperature for 18 h. The formed solid was collected by filtration washed with ethyl acetate and dried to constant weight to yield 0.43 g of the title compound as white crystals, MS 166.0 (M–H)⁻.

Example AJ

Preparation of (3-Trifluoromethyl-[1,2,4]oxadiazol-5-ylmethyl)-carbamic acid tert-butyl ester

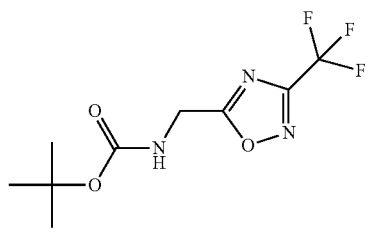 [SMILES: CC(C)(C)OC(=O)NCc1nc(C(F)(F)F)no1]

To a solution of 0.821 g Boc-glycine in 8 ml dichloromethane was added 0.967 g dicyclohexylcarbodiimide and the mixture was stirred at room temperature for 30 min. To the resulting white suspension was added a solution of 0.60 g 2,2,2-trifluoro-N-hydroxy-acetamidine in 6 ml dichloromethane (an almost clear solution is obtained initially and a white precipitate forms after ca 5 min) and the mixture was stirred at room temperature for 2 h. The solid was removed by filtration and the mother liquor was purified by chromatography on silica gel with a gradient of heptane:ethyl acetate=8:2 to ethyl acetate to yield 0.66 g white crystals. A mixture of 0.57 g of these crystals in 10 ml toluene was heated under a dean stark trap to reflux for 5 h. The solvent was evaporated and the residue was purified by chromatography on silica gel with a gradient of heptane:ethyl acetate=9:1 to 1:1 to yield 0.29 g of the title compound as colorless oil, MS 266.2 (M–H)⁻.

Example AK

Preparation of 3-Trifluoromethyl-[1,2,4]oxadiazol-5-methanamine hydrochloride

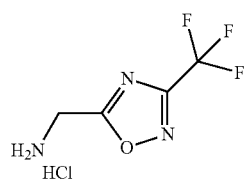 [SMILES: NCc1nc(C(F)(F)F)no1 ; Cl]

To a solution of 0.29 g (3-trifluoromethyl-[1,2,4]oxadiazol-5-ylmethyl)-carbamic acid tert-butyl ester in 3 ml ethyl acetate was added 1.5 ml of a 4M solution of hydrochloric acid in dioxane and the mixture was stirred at ambient temperature for 18 h. The resulting clear solution was evaporated and the residue was triturated under ethyl acetate. The solid was collected by filtration and dried to constant weight under high vacuum to yield 0.145 g of the title compound as white crystals, 169.2 (M+H)⁺.

Example AL

Preparation of 5-Chloro-3-(4-chloro-phenyl)-2-fluoro-pyridine

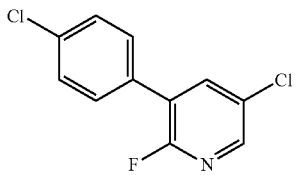 [SMILES: Fc1ncc(Cl)cc1-c1ccc(Cl)cc1]

In analogy to Example K by substituting 4-bromo-6-chloro-3-(2,2,2-trifluoro-ethoxy)-pyridazine with 3-bromo-5-chloro-2-fluoropyridine in the Suzuki step the title compound was obtained as white solid, 241 (M+H)⁺.

Example AM

Preparation of 5-Chloro-3-(4-chloro-phenyl)-2-(S)-2,2,2-trifluoro-1-methyl-ethoxy)-pyridine

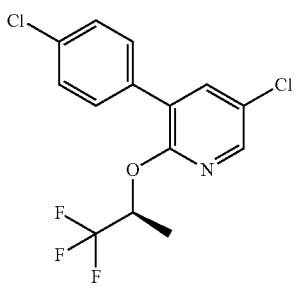 [SMILES: C[C@H](Oc1ncc(Cl)cc1-c1ccc(Cl)cc1)C(F)(F)F]

To a mixture of 1.133 g (S)-1,1,1-trifluor-2-propanol in 10 ml dry DMF 397 mg sodium hydride (60%) was added and the mixture was stirred at room temperature for 30 minutes. The resulting solution was added dropwise at RT to a solution of 2.185 g 5-chloro-3-(4-chloro-phenyl)-2-fluoro-pyridine in 20 ml dry DMF. The reaction mixture was then stirred at room temperature for 2 h. The resulting light yellow mixture was partitioned between water and ethyl acetate, the phases were separated. The organic phase was dried over MgSO4 and purified by chromatography on silica gel with a gradient of heptane to heptane:ethyl acetate=9:1 to yield 2.330 g (76.80%) of the title compound as colorless liquid, 336.1 (M+H)$^+$.

Example AN

Preparation of (S)-methyl 5-(4-chlorophenyl)-6-(1,1,1-trifluoropropan-2-yloxy)nicotinate

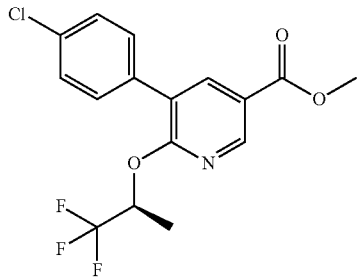 [SMILES: COC(=O)c1cnc(O[C@@H](C)C(F)(F)F)c(-c2ccc(Cl)cc2)c1]

To a solution of 2.42 g 5-chloro-3-(4-chloro-phenyl)-2-((S)-2,2,2-trifluoro-1-methyl-ethoxy)-pyridine in 50 mL methanol was added 1.09 g triethylamine and 0.484 g PdCl$_2$.dppf.CH$_2$Cl$_2$. The mixture was heated to 150° C. under an atmosphere of 70 bar carbon monoxide for 20 h. The reaction mixture was cooled to room temperature. The solids were removed by filtration and the mother liquor was evaporated and purified by chromatography on silica gel using a gradient of heptane to heptane:ethyl acetate 85:15 to yield 0.862 g (33%) of the title compound as a light yellow oil, 359 (M).

Example AO

Preparation of (S)-5-(4-Chlorophenyl)-6-(1,1,1-trifluoropropan-2-yloxy)nicotinic acid

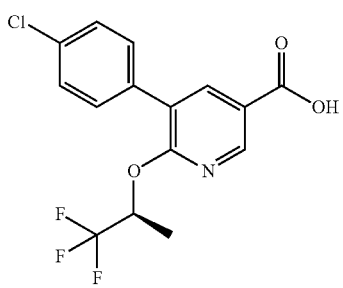 [SMILES: C[C@H](Oc1ncc(C(=O)O)cc1-c1ccc(Cl)cc1)C(F)(F)F]

To a solution of 0.860 g (S)-methyl 5-(4-chlorophenyl)-6-(1,1,1-trifluoropropan-2-yloxy)nicotinate in 9 mL tetrahydrofuran was added 3 mL of a 1M solution of lithium hydroxide in water and the mixture was stirred at room temperature overnight. The solvent was evaporated and the residue was acidified by addition of 1M hydrochloric acid till pH=2. Ethyl acetate was added and the phases were separated. The organic phase was dried over MgSO$_4$ and the solvent was removed to yield 830 mg (100%) of the title compound as light yellow solid, MS 344.1 (M−H)$^−$.

Example AP

Preparation of (S)-Methyl 4-(4-chlorophenyl)-5-(1,1,1-trifluoropropan-2-yloxy)pyrimidine-2-carboxylate

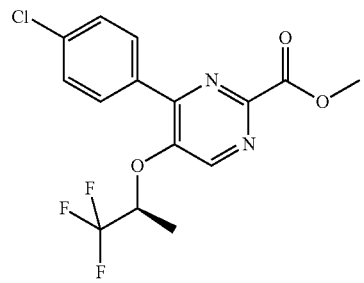 [SMILES: COC(=O)c1ncc(O[C@@H](C)C(F)(F)F)c(-c2ccc(Cl)cc2)n1]

The compound was prepared in analogy to examples R and S by substituting cyclopropanemethanol with (S)-1,1,1-trifluor-2-propanol and 2-chloro-4-(4-chloro-phenyl)-5-fluoro-pyrimidine with 2-chloro-4-(4-chloro-phenyl)-5-fluoro-pyrimidine. The title compound was obtained as white solid, MS 361.2 (M+H)$^+$.

Example AQ

Preparation of (S)-4-(4-Chlorophenyl)-5-(1,1,1-trifluoropropan-2-yloxy)pyrimidine-2-carboxylic acid

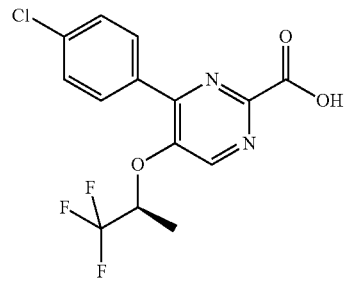 [SMILES: C[C@H](Oc1cnc(C(=O)O)nc1-c1ccc(Cl)cc1)C(F)(F)F]

The title compound was obtained in analogy to Example AO by substituting (S)-methyl 5-(4-chlorophenyl)-6-(1,1,1-trifluoropropan-2-yloxy)nicotinate with (S)-methyl 4-(4-chlorophenyl)-5-(1,1,1-trifluoropropan-2-yloxy)pyrimidine-2-carboxylate as white solid, MS 345.0 (M−H)$^−$.

Example AR

Preparation of (S)-4-(4-Chlorophenyl)-5-(1,1,1-trifluoropropan-2-yloxy)picolinic acid

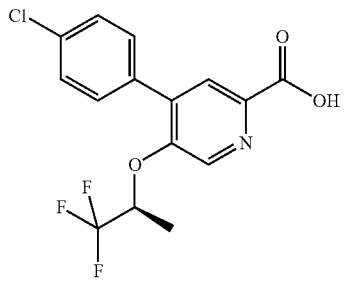 [SMILES: C[C@H](Oc1cnc(C(=O)O)cc1-c1ccc(Cl)cc1)C(F)(F)F]

The title compound was obtained in analogy to Examples AL to AO by substituting 3-bromo-5-chloro-2-fluoropyridine with 2-chloro-5-fluoro-4-iodopyridine in the Suzuki coupling as a white solid, MS 344.1 (M−H)⁻.

Example AS

Preparation of 2-(4-Chloro-phenyl)-3-fluoro-pyridine

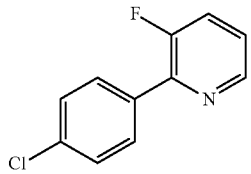 [SMILES: Fc1cccnc1-c1ccc(Cl)cc1]

A solution of 18.60 g 2-chloro-3-fluoropyridine, 23.25 g 4-chlorophenylboronic acid and 2.30 g 1,1'bis(diphenylphosphino)ferrocenedichloropalladium(II), 22.50 g sodium carbonate in toluol:dimethylformamide:water 190:20:40 and the mixture was stirred at 90° C. over 5 hours. The reaction mixture was diluted with ethyl acetate and water. The phases were separated and the organic phase was washed with brine, dried over magnesium sulfate and evaporated. The residue was purified by chromatography on silica gel with a gradient of heptane to heptane:ethyl acetate 1:1. The product fractions were collected and evaporated. The residue was crystallized in ether to yield 19.30 g (65.73%) of the title compound as off-white solid, MS 208.1 (M+H)⁺.

Example AT

Preparation of 2-(4-Chloro-phenyl)-3-cyclopropylmethoxy-pyridine

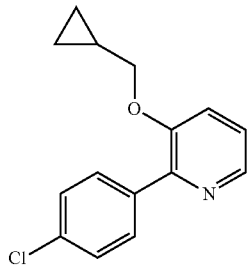 [SMILES: Clc1ccc(-c2ncccc2OCC2CC2)cc1]

To a mixture of 16.20 g cyclopropanmethanol in 150 ml dry DMSO 11 g sodium hydride (55%) was added and the mixture was stirred at room temperature for 30 minutes. A solution containing 37.30 g 2-(4-chloro-phenyl)-3-fluoro-pyridine in 50 mL dry DMSO was added dropwise. The reaction mixture was then stirred at room temperature for 3 h. The resulting suspension was partitioned between water and methylene chloride, the phases were separated. The organic phase was washed with brine; then dried over MgSO₄ and purified by chromatography on silica gel with a gradient of heptane to heptane:ethylacetate=2:1 to yield 34.95 g (74.90%) of the title compound as yellow oil, MS 260.1 (M+H)⁺.

Example AU

Preparation of 2-(4-Chloro-phenyl)-3-cyclopropylmethoxy-pyridine 1-oxide

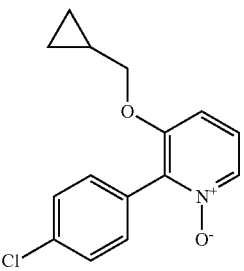 [SMILES: [O-][n+]1cccc(OCC2CC2)c1-c1ccc(Cl)cc1]

To a solution of 5 g 2-(4-chloro-phenyl)-3-cyclopropylmethoxy-pyridine in 15 mL acetic acid, 3 mL hydrogenperoxyde (30% in water) was added. The reaction mixture was then stirred at 70° C. for 15 h. The reaction mixture was diluted with water and quenched with sodium carbonate. The mixture was washed with methylene chloride. The organic phase was washed with water; then dried over MgSO₄ and purified by chromatography on silica gel with a gradient of ethyl acetate to ethyl acetate:methanol 4:1 to yield 3.46 g (65.19%) of the title compound as white solid, MS 276.1 (M+H)⁺.

Example AV

Preparation of 6-(4-Chloro-phenyl)-5-cyclopropylmethoxy-pyridine-2-carbonitrile

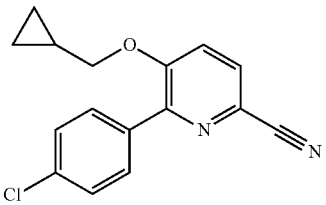 [SMILES: N#Cc1ccc(OCC2CC2)c(-c2ccc(Cl)cc2)n1]

To a solution of 25 g 2-(4-chloro-phenyl)-3-cyclopropylmethoxy-pyridine 1-oxide in 500 mL acetonitrile, 9.23 g triethylamine and 10.73 g dimethylcarbamoylchlorid were added. After 5 minutes at room temperature, 27.88 g trimethylsilylcyanid was added. The reaction mixture was stirred at 90° C. over 15 h. The reaction mixture was partitioned between water and ethyl acetate; then extracted. The organic phase was washed with brine; then dried over MgSO₄ and purified by chromatography on silica gel with a gradient of heptane to heptane:ethyl acetate 2:1 to yield 15.30 g (59.26%) of the title compound as light yellow solid, MS 285.1 (M+H)⁺.

Example AW

Preparation of 6-(4-Chloro-phenyl)-5-cyclopropyl-methoxy-pyridine-2-carboxylic acid

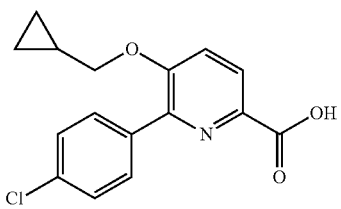 [SMILES: O=C(O)c1ccc(OCC2CC2)c(-c2ccc(Cl)cc2)n1]

8.27 g acetylchloride was added dropwise to 120 mL ethanol at 0° C. After 5 minutes, 6 g 6-(4-chloro-phenyl)-5-cyclopropylmethoxy-pyridine-2-carbonitrile was added at 0° C. The reaction mixture was stirred at 90° C. over 20 h. The reaction mixture was partitioned between water and ethyl acetate; then extracted. The organic phase was washed with brine; then dried over $MgSO_4$. The crude product was stirred at room temperature in tetrahydrofuran:water 45:20. 1.77 g lithium hydroxide was added. The reaction mixture was stirred at 80° C. over 7 hours. The reaction mixture was added over acetic acid and extracted with dichloromethane. The organic phase was washed with water; then dried over $MgSO_4$ and purified by chromatography on silica gel with a gradient of heptane to heptane:ethyl acetate 2:1 to yield 4.50 g (70.31%) of the title compound as light yellow solid, MS 304.1 $(M+H)^+$.

Example AX

Preparation of 5-(tert-Butyldimethylsilyloxy)-1,1,1-trifluoropent-3-yn-2-one

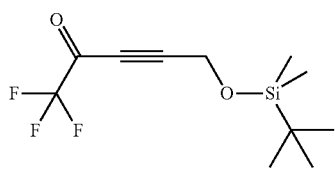 [SMILES: CC(C)(C)[Si](C)(C)OCC#CC(=O)C(F)(F)F]

To 50 mL of a 1.6M solution of n-BuLi (0.080 mol, 1 equ) in hexanes was added dropwise tert-butyldimethyl(prop-2-ynyloxy)silane (13.57 g; 0.080 mol; 1 equ) with dry ice acetone cooling. After addition the dry ice acetone bath was replaced by an ice acetone bath. When the mixture became difficult to stir toluene (25 mL) was added. The mixture became clear and was stirred at −10° C. for 15 min. To the resulting slightly yellow solution was added ethyl 2,2,2-trifluoroacetate (11.3 g; 0.080 mol; 1 equ) with cooling in a dry ice acetone bath (ca<−40° C.). After addition the dry ice acetone bath was replaced by an ice acetone bath and the mixture was stirred with thawing to room temperature for 18 h. The reaction mixture was poured onto ice mixed with 10% aqueous citric acid. The phases were separated and the organic phase was washed with 10% aqueous sodium bicarbonate and brine and purified by filtration over ca 350 g silica gel using heptane:dichloromethane=1:1 as eluent. The product fractions (dichloromethane:heptane 1:1; r.f.:0.3 KMnO4 staining) were pooled and evaporated to yield the title compound as an orange yellow oil (16.0 g, 75.4% Th), MS 266.277 $(M)^+$.

Example AY

Preparation of (3-(Trifluoromethyl)isoxazol-5-yl)methanol

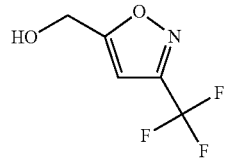 [SMILES: OCc1cc(C(F)(F)F)no1]

To a solution of hydroxylamine hydrochloride (0.694 g 0.010 mol, 1 equ) and 0.02 g sodium hydroxide in 25 mL methanol was added 5-(tert-butyldimethylsilyloxy)-1,1,1-trifluoropent-3-yn-2-one (2.66 g 0.010 mol, 1 equ) and the mixture was heated to reflux for 3 h. The reaction mixture was extracted with ethyl acetate and purified by chromatography on silica gel (50 g) using a gradient of heptane:ethyl acetate=9:1 to 1:1. to yield 0.524 g of the title compound as colorless oil, MS 167$(M)^+$.

Example AZ

Preparation of 5-(Bromomethyl)-3-(trifluoromethyl)isoxazole

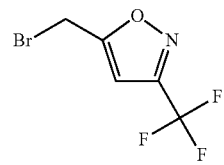 [SMILES: FC(F)(F)c1cc(CBr)on1]

To a solution of (3-(trifluoromethyl)isoxazol-5-yl)methanol (2.5 g, 15 mmol) in dimethylformamide (25 mL) was added drop wise tribromophosphine (4.64 g 17.1 mmol, 1.15 eq) and the mixture was stirred at 0° C. for 15 min and at ambient temperature for 2 h. The reaction mixture was partitioned between 10% sodium bicarbonate and dichloromethane. The phases were separated and the organic phase was washed with water and passed over a plug of silica eluting with dichloromethane. The UV active product fractions were collected and evaporated to yield the title compound as colorless oil (2.04 g 59.3%), MS 229 and 231$(M)^+$.

Example BA

Preparation of (3-(Trifluoromethyl)isoxazol-5-yl)methanamine hydrochloride

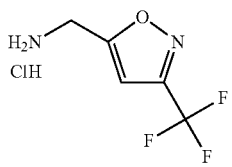 [SMILES: Cl ; NCc1cc(C(F)(F)F)no1]

To a solution of di-tert-butyl iminodicarbonate in dimethylsulfoxide was added sodium hydride 55% in oil (0.30 g, 7.5 mmol, 1.1 eq) and the mixture was stirred for 30 min at ambient temperature. To the resulting white suspension was added dropwise 5-(bromomethyl)-3-(trifluoromethyl)isoxazole (1.5 g, 6.52 mmol, 1 eq). A moderate exothermic reaction was observed. The resulting dark lilac suspension was stirred at ambient for 2 h. The reaction mixture was partitioned between water and heptane (the reaction mixture brightened to a pale yellow). The phases were separated and the organic phase was purified by chromatography on silica gel with heptane:ethyl aceate=9:1 to yield a colorless oil (1.90 g) which was taken up in 4M hydrochloric acid in dioxane (10 mL) and stirred at ambient temperature for 18 h. The resulting precipitate was collected by filtration washed with dioxane and dried to constant weight under high vacuum to yield the title compound as white crystals (0.96 g 72.6% Th), MS 165(M)+.

Example BB

Preparation of
5-Trifluoromethyl-isoxazole-3-carboxylic acid ethyl ester

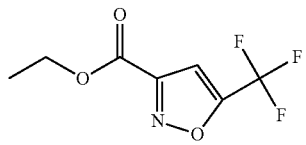

To a solution of 11.44 g ethyl 5,5,5-trifluoro-2,4-dioxopentanoate butyl ester in 75 ml ethanol was added 11.2 g hydroxylamine hydrochloride and the mixture was stirred at reflux for 2 h. The reaction mixture was evaporated and extracted with 100 mL ethyl acetate and 50 mL water. The aqueous layer was back-extracted with 100 mL ethyl acetate. The organic layers were washed with water (2×50 mL). The combined org. layer was dried over Na2SO4, filtered off and concentrated in vacuo. The residue was dissolved in 75 mL toluene. 200 µL pyridine and 7.9 ml thionylchloride were added and the mixture was stirred at reflux for 30 min. The reaction mixture was concentrated in vacuo and extracted with 50 ml ice water and 100 ml ethyl acetate. The aqueous layer was back-extracted with 100 ml ethyl acetate. The organic layers were washed with ice water (2×50 ml). The combined org. layer was dried over Na2SO4, filtered off and concentrated in vacuo. The crude material was purified by flash chromatography over a 500 g SiO2-columne with ethyl acetate/heptane 1:1 as eluent to yield 7.5 g of the title compound as a brown oil. MS (ESI): 208 (M–H)+.

Example BC

Preparation of
(5-Trifluoromethyl-isoxazol-3-yl)-methanol

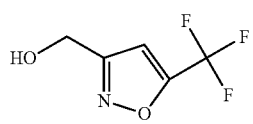 [SMILES: OCc1cc(C(F)(F)F)on1]

To a solution of 7.5 g 5-trifluoromethyl-isoxazole-3-carboxylic acid ethyl ester in 85 mL ethanol was added 3.66 g sodium hydride portion wise at RT. The reaction mixture was stirred at RT for 16 h. 100 mL 1M HCl were added drop by drop under ice-bath cooling. The reaction mixture was extracted with 250 mL diethyl ether and 200 mL sat. NaCl solution/water mixture 1:1. The aqueous layer was back-extracted with diethyl ether (2×100 mL). The org. layers were washed with sat. NaCl solution/water mixture 1:1 (2×200 mL). The combined org. layer was dried over Na2SO4, filtered off and concentrated in vacuo to yield 5.8 g of the title compound as brown oil. MS (EI): 167 (M+H)+.

Example BD

Preparation of
5-(Trifluoromethyl)isoxazol-3-yl)methyl methanesulfonate

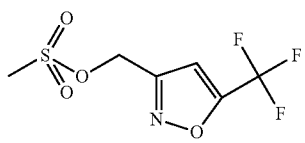

To a solution of 5.8 g (5-trifluoromethyl-isoxazole-3-yl)-methanol in 250 mL CH2Cl2 was added 12.1 mL triethylamine. Methanesulfonylchloride was added drop wise at 0-5° C. The mixture was stirred for 30 min. at this temperature. 50 mL water was added at this temperature. The mixture was extracted with 50 mL sat. NaCl-solution. The aqueous layer was re-extracted with CH2Cl2 (2×100 mL). The combined org. layer was dried over Na2SO4, filtered off and concentrated in vacuo to yield 9.2 g of the title compound as a brown oil.

Example BE

Preparation of
3-(Azidomethyl)-5-(trifluoromethyl)isoxazole

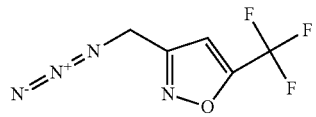 [SMILES: [N-]=[N+]=NCc1cc(C(F)(F)F)on1]

To a solution of 8.7 g (5-(trifluoromethyl)isoxazol-3-yl) methyl methanesulfonate in 87 mL DMF was added 9.23 g sodium azide. The reaction mixture was stirred 3 h at RT. 80 mL water was added under cooling. The mixture was extracted with diethyl ether (3×100 mL) and the organic layers were washed with water (3×100 mL) and then with sat. NaCl solution (1×100 mL). The combined organic layer was dried over Na2SO4, filtered off and concentrated in vacuo to yield 6.26 g of the title compound as a brown oil.

Example BF

Preparation of 5-trifluoromethyl-isoxazol-3-methane amine

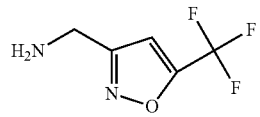 [SMILES: NCc1cc(C(F)(F)F)on1]

To a solution of 6.26 g 3-(azidomethyl)-5-(trifluoromethyl)isoxazole in 100 mL 2-propanol were added 9.08 mL triethyl amine and 330 uL 1,3-propanedithiol. 2.45 g sodiumhydride were added portion wise and stirred at RT for 16 h. The reaction mixture was concentrated in vacuo. The residue was poured carefully into 180 mL 10% acetic acid and washed with diethyl ether/heptane mixture 1.1 (3×50 mL) The aqueous layer was basified with conc. NaOH to pH=12 (50 mL), saturated with NaCl and extracted with CH$_2$Cl$_2$ (3×250 mL). The combined organic layer was dried over Na$_2$SO$_4$, filtered off and concentrated in vacuo to yield 3.4 g of the title compound as yellow oil; LC-MS (UV peak area/ESI) 97.6%, 167.043 (M+H)$^+$.

Example BG

Preparation of 5-trifluoromethyl-isoxazol-3-methanamine hydrochloride

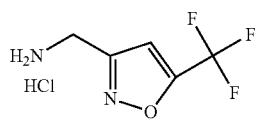 [SMILES: Cl ; NCc1cc(C(F)(F)F)on1]

To a solution of (5-(trifluoromethyl)isoxazol-3-yl)methanamine in 25 ml ethanol was added under cooling 5.12 mL 4M–HCl solution in dioxane over a period of 10 min. The ice-bath was removed and 25 ml diethyl ether was added drop by drop. Precipitation. Filtered off and washed with diethyl ether 83×5 mL). Dried in vacuo at 40° C. to yield 2.65 g of the title compound as a white solid. MS (EI): 166 (M+H)$^+$.

Example BH

The starting material 2-cyclopropyl-oxazol-4-methanamine was prepared as follows.

A mixture of cyclopropanecarboxylic acid amide (5.0 g, 58.74 mmol) and 1,3-dichloro-propan-2-one (14.92 g, 117.49 mmol) was heated at 110° C. for 4 h. The mixture was cooled to room temperature and water (75 mL) was added and the mixture was extracted with dichloromethane (3×50 mL). The organic layer was dried over anhydrous sodium sulphate and evaporated in vacuo to get crude residue. After purification via column chromatography (100-200 silica gel, elution with 2% EtOAc in hexane), 4 g of 4-chloromethyl-2-cyclopropyloxazole was obtained as a dark brown liquid, 158.0 (M+H)$^+$. But it contained impurities. This compound was used for the next step as such.

To the stirred solution of 4-chloromethyl-2-cyclopropyloxazole (4.0 g, 25.38 mmol) in dry DMF (30 mL), was added potassium salt of phthalimide (4.7 g, 25.38 mmol) at rt. The resulting mixture was stirred for 24 h at rt and monitored through TLC. After completion of the reaction, water (200 mL) was added and the crude was extracted with ethyl acetate (3×50 mL). The combined organic layer was washed with brine, dried over anhydrous sodium sulphate and concentrated under reduced pressure to obtained crude residue which was purified via column chromatography (100-200 silica gel, elution with 20% EtOAc in hexane). 3.5 g of 2-(2-cyclopropyl-oxazol-4-ylmethyl)-isoindole-1,3-dione was obtained as a white solid, 269.2 (M+H)$^+$, which contained phthalimide. This compound was used for the next step as such.

To the suspension of 2-(2-cyclopropyl-oxazol-4-ylmethyl)-isoindole-1,3-dione (2.0 g, 7.45 mmol) in EtOH (40 mL), was added hydrazine monohydrate (0.435 mL, 8.94 mmol) at rt. The resulting mixture was heated to reflux for 5 h and monitored through TLC. After completion, the reaction mixture was allowed to rt and the precipitated solid was filtered off and washed with ethanol (20 mL). The filtrate was concentrated under reduced pressure to get the crude residue which was purified by column chromatography over de-activated silica (5% triethylamine in hexane, elution with 3% MeOH in DCM). The title compound (3.5 g, 41.6% yield) was obtained as brown sticky liquid, 139.2 (M+H)$^+$.

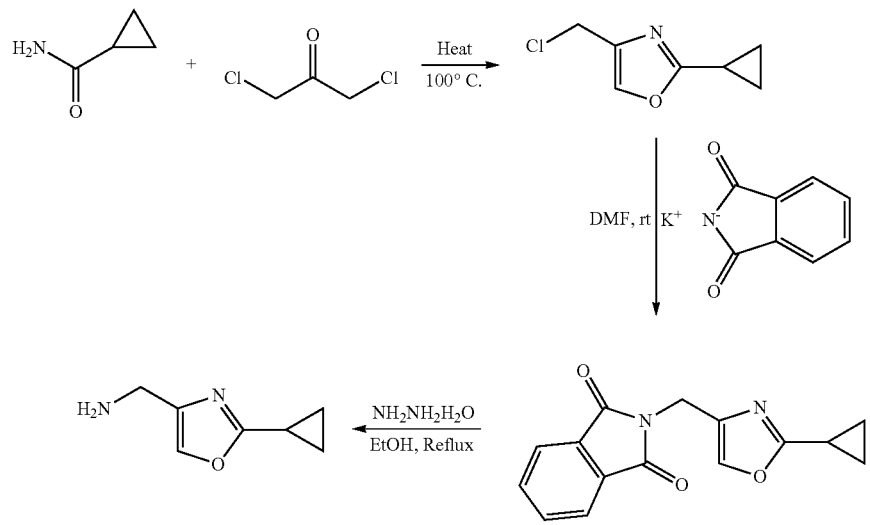

Example BI

Preparation of methyl 5-(4-chloro-3-methylphenyl)-6-(2,2,2-trifluoroethoxy)nicotinate

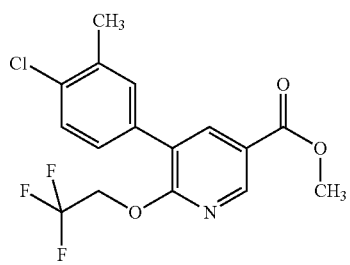 [SMILES: COC(=O)c1cnc(OCC(F)(F)F)c(-c2ccc(Cl)c(C)c2)c1]

5-Bromo-6-(2,2,2-trifluoroethoxy)-3-pyridinecarboxylic acid methyl ester (CAN 1211589-51-3; 4.0 g; 12.7 mmol) and 4-chloro-3-methylphenylboronic acid (CAN 161950-10-3; 3.26 g, 19.1 mmol) were combined in DMSO (100 mL) to give a white suspension. To this suspension was added, $Na_2CO_3$ (4.05 g, 38.2 mmol) in water (10 mL) and 1,1'-bis(diphenylphosphino)-ferrocene-palladium(II)dichloride dichloromethane complex (1.04 g, 1.27 mmol). The reaction mixture was heated to 80° C. and stirred for 2.5 h, cooled and poured into 200 mL ethyl acetate:heptane (1:1) and extracted with $H_2O$ (3×100 mL) and brine (1×150 ml). The aqueous layer was extracted with EtOAc:Heptane (1:1) (1×200 mL). The organic layers were combined, dried with $Na_2SO_4$ and concentrated in vacuo. The crude material was purified by flash chromatography (silica gel, 70 g, 0% to 100% ethyl acetate in heptane) to yield 4.86 g (90%) of the title compound as light red solid; MS (EI): 360.1 (M+H)$^+$.

Example BJ

Preparation of 5-(4-chloro-3-methylphenyl)-6-(2,2,2-trifluoroethoxy)nicotinic acid

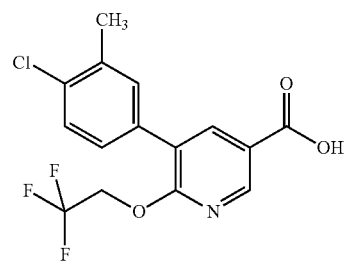 [SMILES: Cc1cc(-c2cc(C(=O)O)cnc2OCC(F)(F)F)ccc1Cl]

Methyl 5-(4-chloro-3-methylphenyl)-6-(2,2,2-trifluoroethoxy)nicotinate (example BI; 4.8 g, 13.3 mmol) and LiOH (0.96 g, 40.0 mmol) were combined with THF (70 mL), water (14 mL) and methanol (7 mL) to give a yellow suspension. The reaction mixture was stirred for 22 h at room temperature, 15 mL water was added and the reaction mixture was heated to 45° C. and stirred for 3 h. After cooling to room temperature the reaction mixture was poured into 150 mL of 1 M HCl with ice (pH=1) and extracted with ethyl acetate (2×150 mL). The organic layers were combined, dried with $Na_2SO_4$, filtrated and concentrated in vacuo. The crude material was purified by flash chromatography (silica gel, 70 g, 0% to 100% EtOAc in heptane to give 3.8 g (82%) of the title compound as a white crystalline solid; MS (ESI): 346.1 (M+H)$^+$.

Example BK

Preparation of (6-chloro-4-(3-chloro-4-methylphenyl)-5-(2,2,2-trifluoroethoxy)pyridin-2-yl)methanol

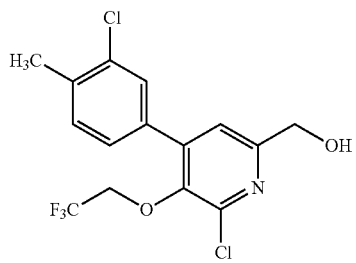 [SMILES: Cc1ccc(-c2cc(CO)nc(Cl)c2OCC(F)(F)F)cc1Cl]

The title compound was synthesized in analogy to Example B using [4-iodo-6-chloro-5-(2,2,2-trifluoroethoxy)-pyridin-2-yl]-methanol (example A) and B-(3-chloro-4-methylphenyl)-boronic acid, (CAN 175883-63-3) as starting materials; LC-MS (UV peak area/ESI) 100%, 366.0269 (M+H)$^+$.

Example BL

Preparation of (4-(3-chloro-4-methylphenyl)-5-(2,2,2-trifluoroethoxy)pyridin-2-yl)methanol

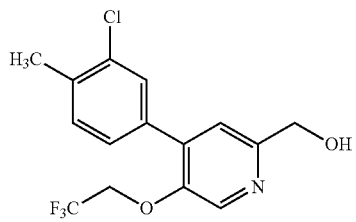 [SMILES: Cc1ccc(-c2cc(CO)ncc2OCC(F)(F)F)cc1Cl]

The title compound was synthesized in analogy to Example C using (6-chloro-4-(3-chloro-4-methylphenyl)-5-(2,2,2-trifluoroethoxy)pyridin-2-yl)methanol (example BK) as starting material; LC-MS (UV peak area/ESI) 98.8%, 332.0660 (M+H)$^+$.

Example BM

Preparation of 4-(3-chloro-4-methylphenyl)-5-(2,2,2-trifluoroethoxy)picolinic acid

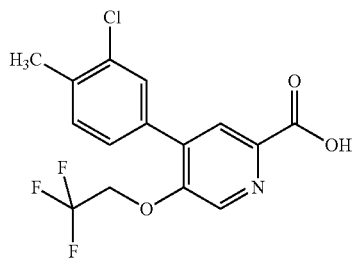 [SMILES: Cc1ccc(-c2cc(C(=O)O)ncc2OCC(F)(F)F)cc1Cl]

The title compound was synthesized in analogy to Example D using (4-(3-chloro-4-methylphenyl)-5-(2,2,2-trifluoroethoxy)pyridin-2-yl)methanol (example BL) as starting material; LC-MS (UV peak area/ESI) 100%, 346.0447 (M+H)$^+$.

Example BN

Preparation of 4-(4-chloro-3-methylphenyl)-5-(2,2,2-trifluoroethoxy)picolinic acid

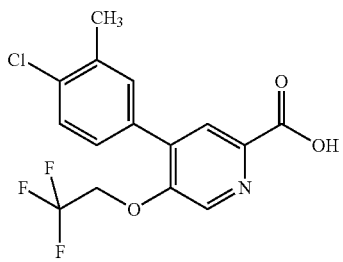 [SMILES: Cc1cc(-c2cc(C(=O)O)ncc2OCC(F)(F)F)ccc1Cl]

The title compound was synthesized in analogy to Examples B to D using [4-iodo-6-chloro-5-(2,2,2-trifluoroethoxy)-pyridin-2-yl]-methanol (example A) and B-(4-chloro-3-methylphenyl)-boronic acid, (CAN 161950-10-3) as starting materials; LC-MS (UV peak area/ESI) 100%, 346.0454 (M+H)$^+$.

Example BO

Preparation of 4-(3,4-dimethylphenyl)-5-(2,2,2-trifluoroethoxy)picolinic acid

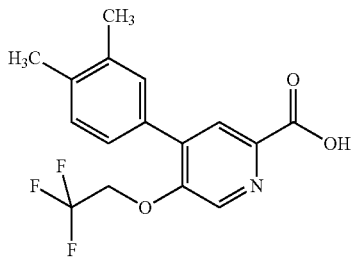 [SMILES: Cc1ccc(-c2cc(C(=O)O)ncc2OCC(F)(F)F)cc1C]

The title compound was synthesized in analogy to Examples B to D using [4-iodo-6-chloro-5-(2,2,2-trifluoroethoxy)-pyridin-2-yl]-methanol (example A) and B-(3,4-dimethylphenyl)-boronic acid, (CAN 55499-43-9) as starting materials; LC-MS (UV peak area/ESI) 100%, 326.1004 (M+H)$^+$.

Example BP

Preparation of 5-bromo-6-(2,2,2-trifluoroethoxy)-N-((3-(trifluoromethyl)-1,2,4-oxadiazol-5-yl)methyl)nicotinamide

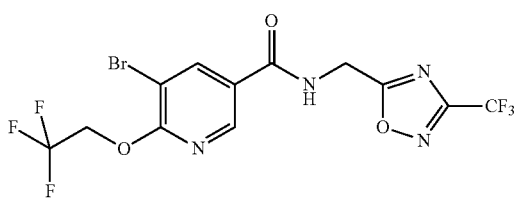 [SMILES: O=C(NCc1nc(C(F)(F)F)no1)c1cnc(OCC(F)(F)F)c(Br)c1]

The title compound was synthesized in analogy to Example 1 using 5-bromo-6-(2,2,2-trifluoroethoxy)-3-pyridinecarboxylic acid (CAN 1211586-75-2) and 3-trifluoromethyl-[1,2,4]oxadiazol-5-methanamine (example AK) as starting materials; LC-MS (UV peak area/ESI) 97%, 448.9532 (M−H)$^−$.

Example BQ

Preparation of 5-(3-chloro-4-fluorophenyl)-6-(2,2,2-trifluoroethoxy)nicotinic acid

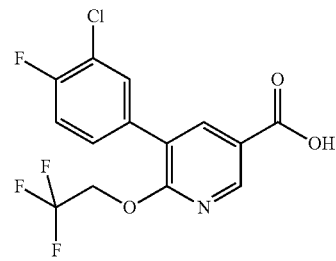

5-Bromo-6-(2,2,2-trifluoroethoxy)-3-pyridinecarboxylic acid (CAN 1211586-75-2; 1.5 g; 5.0 mmol) was dissolved in toluene (35 mL) an DMF (2 mL). To this solution was added 1,1'-bis(diphenylphosphino)-ferrocene-palladium(II)dichloride dichloromethane complex (204 mg, 250 µmol), followed by 3-chloro-4-fluorophenylboronic acid (CAN 144432-85-9; 959 mg, 5.5 mmol) and 2M—Na$_2$CO$_3$ (20.0 ml, 40.0 mmol). The reaction mixture was heated to 90° C. and stirred for 4 h, cooled and poured into 100 mL ice water, acidified with 45 mL 2N—HCl and extracted ethyl acetate. The organic layers were combined, dried with Na$_2$SO$_4$ and concentrated in vacuo. The crude material was crystallized from heptane:ethyl acetate (5:1) to yield 1.1 g (63%) of the title compound as light grey solid; LC-MS (UV peak area/ESI): 97%, 348.0066 (M−H)$^−$.

Example BR

Preparation of 5-(4-chloro-3-fluorophenyl)-6-(2,2,2-trifluoroethoxy)nicotinic acid

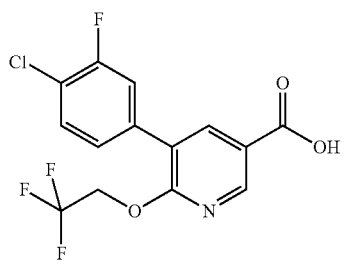 [SMILES: O=C(O)c1cnc(OCC(F)(F)F)c(-c2ccc(Cl)c(F)c2)c1]

The title compound was synthesized in analogy to Example BQ using 5-bromo-6-(2,2,2-trifluoroethoxy)-3-pyridinecarboxylic acid (CAN 1211586-75-2) and B-(4-chloro-3-fluorophenyl)-boronic acid, (CAN 137504-86-0) as starting materials; LC-MS (UV peak area/ESI) 96%, 348.0058 (M−H)$^−$.

Example BS

Preparation of 5-(4-ethylphenyl)-6-(2,2,2-trifluoroethoxy)nicotinic acid

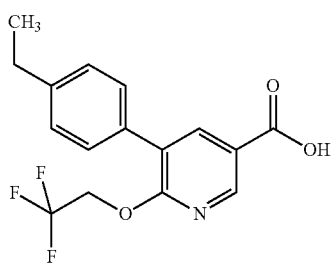 [SMILES: CCc1ccc(-c2cc(C(=O)O)cnc2OCC(F)(F)F)cc1]

The title compound was synthesized in analogy to Example BQ using 5-bromo-6-(2,2,2-trifluoroethoxy)-3-pyridinecarboxylic acid (CAN 1211586-75-2) and B-(4-ethylphenyl)-boronic acid, (CAN 63139-21-9) as starting materials; LC-MS (UV peak area/ESI) 95.8%, 324.0859 (M–H)⁻.

Example BT

Preparation of 5-(4-chloro-2-fluorophenyl)-6-(2,2,2-trifluoroethoxy)nicotinic acid

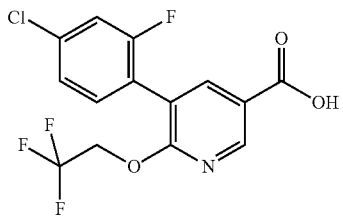 [SMILES: O=C(O)c1cnc(OCC(F)(F)F)c(-c2ccc(Cl)cc2F)c1]

The title compound was synthesized in analogy to Examples BI to BJ using 5-bromo-6-(2,2,2-trifluoroethoxy)-3-pyridinecarboxylic acid methyl ester (CAN 1211589-51-3) and B-(4-chloro-2-fluorophenyl)-boronic acid, (CAN 160591-91-3) as starting materials; LC-MS (UV peak area/ESI) 98.8%, 348.0061 (M–H)⁻.

Example BU

Preparation of 5-(4-cyano-phenyl)-6-(2,2,2-trifluoro-ethoxy)-nicotinic acid

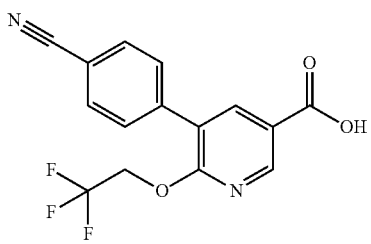 [SMILES: N#Cc1ccc(-c2cc(C(=O)O)cnc2OCC(F)(F)F)cc1]

The title compound was synthesized in analogy to Example BQ using 5-bromo-6-(2,2,2-trifluoroethoxy)-3-pyridinecarboxylic acid (CAN 1211586-75-2) and B-(4-cyanophenyl)-boronic acid, (CAN 126747-14-6) as starting materials; MS (ESI): 321.2 (M–H).

Example BV

Preparation of 2-((1-(cyclopropylmethyl)-1H-pyrazol-3-yl)methyl)isoindoline-1,3-dione

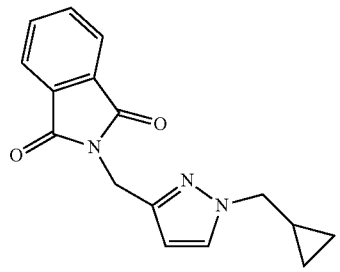 [SMILES: O=C1c2ccccc2C(=O)N1Cc1ccn(CC2CC2)n1]

To a colorless solution of 2-(1H-pyrazol-3-ylmethyl)-1H-Isoindole-1,3(2H)-dione (CAN 95533-75-8; 3.66 g, 16.1 mmol) in DMF (80 mL) at 0° C. was added in 4 portions sodium hydride (1.29 g, 32.2 mmol) within 15 min. After warming to room temperature the mixture was stirred for 30 min and cyclopropylmethyl bromide (21.7 g, 15.6 mL, 161 mmol) in DMF (20 mL) was added within 30 min. The mixture was stirred for 22 h at room temperature, poured into ethyl acetate (200 mL) and extracted with water (3×100 mL). Water phases were washed with ethyl acetate (200 mL), organic phases were combined, dried with MgSO₄ and concentrated in vacuo. The crude material was purified by flash chromatography (silica gel, 80 g, 0% to 100% EtOAc in heptane) and finally by preparative HPLC to give 1.63 g (36%) of the title compound as a white solid; MS (EI): 282.2 (M+H)⁺.

Example BW

Preparation of (1-(cyclopropylmethyl)-1H-pyrazol-3-yl)methanamine

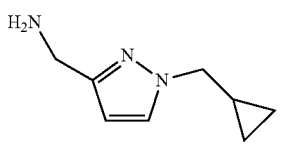 [SMILES: NCc1ccn(CC2CC2)n1]

To a colorless solution of 2-((1-(cyclopropylmethyl)-1H-pyrazol-3-yl)methyl)isoindoline-1,3-dione (example BV; 400 mg, 1.42 mmol) in THF (10 mL) and ethanol (5 mL) was added hydrazine hydrate (0.62 g, 0.60 mL, 12.3 mmol). The white suspension was stirred for 20 h at room temperature, diluted with t-butylmethyl ether (50 mL) and phtalyl hydrazide was removed by filtration. The filtrate was concentrated in vacuo and the crude material was purified by flash chromatography (amino phase, 12 g, 0% to 100% ethyl acetate in heptane) to yield 197 mg (92%) of the title compound as a light yellow oil; MS (EI): 152.1 (M+H)⁺.

Example BX

Preparation of 5-(3,4-difluorophenyl)-6-(2,2,2-trifluoroethoxy)nicotinic acid

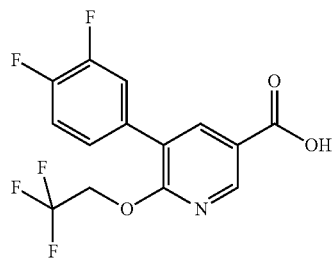 [SMILES: O=C(O)c1cnc(OCC(F)(F)F)c(-c2ccc(F)c(F)c2)c1]

The title compound was synthesized in analogy to Example BQ using 5-bromo-6-(2,2,2-trifluoroethoxy)-3-pyridinecarboxylic acid (CAN 1211586-75-2) and B-(3,4-difluorophenyl)-boronic acid, (CAN 168267-41-2) as starting materials.

Example BY

Preparation of 5-bromo-6-cyclobutoxynicotinic acid

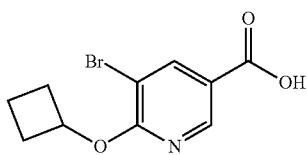 [SMILES: O=C(O)c1cnc(OC2CCC2)c(Br)c1]

5-Bromo-6-chloronicotinic acid (CAN 29241-62-1, 2.0 g, 8.46 mmol) was dissolved in DMSO (20.0 mL). Cyclobutanol (793 mg, 857 µL, 11.0 mmol) and potassium hydroxide powder (1.42 g, 25.4 mmol) were added and the mixture was stirred at room temperature overnight. Water (20 mL) was added and the mixture was acidified (under ice-water bath cooling) with 37% HCL in water (pH=2). The suspension was filtered, washed with water and the solid was dried to yield 1.88 g (82%) of the title compound as a white solid; MS (ESI): 270.2 (M−H)⁻.

Example BZ

Preparation of 6-cyclobutoxy-5-(3,4-difluorophenyl)nicotinic acid

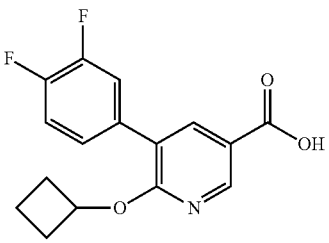 [SMILES: O=C(O)c1cnc(OC2CCC2)c(-c2ccc(F)c(F)c2)c1]

The title compound was synthesized in analogy to Example BQ using 6-cyclobutoxy-5-(3,4-difluorophenyl)nicotinic acid (example BY) and B-(3,4-difluorophenyl)-boronic acid (CAN 168267-41-2) as starting materials; MS (ESI): 304.2 (M−H)⁻.

Example CA

Preparation of 5-(4-chlorophenyl)-6-cyclobutoxynicotinic acid

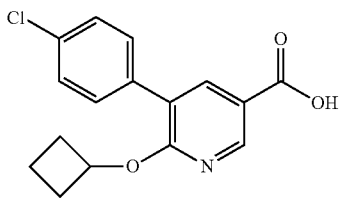 [SMILES: O=C(O)c1cnc(OC2CCC2)c(-c2ccc(Cl)cc2)c1]

The title compound was synthesized in analogy to Example BQ using 5-bromo-6-cyclobutoxy-5-nicotinic acid (example BY) and B-(4-chlorophenyl)-boronic acid (CAN 1679-18-1) as starting materials; MS (ESI): 302.2 (M−H)⁻.

Example CB

Preparation of 5-(4-chloro-3-fluorophenyl)-6-cyclobutoxynicotinic acid

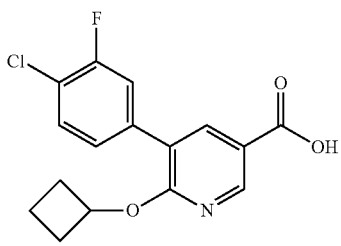 [SMILES: O=C(O)c1cnc(OC2CCC2)c(-c2ccc(Cl)c(F)c2)c1]

The title compound was synthesized in analogy to Example BQ using 5-bromo-6-cyclobutoxy-5-nicotinic acid (example BY) and B-(4-chloro-3-fluorophenyl)-boronic acid (CAN 137504-86-0) as starting materials; MS (ESI): 320.2 (M−H)⁻.

Example CC

Preparation of 5-(4-chloro-3-methylphenyl)-6-cyclobutoxynicotinic acid

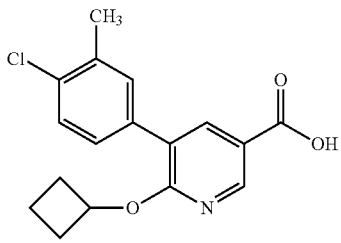 [SMILES: Cc1cc(-c2cc(C(=O)O)cnc2OC2CCC2)ccc1Cl]

The title compound was synthesized in analogy to Example BQ using 5-bromo-6-cyclobutoxy-nicotinic acid (example BY) and B-(4-chloro-3-methylphenyl)-boronic acid (CAN 161950-10-3) as starting materials; MS (ESI): 316.2 (M−H)⁻.

Example CD

Preparation of 6-(cyclopropylmethoxy)-5-(3,4-difluorophenyl)nicotinic acid

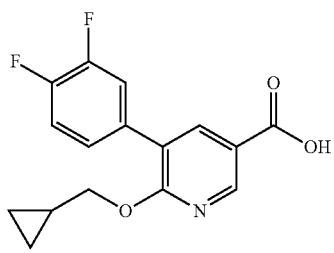 [SMILES: O=C(O)c1cnc(OCC2CC2)c(-c2ccc(F)c(F)c2)c1]

The title compound was synthesized in analogy to Example BQ using 5-bromo-6-(cyclopropylmethoxy)-3-pyridinecarboxylic acid (CAN 912454-38-7) and B-(3,4-difluorophenyl)-boronic acid, (CAN 168267-41-2) as starting materials; MS (ESI): 304.2 (M−H)⁻.

Example CE

Preparation of 5-(3,4-difluorophenyl)-6-(2-methoxyethoxy)nicotinic acid

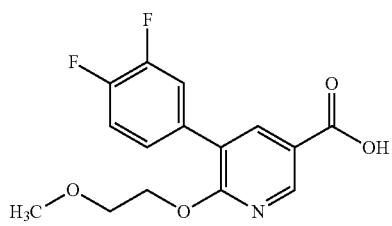 [SMILES: COCCOc1ncc(C(=O)O)cc1-c1ccc(F)c(F)c1]

The title compound was synthesized in analogy to Example BQ using 5-bromo-6-(2-methoxyethoxy)-3-pyridinecarboxylic acid (CAN 912454-34-3) and B-(3,4-difluorophenyl)-boronic acid, (CAN 168267-41-2) as starting materials; MS (ESI): 308.3 (M−H)⁻.

Example CF

Preparation of 5-(4-chloro-3-fluorophenyl)-6-(2-methoxyethoxy)nicotinic acid

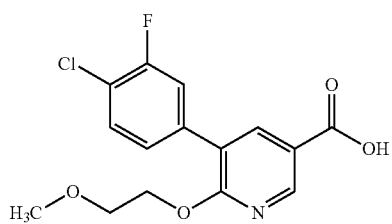

The title compound was synthesized in analogy to Example BQ using 5-bromo-6-(2-methoxyethoxy)-3-pyridinecarboxylic acid (CAN 912454-34-3) and B-(4-chloro-3-fluorophenyl)-boronic acid (CAN 137504-86-0) as starting materials; LC-MS (UV peak area/ESI) 100%, 324.0456 (M−H)⁻.

Example CG

Preparation of 5-(4-chloro-3-methylphenyl)-6-(2-methoxyethoxy)nicotinic acid

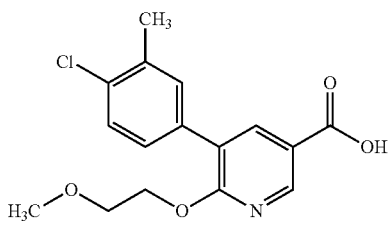 [SMILES: COCCOc1ncc(C(=O)O)cc1-c1ccc(Cl)c(C)c1]

The title compound was synthesized in analogy to Example BQ using 5-bromo-6-(2-methoxyethoxy)-3-pyridinecarboxylic acid (CAN 912454-34-3) and B-(4-chloro-3-methylphenyl)-boronic acid (CAN 161950-10-3) as starting materials; LC-MS (UV peak area/ESI) 94%, 322.0842 (M+H)⁺.

Example CH

Preparation of 5-benzo[1,2,5]oxadiazol-5-yl-6-(2,2,2-trifluoro-ethoxy)-nicotinic acid

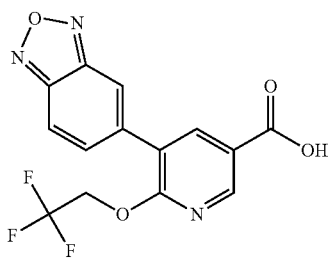 [SMILES: O=C(O)c1cnc(OCC(F)(F)F)c(-c2ccc3nonc3c2)c1]

The title compound was synthesized in analogy to Example BQ using 5-bromo-6-(2,2,2-trifluoroethoxy)-3-pyridinecarboxylic acid (CAN 1211586-75-2) and B-2,1,3-benzoxadiazol-5-yl-boronic acid, (CAN 426268-09-9) as starting materials; LC-MS (UV peak area/ESI) 48%, 338.0 (M−H)⁻.

Example CI

Preparation of 5-(4-chlorophenyl)-6-(2-hydroxyethoxy)nicotinic acid

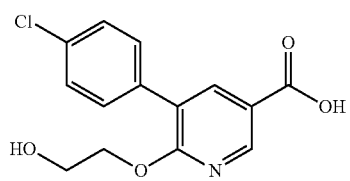

To a solution of ethane-1,2-diol (301 mg, 270 µA, 4.84 mmol) in dried DMF (6 mL) was added sodium hydride (232 mg, 4.84 mmol) and the reaction mixture was stirred at room temperature for 15 minutes. The resulting solution was added slowly to a solution of 6-chloro-5-(4-chlorophenyl)-3-pyridinecarboxylic acid (CAN 1012792-56-1; 0.590 g, 2.2 mmol) in dried DMF (6 mL) and stirred at 80° C. for 4 h. More sodium hydride (106 mg, 2.2 mmol) was added and at room temperature and stirring at 80° C. commenced for another 2 h. Water was added and DMF was evaporated. The residue was dissolved in water; acidified with 3M HCl to pH 3. The suspension was filtered; the filter cake was washed with water and dried under high vacuo. The crude material was purified by flash chromatography (ReproFlash Acidosil-S, 50 g, 50% to 100% ethylacetate in heptane) to give 0.27 g (41%) of the title compound as a white solid; MS (ESI): 292.1 (M–H)⁻.

Example CJ

Preparation of (R)-5-(4-chlorophenyl)-6-(tetrahydro-furan-3-yloxy)nicotinic acid

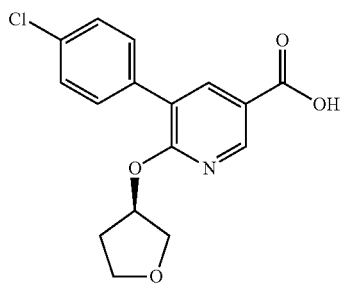 [SMILES: O=C(O)c1cnc(O[C@@H]2CCOC2)c(-c2ccc(Cl)cc2)c1]

The title compound was synthesized in analogy to Example CI using 6-chloro-5-(4-chlorophenyl)-3-pyridinecarboxylic acid (CAN 1012792-56-1) and (3R)-tetrahydro-3-furanol (CAN 86087-24-3) as starting materials; LC-MS (UV peak area/ESI) 88.1%, 318.1 (M–H)⁻.

Example CK

Preparation of 5-(4-chloro-phenyl)-6-(tetrahydro-furan-3-ylmethoxy)-nicotinic acid

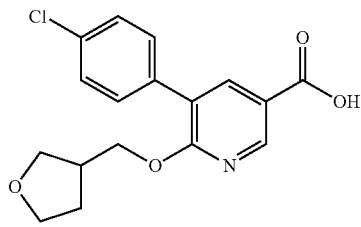 [SMILES: O=C(O)c1cnc(OCC2CCOC2)c(-c2ccc(Cl)cc2)c1]

The title compound was synthesized in analogy to Example CI using 6-chloro-5-(4-chlorophenyl)-3-pyridine carboxylic acid (CAN 1012792-56-1) and tetrahydro-3-furanmethanol (CAN 15833-61-1) as starting materials; LC-MS (UV peak area/ESI) 91.6%, 334.0833 (M+H)⁺.

Example 1

Preparation of 4-(4-chloro-phenyl)-5-(2,2,2-trifluoro-ethoxy)-pyridine-2-carboxylic acid (3-methoxy-isoxazol-5-ylmethyl)-amide

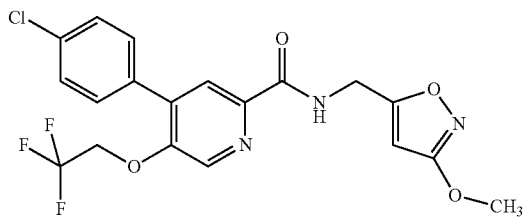 [SMILES: COc1cc(CNC(=O)c2cc(-c3ccc(Cl)cc3)c(OCC(F)(F)F)cn2)on1]

4-(4-Chloro-phenyl)-5-(2,2,2-trifluoro-ethoxy)-pyridine-2-carboxylic acid (100 mg, 0.3 mmol, example D) was dissolved in dimethylformamide (4 mL). To this stirred solution under argon was added in sequence 2-(1H-benzotriazole-1-yl)-1,1,3,3-tetramethyluronium tetrafluoroborate (107 mg, 0.3 mmol), N,N-diisopropyl ethyl amine (0.26 mL, 1.5 mmol) and 3-methoxy-5-isoxazolemethanamine hydrochloride (55 mg, 0.3 mmol). The mixture was shaken for 16 h at room temperature, solvent was removed in vacuo (45° C.) and the residue was digested with dichloromethane (5 mL) and 2N NaOH (1.5 mL) for 5 min. The mixture was absorbed onto 10 g ChemElut (Varian) and eluted with dichloromethane (70 mL). Solvent was evaporated and the brown, oily residue (160 mg) was purified by gradient chromatography on silica with ethyl acetate/n-heptane to give the title compound as a white solid (122 mg, 92%), LC-MS (UV peak area/ESI) 93%, 442.0769 (M+H)⁺.

Example 2

Preparation of 4-(4-chloro-phenyl)-5-(2,2,2-trifluoro-ethoxy)-pyridine-2-carboxylic acid (3-isopropyl-isoxazol-5-ylmethyl)-amide

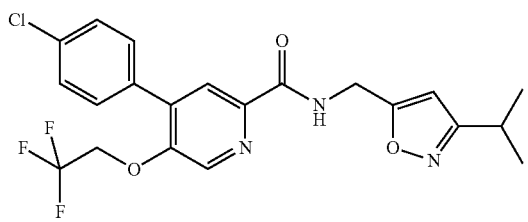 [SMILES: CC(C)c1cc(CNC(=O)c2cc(-c3ccc(Cl)cc3)c(OCC(F)(F)F)cn2)on1]

The title compound was synthesized in analogy to Example 1, using 4-(4-chloro-phenyl)-5-(2,2,2-trifluoro-ethoxy)-pyridine-2-carboxylic acid (example D) and 3-(1-methylethyl)-5-isoxazolemethanamine as starting materials; LC-MS (UV peak area/ESI) 100%, 454.1134 (M+H)⁺.

Example 3

Preparation of 4-(4-chloro-phenyl)-5-(2,2,2-trifluoro-ethoxy)-pyridine-2-carboxylic acid (3-ethyl-isoxazol-5-ylmethyl)-amide

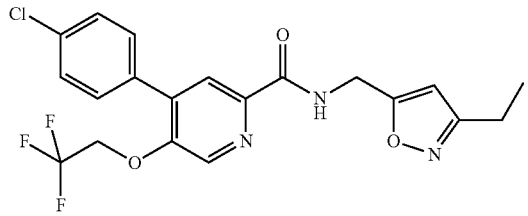 [SMILES: CCc1cc(CNC(=O)c2cc(-c3ccc(Cl)cc3)c(OCC(F)(F)F)cn2)on1]

The title compound was synthesized in analogy to Example 1, using 4-(4-chloro-phenyl)-5-(2,2,2-trifluoro-ethoxy)-pyridine-2-carboxylic acid (example D) and 3-ethyl-5-isoxazolemethanamine as starting materials; LC-MS (UV peak area/ESI) 100%, 440.0985 (M+H)$^+$.

Example 4

Preparation of 4-(4-chloro-phenyl)-5-(2,2,2-trifluoro-ethoxy)-pyridine-2-carboxylic acid (1-propyl-1H-pyrazol-3-ylmethyl)-amide

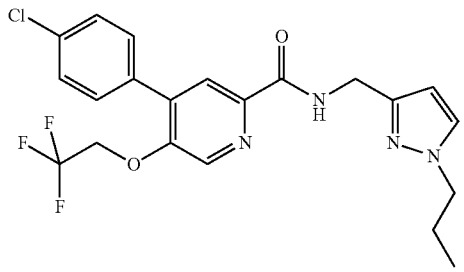 [SMILES: CCCn1ccc(CNC(=O)c2cc(-c3ccc(Cl)cc3)c(OCC(F)(F)F)cn2)n1]

The title compound was synthesized in analogy to Example 1, using 4-(4-chloro-phenyl)-5-(2,2,2-trifluoro-ethoxy)-pyridine-2-carboxylic acid (example D) and 1-propyl-1H-pyrazole-3-methanamine (CAS Registry No. 1006333-47-6) as starting materials; LC-MS (UV peak area/ESI) 100%, 453.1306 (M+H)$^+$.

Example 5

Preparation of 5-(4-chloro-phenyl)-N-(3-methoxy-isoxazol-5-ylmethyl)-6-(2,2,2-trifluoro-ethoxy)-nicotinamide

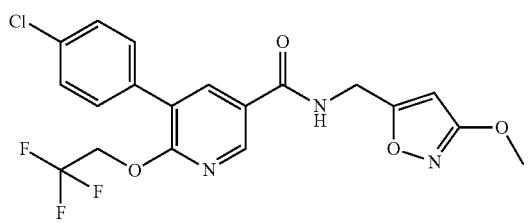 [SMILES: COc1cc(CNC(=O)c2cnc(OCC(F)(F)F)c(-c3ccc(Cl)cc3)c2)on1]

The title compound was synthesized in analogy to Example 1, using 5-(4-chlorophenyl)-6-(2,2,2-trifluoroethoxy)-3-pyridinecarboxylic acid (CAS Registry No. 1018782-82-5) and 3-methoxy-5-isoxazolemethanamine hydrochloride as starting materials, LC-MS (UV peak area/ESI) 100%, 442.079 (M+H)$^+$.

Example 6

Preparation of 4-(4-chloro-phenyl)-5-(2,2,2-trifluoro-ethoxy)-pyridine-2-carboxylic acid (2-isopropyl-thiazol-4-ylmethyl)-amide

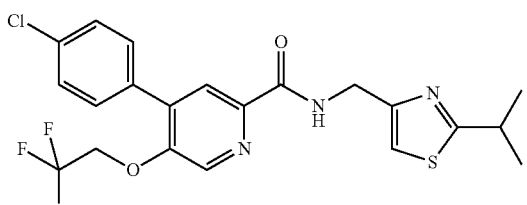

The title compound was synthesized in analogy to Example 1, using 4-(4-chloro-phenyl)-5-(2,2,2-trifluoro-ethoxy)-pyridine-2-carboxylic acid (example D) and 2-(1-methylethyl)-4-thiazole-methanamine, as starting materials; LC-MS (UV peak area/ESI) 80%, 470.902 (M+H)$^+$.

Example 7

Preparation of 5-(4-chloro-phenyl)-N-(2-ethyl-thiazol-4-ylmethyl)-6-(2,2,2-trifluoro-ethoxy)-nicotinamide

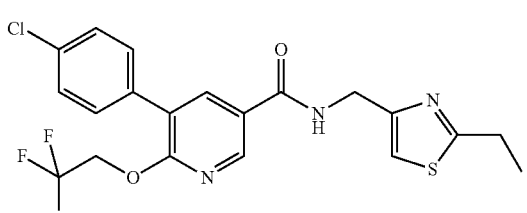

The title compound was synthesized in analogy to Example 1, using 5-(4-chlorophenyl)-6-(2,2,2-trifluoroethoxy)-3-pyridinecarboxylic acid (CAS Registry No. 1018782-82-5) and 2-ethyl-4-thiazolemethanamine as starting materials; LC-MS (UV peak area/ESI) 98%, 456.074 (M+H)$^+$.

Example 8

Preparation of 5-(4-chloro-phenyl)-N-(2-isopropyl-thiazol-4-ylmethyl)-6-(2,2,2-trifluoro-ethoxy)-nicotinamide

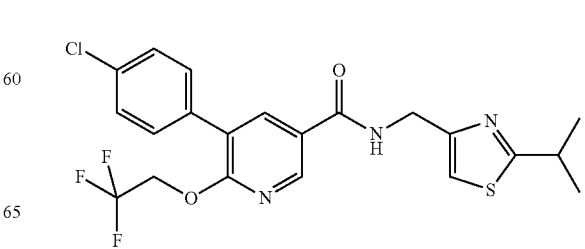

The title compound was synthesized in analogy to Example 1, using 5-(4-chlorophenyl)-6-(2,2,2-trifluoroethoxy)-3-pyridinecarboxylic acid (CAS Registry No. 1018782-82-5) and 2-(1-methylethyl)-4-thiazolemethanamine as starting materials, LC-MS (UV peak area/ESI) 98%, 470.090 (M+H)⁺.

Example 9

Preparation of 5-(4-chloro-phenyl)-N-(2-propyl-thiazol-4-ylmethyl)-6-(2,2,2-trifluoro-ethoxy)-nicotinamide

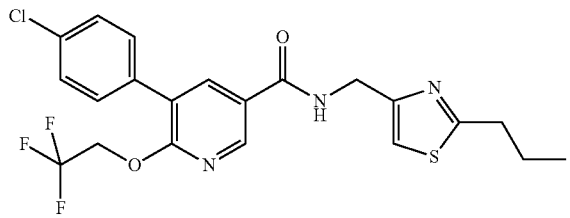 [SMILES: CCCc1nc(CNC(=O)c2cnc(OCC(F)(F)F)c(-c3ccc(Cl)cc3)c2)cs1]

The title compound was synthesized in analogy to Example 1, using 5-(4-chlorophenyl)-6-(2,2,2-trifluoroethoxy)-3-pyridinecarboxylic acid (CAS Registry No. 1018782-82-5) and 2-propyl-4-thiazolemethanamine as starting materials, LC-MS (UV peak area/ESI) 99%, 470.090 (M+H)⁺.

Example 10

Preparation of 5-(4-chloro-phenyl)-6-cyclopropylmethoxy-N-(2-ethyl-thiazol-4-ylmethyl)-nicotinamide

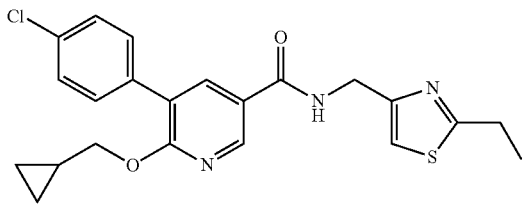 [SMILES: CCc1nc(CNC(=O)c2cnc(OCC3CC3)c(-c3ccc(Cl)cc3)c2)cs1]

The title compound was synthesized in analogy to Example 1, using 5-(4-chlorophenyl)-6-(cyclopropylmethoxy)-3-pyridinecarboxylic acid (CAS Registry No. 1018782-76-7) and 2-ethyl-4-thiazolemethanamine as starting materials, LC-MS (UV peak area/ESI) 99%, 428.119 (M+H)⁺.

Example 11

Preparation of 5-(4-chloro-phenyl)-6-cyclopropylmethoxy-N-(2-propyl-thiazol-4-ylmethyl)-nicotinamide

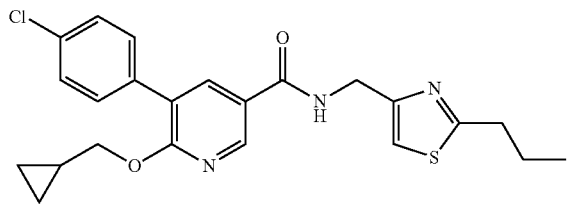 [SMILES: CCCc1nc(CNC(=O)c2cnc(OCC3CC3)c(-c3ccc(Cl)cc3)c2)cs1]

The title compound was synthesized in analogy to Example 1, using 5-(4-chlorophenyl)-6-(cyclopropylmethoxy)-3-pyridinecarboxylic acid (CAS Registry No. 1018782-76-7) and 2-propyl-4-thiazolemethanamine as starting materials, LC-MS (UV peak area/ESI) 99%, 442.134 (M+H)⁺.

Example 12

Preparation of 5-(4-chloro-phenyl)-6-(2,2,2-trifluoro-ethoxy)-N-(5-trifluoromethyl-[1,2,4]oxadiazol-3-ylmethyl)-nicotinamide

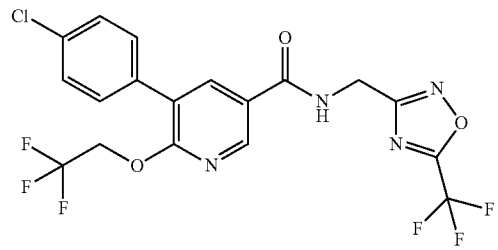 [SMILES: O=C(NCc1noc(C(F)(F)F)n1)c1cnc(OCC(F)(F)F)c(-c2ccc(Cl)cc2)c1]

The title compound was synthesized in analogy to Example 1, using 5-(4-chloro-phenyl)-6-(2,2,2-trifluoroethoxy)-nicotinic acid (CAS Registry No. 1018782-82-5) and C-(5-trifluoromethyl-[1,2,4]oxadiazol-3-yl)-methylamine hydrochloride (example AI), LC-MS (UV peak area/ESI) 93%, 479.035 (M–H)⁻.

Example 13

Preparation of 4-(4-chloro-phenyl)-5-cyclopropylmethoxy-pyrimidine-2-carboxylic acid (5-cyclopropyl-[1,2,4]oxadiazol-3-ylmethyl)-amide

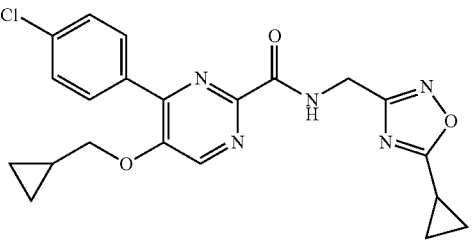 [SMILES: O=C(NCc1noc(C2CC2)n1)c1ncc(OCC2CC2)c(-c2ccc(Cl)cc2)n1]

The title compound was synthesized in analogy to Example 1, using 4-(4-chloro-phenyl)-5-cyclopropylmethoxy-pyrimidine-2-carboxylic acid (example T) and [(5-cyclopropyl-1,2,4-oxadiazol-3-yl)methyl]amine (CAS Registry No. 1082420-52-7), LC-MS (UV peak area/ESI) 100%, 426.132 (M+H)⁺.

Example 14

Preparation of 5-(4-chloro-phenyl)-N-(1-propyl-1H-pyrazol-3-ylmethyl)-6-(2,2,2-trifluoro-ethoxy)-nicotinamide

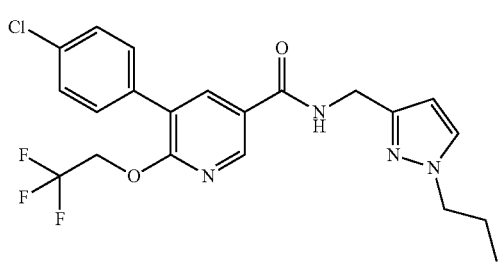 [SMILES: CCCn1ccc(CNC(=O)c2cnc(OCC(F)(F)F)c(-c3ccc(Cl)cc3)c2)n1]

The title compound was synthesized in analogy to Example 1, using 5-(4-chloro-phenyl)-6-(2,2,2-trifluoroethoxy)-nicotinic acid (CAS Registry No. 1018782-82-5) and 1-propyl-1H-pyrazole-3-methanamine (CAS Registry No. 1006333-47-6) as starting materials, LC-MS (UV peak area/ESI) 96%, 453.29 (M+H)⁺.

Example 15

Preparation of 5-(4-chloro-phenyl)-6-(2,2,2-trifluoro-ethoxy)-N-(3-trifluoromethyl-[1,2,4]oxadiazol-5-ylmethyl)-nicotinamide

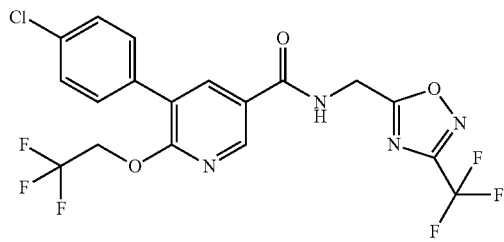 [SMILES: O=C(NCc1nc(C(F)(F)F)no1)c1cnc(OCC(F)(F)F)c(-c2ccc(Cl)cc2)c1]

The title compound was synthesized in analogy to Example 1, using 5-(4-chloro-phenyl)-6-(2,2,2-trifluoro-ethoxy)-nicotinic acid (CAS Registry No. 1018782-82-5) and C-(3-trifluoromethyl-[1,2,4]oxadiazol-5-yl)-methylamine hydrochloride (CAS registry No. 944905-93-5; example AK) as starting materials, LC-MS (UV peak area/ESI) 100%, 479.0355 (M+H)⁺.

Example 16

Preparation of 4-(4-chloro-phenyl)-5-(2,2,2-trifluoro-ethoxy)-pyrimidine-2-carboxylic acid (3-trifluoromethyl-[1,2,4]oxadiazol-5-ylmethyl)-amide

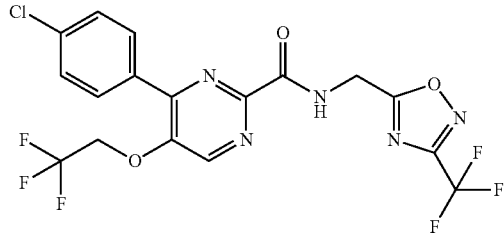 [SMILES: O=C(NCc1nc(C(F)(F)F)no1)c1ncc(OCC(F)(F)F)c(-c2ccc(Cl)cc2)n1]

The title compound was synthesized in analogy to Example 1, using 4-(4-chloro-phenyl)-5-(2,2,2-trifluoro-ethoxy)-pyrimidine-2-carboxylic acid (example W) and C-(3-trifluoromethyl-[1,2,4]oxadiazol-5-yl)-methylamine hydrochloride (CAS registry No. 944905-93-5; example AK) as starting materials; LC-MS (UV peak area/ESI) 100%, 482.0446 (M+H)⁺.

Example 17

Preparation of 4-(4-chloro-phenyl)-5-cyclopropyl-methoxy-pyrimidine-2-carboxylic acid (3-cyclopropyl-[1,2,4]oxadiazol-5-ylmethyl)-amide

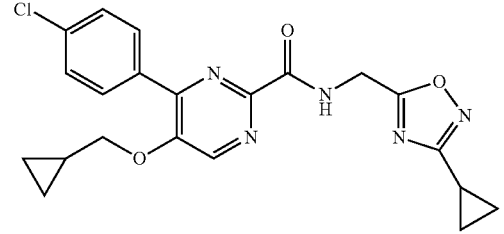 [SMILES: O=C(NCc1nc(C2CC2)no1)c1ncc(OCC2CC2)c(-c2ccc(Cl)cc2)n1]

The title compound was synthesized in analogy to Example 1, using 4-(4-chloro-phenyl)-5-cyclopropyl-methoxy-pyrimidine-2-carboxylic acid (example T) and (3-cyclopropyl-1,2,4-oxadiazol-5-yl)methane amine (CAS Registry No. 428507-31-7) as starting materials; LC-MS (UV peak area/ESI) 100%, 426.1324 (M+H)⁺.

Example 18

Preparation of 4-(4-chlorophenyl)-5-(cyclopropylmethoxy)-N-((3-(trifluoromethyl)-1,2,4-oxadiazol-5-yl)methyl)picolinamide

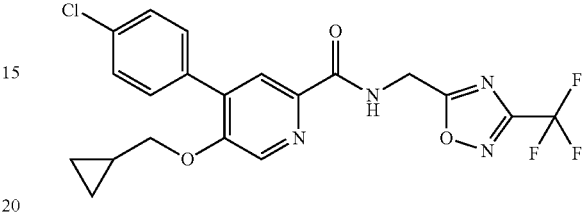

The title compound was synthesized in analogy to Example 1, using 4-(4-chloro-phenyl)-5-(cyclopropylmethyloxy)-pyridine-2-carboxylic acid (example H) and C-(3-trifluoromethyl-[1,2,4]oxadiazol-5-yl)-methylamine hydrochloride (CAS registry No. 944905-93-5; example AK) as starting materials; LC-MS (UV peak area/ESI) 100%, 453.0924 (M+H)⁺.

Example 19

Preparation of 4-(4-chlorophenyl)-N-((5-methylisoxazol-3-yl)methyl)-5-(2,2,2-trifluoro-ethoxy)picolinamide

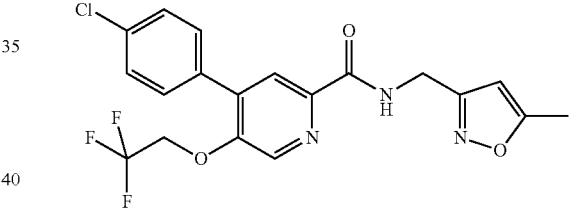

The title compound was synthesized in analogy to Example 1, using 4-(4-chloro-phenyl)-5-(2,2,2-trifluoro-ethoxy)-pyridine-2-carboxylic acid (example D) and 5-methyl-3-isoxazolemethanamine (CAS registry No. 154016-48-5) as starting materials; LC-MS (UV peak area/ESI) 100%, 426.0822 (M+H)⁺.

Example 20

Preparation of 5-(4-chloro-phenyl)-6-cyclopropyl-methoxy-pyridazine-3-carboxylic acid (3-trifluoromethyl-[1,2,4]oxadiazol-5-ylmethyl)-amide

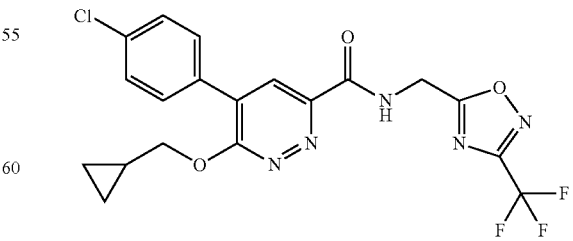

The title compound was synthesized in analogy to Example 1, using 5-(4-chloro-phenyl)-6-cyclopropyl-methoxy-pyridazine-3-carboxylic acid (example P) and C-(3-trifluoromethyl-[1,2,4]oxadiazol-5-yl)-methylamine hydrochloride (CAS registry No. 944905-93-5; example AK) as starting materials; LC-MS (UV peak area/ESI) 100%, 454.0888 (M+H)⁺.

Example 21

Preparation of 4-(4-chloro-phenyl)-5-cyclopropyl-methoxy-pyrimidine-2-carboxylic acid (3-trifluoromethyl-[1,2,4]oxadiazol-5-ylmethyl)-amide

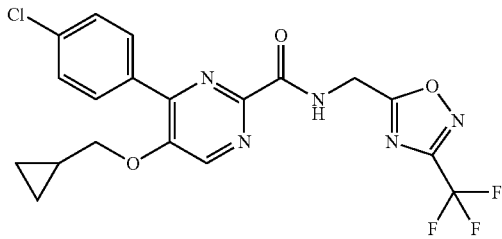 [SMILES: O=C(NCc1nc(C(F)(F)F)no1)c1ncc(OCC2CC2)c(-c2ccc(Cl)cc2)n1]

The title compound was synthesized in analogy to Example 1, using 4-(4-chloro-phenyl)-5-cyclopropyl-methoxy-pyrimidine-2-carboxylic acid (example T) and C-(3-trifluoromethyl-[1,2,4]oxadiazol-5-yl)-methylamine hydrochloride (CAS registry No. 944905-93-5; example AK) as starting materials; LC-MS (UV peak area/ESI) 100%, 454.0901 (M+H)⁺.

Example 22

Preparation of 6-(4-chloro-phenyl)-5-(2,2,2-trifluoro-ethoxy)-pyridine-2-carboxylic acid (3-trifluoromethyl-[1,2,4]oxadiazol-5-ylmethyl)-amide

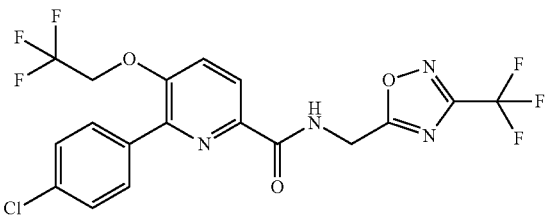 [SMILES: O=C(NCc1nc(C(F)(F)F)no1)c1ccc(OCC(F)(F)F)c(-c2ccc(Cl)cc2)n1]

The title compound was synthesized in analogy to Example 1, using 6-(4-chloro-phenyl)-5-(2,2,2-trifluoro-ethoxy)-pyridine-2-carboxylic acid (example AF) and C-(3-trifluoromethyl-[1,2,4]oxadiazol-5-yl)-methylamine hydrochloride (CAS registry No. 944905-93-5; example AK) as starting materials; LC-MS (UV peak area/ESI) 100%, 479.0355 (M−H)⁻.

Example 23

Preparation of 5-(4-chlorophenyl)-N-((3-methoxy-isoxazol-5-yl)methyl)-6-(2,2,2-trifluoroethoxy)pyridazine-3-carboxamide

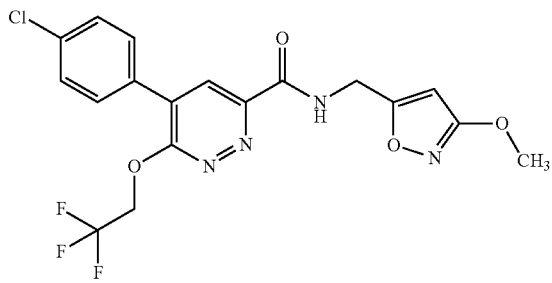 [SMILES: COc1cc(CNC(=O)c2cc(-c3ccc(Cl)cc3)c(OCC(F)(F)F)nn2)on1]

The title compound was synthesized in analogy to Example 1, using 5-(4-chloro-phenyl)-6-(2,2,2-trifluoro-ethoxy)-pyridazine-3-carboxylic acid (example M) and 3-methoxy-5-isoxazole-methanamine hydrochloride as starting materials, 443.1 (M+H)⁺.

Example 24

Preparation of (S)-5-(4-chlorophenyl)-N-((3-methoxyisoxazol-5-yl)methyl)-6-(1,1,1-trifluoropropan-2-yloxy)pyridazine-3-carboxamide

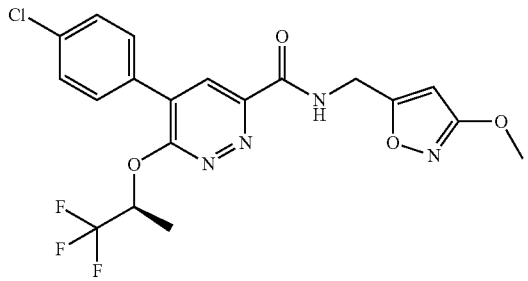 [SMILES: COc1cc(CNC(=O)c2cc(-c3ccc(Cl)cc3)c(O[C@@H](C)C(F)(F)F)nn2)on1]

The title compound was synthesized in analogy to Example 1, using 5-(4-chloro-phenyl)-6-((S)-2,2,2-trifluoro-1-methyl-ethoxy)-pyridazine-3-carboxylic acid (example AG) and 3-methoxy-5-isoxazole-methanamine hydrochloride as starting materials, 457.1 (M+H)⁺.

Example 25

Preparation of 4-(3,4-dichlorophenyl)-N-((3-methoxyisoxazol-5-yl)methyl)-5-(2,2,2-trifluoroethoxy)pyrimidine-2-carboxamide

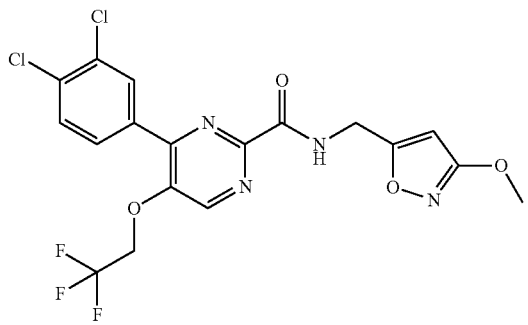 [SMILES: COc1cc(CNC(=O)c2ncc(OCC(F)(F)F)c(-c3ccc(Cl)c(Cl)c3)n2)on1]

The title compound was synthesized in analogy to Example 1, using 4-(3,4-dichloro-phenyl)-5-(2,2,2-trifluoro-ethoxy)-pyrimidine-2-carboxylic acid (example AA) and 3-methoxy-5-isoxazolemethanamine hydrochloride as starting materials, 477.0 (M+H)⁺.

Example 26

Preparation of N-(4-Chloro-1-methyl-1H-pyrazol-3-ylmethyl)-5-(4-chloro-phenyl)-6-(2,2,2-trifluoro-ethoxy)-nicotinamide

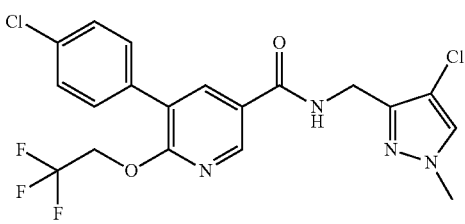 [SMILES: Cn1cc(Cl)c(CNC(=O)c2cnc(OCC(F)(F)F)c(-c3ccc(Cl)cc3)c2)n1]

The title compound was synthesized in analogy to Example 1, using 5-(4-chloro-phenyl)-6-(2,2,2-trifluoro-ethoxy)-nicotinic acid (CAS Registry No. 1018782-82-5) and [(4-chloro-1-methyl-1H-pyrazol-3-yl)methyl]amine (CAS Registry No. 1017785-44-2) as starting materials; LC-MS (UV peak area/ESI) 100%, 458.0604 (M+H)⁺.

Example 27

Preparation of 4-(4-chlorophenyl)-N-((5-isopropyl-isoxazol-3-yl)methyl)-5-(2,2,2-trifluoroethoxy)picolinamide

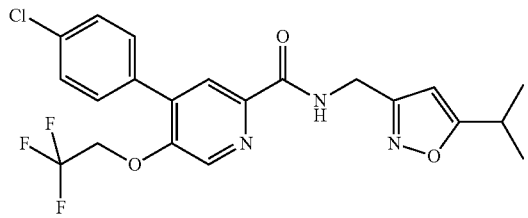

The title compound was synthesized in analogy to Example 1, using 4-(4-chloro-phenyl)-5-(2,2,2-trifluoroethoxy)-pyridine-2-carboxylic acid (example D) and 5-(1-methylethyl)-3-isoxazolemethanamine (CAS Registry No. 154016-49-6) as starting materials; LC-MS (UV peak area/ESI) 98.5%, 454.1122 (M+H)+.

Example 28

Preparation of 4-(4-chlorophenyl)-N-((5-cyclopropylisoxazol-3-yl)methyl)-5-(2,2,2-trifluoroethoxy)picolinamide

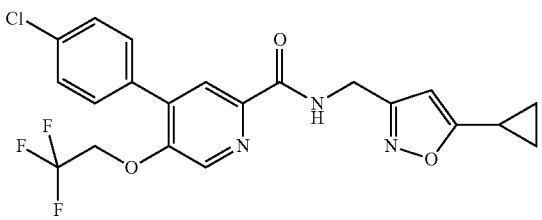 [SMILES: O=C(NCc1cc(C2CC2)on1)c1cc(-c2ccc(Cl)cc2)c(OCC(F)(F)F)cn1]

The title compound was synthesized in analogy to Example 1, using 4-(4-chloro-phenyl)-5-(2,2,2-trifluoroethoxy)-pyridine-2-carboxylic acid (example D) and 5-cyclopropyl-3-isoxazolemethanamine (CAS Registry No. 1060817-49-3) as starting materials; LC-MS (UV peak area/ESI) 98.6%, 452.0979 (M+H)+.

Example 29

Preparation of (S)-6-(4-chlorophenyl)-N-((3-methoxyisoxazol-5-yl)methyl)-5-(1,1,1-trifluoropropan-2-yloxy)pyrazine-2-carboxamide

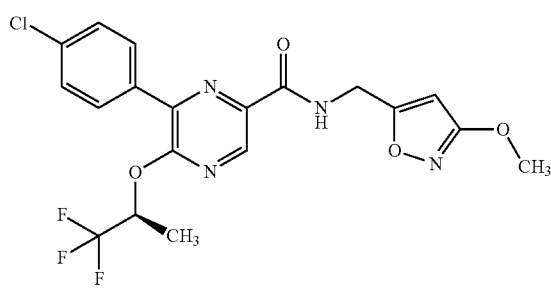 [SMILES: COc1cc(CNC(=O)c2cnc(O[C@@H](C)C(F)(F)F)c(-c3ccc(Cl)cc3)n2)on1]

The title compound was synthesized in analogy to Example 1, using (S)-6-(4-chlorophenyl)-5-(1,1,1-trifluoropropan-2-yloxy)pyrazine-2-carboxylic acid (example AG) and 3-methoxy-5-isoxazolemethanamine hydrochloride as starting materials, 455.1 (M+H)+.

Example 30

Preparation of 5-(4-chloro-phenyl)-N-(5-cyclopropyl-isoxazol-3-ylmethyl)-6-cyclopropyl-methoxy-nicotinamide

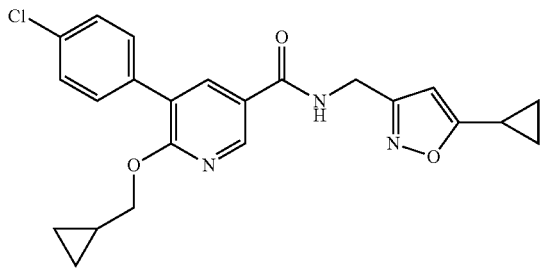 [SMILES: O=C(NCc1cc(C2CC2)on1)c1cnc(OCC2CC2)c(-c2ccc(Cl)cc2)c1]

The title compound was synthesized in analogy to Example 1, using 5-(4-chloro-phenyl)-6-cyclopropyl-methoxy-nicotinic acid (CAS Registry No. 1018782-76-7) and 5-aminomethyl-3 cyclopropylisoxazole (CAS registry No. 851434-73-6) as starting materials, 424.1 (M+H)+.

Example 31

Preparation of 5-(4-chlorophenyl)-N-((5-isopropyl-isoxazol-3-yl)methyl)-6-(2,2,2-trifluoroethoxy)nicotinamide

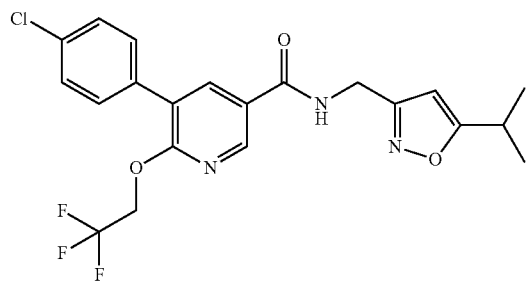 [SMILES: CC(C)c1cc(CNC(=O)c2cnc(OCC(F)(F)F)c(-c3ccc(Cl)cc3)c2)no1]

The title compound was synthesized in analogy to Example 1, using 5-(4-chloro-phenyl)-6-(2,2,2-trifluoroethoxy)-nicotinic acid (CAS Registry No. 1018782-82-5) and 5-(1-methylethyl)-3-isoxazolemethanamine (CAS Registry No. 154016-49-6) as starting materials, 454.1 (M+H)+.

Example 32

Preparation of 5-(4-chlorophenyl)-6-(cyclopropylmethoxy)-N-((5-isopropylisoxazol-3-yl)methyl)nicotinamide

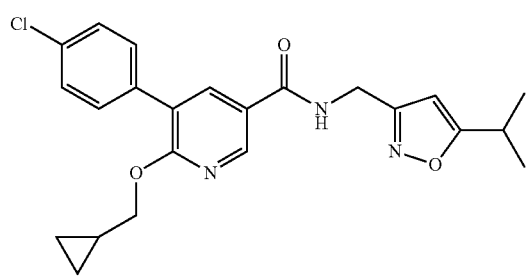 [SMILES: CC(C)c1cc(CNC(=O)c2cnc(OCC3CC3)c(-c3ccc(Cl)cc3)c2)no1]

The title compound was synthesized in analogy to Example 1, using 5-(4-chloro-phenyl)-6-cyclopropyl-methoxy-nicotinic acid (CAS Registry No. 1018782-76-7) and 5-(1-methylethyl)-3-isoxazolemethanamine (CAS Registry No. 154016-49-6) as starting materials, 426.2 (M+H)+.

Example 33

Preparation of 4-(4-chlorophenyl)-N-((3-cyclopropylisoxazol-5-yl)methyl)-5-(2,2,2-trifluoroethoxy)picolinamide

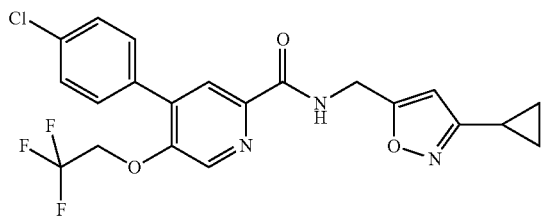 [SMILES: O=C(NCc1cc(C2CC2)no1)c1cc(-c2ccc(Cl)cc2)c(OCC(F)(F)F)cn1]

The title compound was synthesized in analogy to Example 1, using 4-(4-chloro-phenyl)-5-(2,2,2-trifluoroethoxy)-pyridine-2-carboxylic acid (example D) and 3-cyclopropyl-5-isoxazolemethanamine (CAS Registry No. 851434-73-6) as starting materials; LC-MS (UV peak area/ESI) 97.6%, 452.0973 (M+H)$^+$.

Example 34

Preparation of (S)-5-(4-chlorophenyl)-N-((3-methoxyisoxazol-5-yl)methyl)-6-(1,1,1-trifluoropropan-2-yloxy)nicotinamide

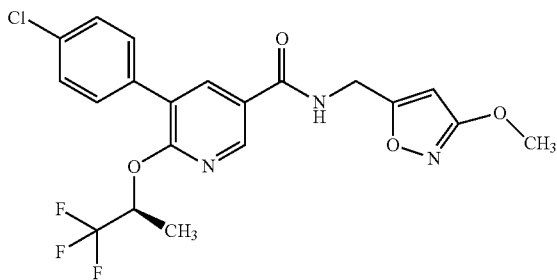 [SMILES: COc1cc(CNC(=O)c2cnc(O[C@@H](C)C(F)(F)F)c(-c3ccc(Cl)cc3)c2)on1]

The title compound was synthesized in analogy to Example 1, using (S)-5-(4-chlorophenyl)-6-(1,1,1-trifluoropropan-2-yloxy)nicotinic acid (Example AO) and 3-methoxy-5-isoxazolemethanamine hydrochloride as starting materials. MS: 456.1 (M+H)$^+$.

Example 35

Preparation of (S)-4-(4-chlorophenyl)-N-((3-(trifluoromethyl)-1,2,4-oxadiazol-5-yl)methyl)-5-(1,1,1-trifluoropropan-2-yloxy)pyrimidine-2-carboxamide

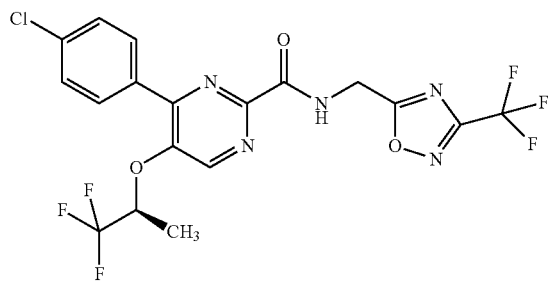 [SMILES: C[C@H](Oc1cnc(C(=O)NCc2nc(C(F)(F)F)no2)nc1-c1ccc(Cl)cc1)C(F)(F)F]

The title compound was synthesized in analogy to Example 1, using (S)-4-(4-chlorophenyl)-5-(1,1,1-trifluoropropan-2-yloxy)pyrimidine-2-carboxylic acid (Example AQ) and C-(3-trifluoromethyl-[1,2,4]oxadiazol-5-yl)-methylamine hydrochloride (CAN 944905-93-5; example AK) as starting materials. MS: 496.1 (M+H)$^+$.

Example 36

Preparation of (S)-6-(4-chlorophenyl)-N-((3-(trifluoromethyl)-1,2,4-oxadiazol-5-yl)methyl)-5-(1,1,1-trifluoropropan-2-yloxy)pyrazine-2-carboxamide

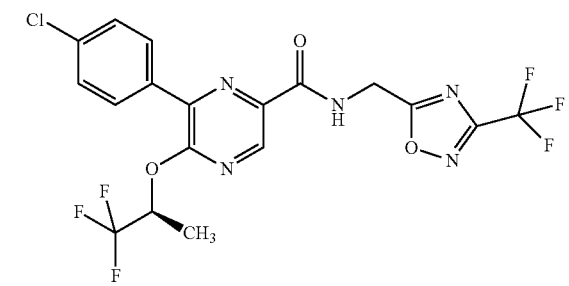 [SMILES: C[C@H](Oc1ncc(C(=O)NCc2nc(C(F)(F)F)no2)nc1-c1ccc(Cl)cc1)C(F)(F)F]

The title compound was synthesized in analogy to Example 1, using (S)-6-(4-chlorophenyl)-5-(1,1,1-trifluoropropan-2-yloxy)pyrazine-2-carboxylic acid (example AG) and C-(3-trifluoromethyl-[1,2,4]oxadiazol-5-yl)-methylamine hydrochloride (CAN 944905-93-5; example AK) as starting materials. MS: 494.0 (M−H)$^-$.

Example 37

Preparation of (S)-4-(4-chlorophenyl)-N-((3-methoxyisoxazol-5-yl)methyl)-5-(1,1,1-trifluoropropan-2-yloxy)picolinamide

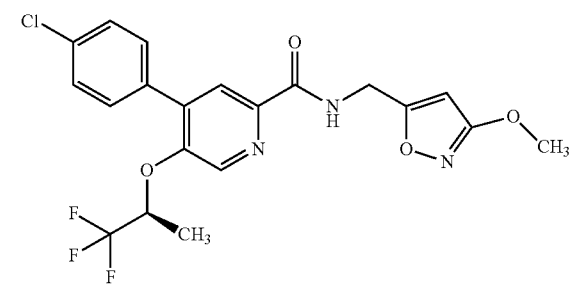 [SMILES: COc1cc(CNC(=O)c2cc(-c3ccc(Cl)cc3)c(O[C@@H](C)C(F)(F)F)cn2)on1]

The title compound was synthesized in analogy to Example 1, using (S)-4-(4-chlorophenyl)-5-(1,1,1-trifluoropropan-2-yloxy)picolinic acid (example AR) and 3-methoxy-5-isoxazolemethanamine hydrochloride as starting materials. MS: 456.1 (M+H)$^+$.

Example 38

Preparation of (S)-5-(4-chlorophenyl)-N-((3-(trifluoromethyl)-1,2,4-oxadiazol-5-yl)methyl)-6-(1,1,1-trifluoropropan-2-yloxy)nicotinamide

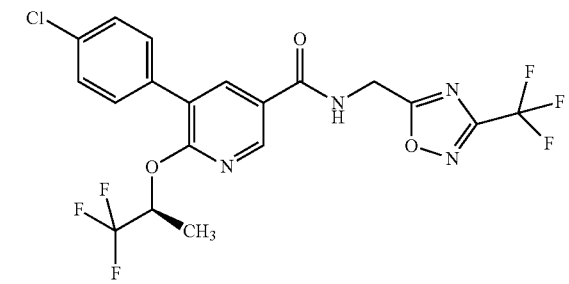 [SMILES: C[C@H](Oc1ncc(C(=O)NCc2nc(C(F)(F)F)no2)cc1-c1ccc(Cl)cc1)C(F)(F)F]

The title compound was synthesized in analogy to Example 1, using (S)-5-(4-chlorophenyl)-6-(1,1,1-trifluoropropan-2-yloxy)nicotinic acid (Example AO) and C-(3-trifluoromethyl-[1,2,4]oxadiazol-5-yl)-methylamine hydrochloride (CAS registry No. 944905-93-5; example AK) as starting materials; MS: 493.1 (M−H)⁻.

Example 39

Preparation of 4-(4-chlorophenyl)-N-((5-isopropyl-1,2,4-oxadiazol-3-yl)methyl)-5-(2,2,2-trifluoroethoxy)picolinamide

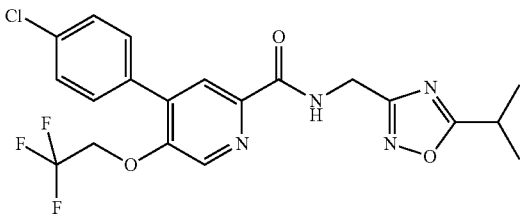

The title compound was synthesized in analogy to Example 1, using 4-(4-chloro-phenyl)-5-(2,2,2-trifluoroethoxy)-pyridine-2-carboxylic acid (example D) and 5-(1-methylethyl)-1,2,4-oxadiazole-3-methanamine, (CAN 936940-30-6) as starting materials; LC-MS (UV peak area/ESI) 100%, 455.1092 (M+H)⁺.

Example 40

Preparation of 4-(4-chlorophenyl)-N-((3-isopropyl-1,2,4-oxadiazol-5-yl)methyl)-5-(2,2,2-trifluoroethoxy)picolinamide

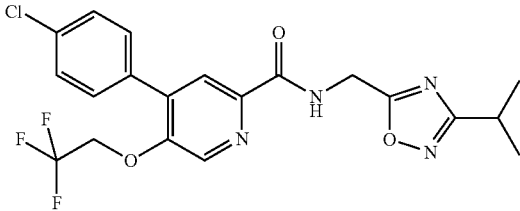 [SMILES: CC(C)c1noc(CNC(=O)c2cc(-c3ccc(Cl)cc3)c(OCC(F)(F)F)cn2)n1]

The title compound was synthesized in analogy to Example 1, using 4-(4-chloro-phenyl)-5-(2,2,2-trifluoroethoxy)-pyridine-2-carboxylic acid (example D) and 3-(1-methylethyl)-1,2,4-oxadiazole-5-methanamine (CAN 936940-67-9) as starting materials, LC-MS (UV peak area/ESI) 97.2%, 455.1099 (M+H)⁺.

Example 41

Preparation of 5-(4-chloro-phenyl)-6-(2,2,2-trifluoro-ethoxy)-pyridazine-3-carboxylic acid (5-cyclopropyl-[1,2,4]oxadiazol-3-ylmethyl)-amide

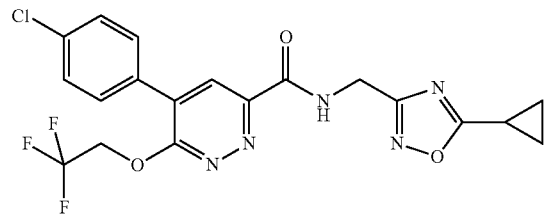 [SMILES: O=C(NCc1noc(C2CC2)n1)c1cc(-c2ccc(Cl)cc2)c(OCC(F)(F)F)nn1]

To a stirred solution of 5-(4-chloro-phenyl)-6-(2,2,2-trifluoro-ethoxy)-pyridazine-3-carboxylic acid (example M, 100 mg, 0.300 mmol) in dimethylformamide (4 mL, dried), was added 4-methylmorpholine (CAS No. 109-02-4, 0.09 ml, 0.901 mmol), HBTU (CAS No. 94790-37-1, 171 mg, 0.450 mmol), 5-cyclopropyl-[1,2,4]oxadiazol-3-methanamine hydrochloride (Chembridge, MFCD09864586, 52 mg, 0.300 mmol) at rt and this mixture was stirred for 12 h at rt. Volatile were removed under reduced pressure and the residue was extracted with ethyl acetate. The combined organic layer was washed with aq. NaHCO₃ soln, brine and concentrated to afford the crude residue which was purified by column chromatography (100-200 silica gel, elution with ethyl acetate/hexane). The title compound (91 mg, 66.0% yield) was obtained as a white solid; LC-MS (UV peak area/ESI) 96.8%, 454.6 (M+H)⁺.

Example 42

Preparation of 5-(4-chloro-phenyl)-6-(2,2,2-trifluoro-ethoxy)-pyridazine-3-carboxylic acid (5-isopropyl-isoxazol-3-ylmethyl)-amide

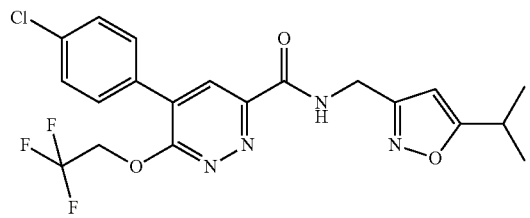 [SMILES: CC(C)c1cc(CNC(=O)c2cc(-c3ccc(Cl)cc3)c(OCC(F)(F)F)nn2)no1]

The title compound was synthesized in analogy to Example 41, using 5-(4-chloro-phenyl)-6-(2,2,2-trifluoroethoxy)-pyridazine-3-carboxylic acid (example M) and 5-(1-methylethyl)-3-isoxazolemethanamine (CAS Registry No. 154016-49-6) as starting materials; LC-MS (UV peak area/ESI) 99.1%, 455.2 (M+H)⁺.

Example 43

Preparation of 5-(4-chloro-phenyl)-6-(2,2,2-trifluoro-ethoxy)-pyridazine-3-carboxylic acid (3-isopropyl-isoxazol-5-ylmethyl)-amide

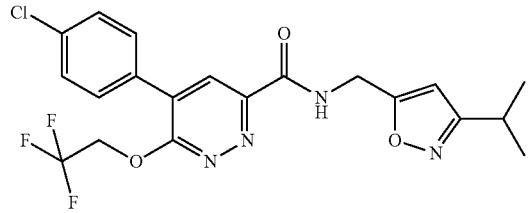 [SMILES: CC(C)c1cc(CNC(=O)c2cc(-c3ccc(Cl)cc3)c(OCC(F)(F)F)nn2)on1]

The title compound was synthesized in analogy to Example 41, using 5-(4-chloro-phenyl)-6-(2,2,2-trifluoroethoxy)-pyridazine-3-carboxylic acid (example M) and 3-(1-methylethyl)-5-isoxazolemethanamine (CAN. 543713-30-0) as starting materials, LC-MS (UV peak area/ESI) 100.0%, 455.2 (M+H)⁺.

Example 44

Preparation of 4-(4-chloro-phenyl)-5-(2,2,2-trifluoro-ethoxy)-pyrimidine-2-carboxylic acid (3-isopropyl-isoxazol-5-ylmethyl)-amide

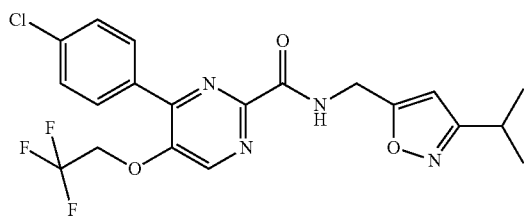 [SMILES: CC(C)c1cc(CNC(=O)c2ncc(OCC(F)(F)F)c(-c3ccc(Cl)cc3)n2)on1]

The title compound was synthesized in analogy to Example 41, using 4-(4-chloro-phenyl)-5-(2,2,2-trifluoro-ethoxy)-pyrimidine-2-carboxylic acid (example W) and 3-(1-methylethyl)-5-isoxazolemethanamine (CAN 543713-30-0) as starting materials; LC-MS (UV peak area/ESI) 98.43%, 455.0 (M+H)+.

Example 45

Preparation of 4-(4-chlorophenyl)-5-(2,2,2-trifluoro-ethoxy)-N-45-(trifluoromethyl)isoxazol-3-yl)methyl) picolinamide

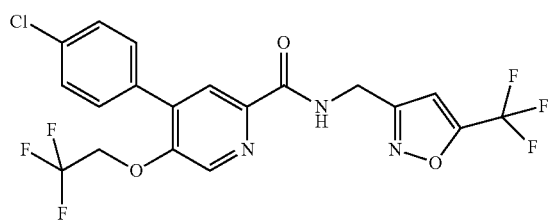 [SMILES: O=C(NCc1cc(C(F)(F)F)on1)c1cc(-c2ccc(Cl)cc2)c(OCC(F)(F)F)cn1]

The title compound was synthesized in analogy to Example 1, using 4-(4-chloro-phenyl)-5-(2,2,2-trifluoro-ethoxy)-pyridine-2-carboxylic acid (example D) and 5-trifluoromethyl-isoxazol-3-methanamine hydrochloride (example BG) as starting materials; LC-MS (UV peak area/ESI) 100%, 480.0532 (M+H)+.

Example 46

Preparation of 5-(4-chloro-phenyl)-6-(2,2,2-trifluoro-ethoxy)-pyridazine-3-carboxylic acid (3-trifluoromethyl-[1,2,4]oxadiazol-5-ylmethyl)-amide

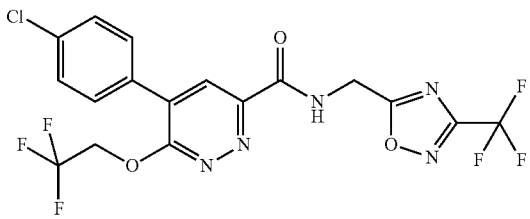 [SMILES: O=C(NCc1nc(C(F)(F)F)no1)c1cc(-c2ccc(Cl)cc2)c(OCC(F)(F)F)nn1]

The title compound was synthesized in analogy to Example 41, using 5-(4-chloro-phenyl)-6-(2,2,2-trifluoro-ethoxy)-pyridazine-3-carboxylic acid (example M) and C-(3-trifluoromethyl-[1,2,4]oxadiazol-5-yl)-methylamine hydrochloride (CAS registry No. 944905-93-5; example AK) as starting materials; LC-MS (UV peak area/ESI) 100.0%, 482.0 (M+H)+.

Example 47

Preparation of 6-(4-chloro-phenyl)-5-(2,2,2-trifluoro-ethoxy)-pyridine-2-carboxylic acid (3-cyclopropyl-isoxazol-5-ylmethyl)-amide

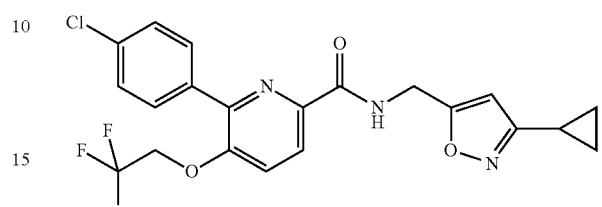

The title compound was synthesized in analogy to Example 41, using 6-(4-chloro-phenyl)-5-(2,2,2-trifluoro-ethoxy)-pyridine-2-carboxylic acid (example AF) and 3-cyclopropyl-5-isoxazolemethanamine (CAN 851434-73-6) as starting materials, LC-MS (UV peak area/ESI) 99.6%, 452.2 (M+H)+.

Example 48

Preparation of 5-(4-chloro-phenyl)-6-(2,2,2-trifluoro-ethoxy)-pyridazine-3-carboxylic acid (3-cyclopropyl-[1,2,4]oxadiazol-5-ylmethyl)-amide

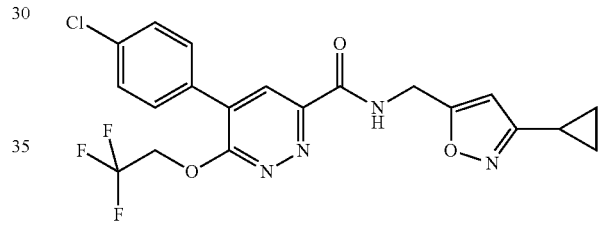

The title compound was synthesized in analogy to Example 41, using 5-(4-chloro-phenyl)-6-(2,2,2-trifluoro-ethoxy)-pyridazine-3-carboxylic acid (example M) and 3-cyclopropyl-1,2,4-oxadiazole-5-methanamine (CAS Registry No. 428507-31-7) as starting materials; LC-MS (UV peak area/ESI) 97.6%, 454.2 (M+H)+.

Example 49

Preparation of 5-(4-Chloro-phenyl)-6-(2,2,2-trifluoro-ethoxy)-pyridazine-3-carboxylic acid (3-cyclopropyl-isoxazol-5-ylmethyl)-amide

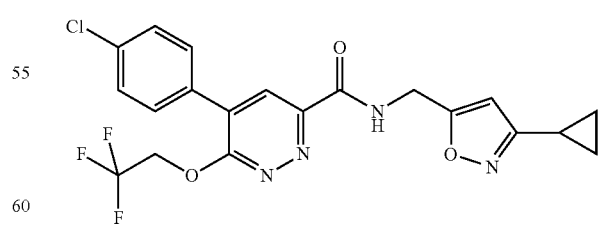

The title compound was synthesized in analogy to Example 41, using 5-(4-chloro-phenyl)-6-(2,2,2-trifluoro-ethoxy)-pyridazine-3-carboxylic acid (example M) and 3-cyclopropyl-5-isoxazolemethanamine (CAN 851434-73-6) as starting materials, LC-MS (UV peak area/ESI) 92.9%, 453.2 (M+H)+.

Example 50

Preparation of 5-(4-chloro-phenyl)-6-(2,2,2-trifluoro-ethoxy)-N-(5-trifluoromethyl-isoxazol-3-ylmethyl)-nicotinamide

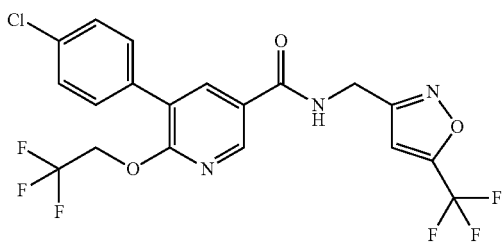 [SMILES: O=C(NCc1cc(C(F)(F)F)on1)c1cnc(OCC(F)(F)F)c(-c2ccc(Cl)cc2)c1]

The title compound was synthesized in analogy to Example 1, using 5-(4-chloro-phenyl)-6-(2,2,2-trifluoroethoxy)-nicotinic acid (CAN 1018782-82-5) and 5-trifluoromethyl-isoxazol-3-methanamine hydrochloride (example BF) as starting materials; MS: 478.0 (M+H)$^+$.

Example 51

Preparation of 5-(4-chlorophenyl)-6-cyclopropylmethoxy-N-(5-isopropyl-[1,2,4]oxadiazol-3-yl)methyl)-nicotinamide

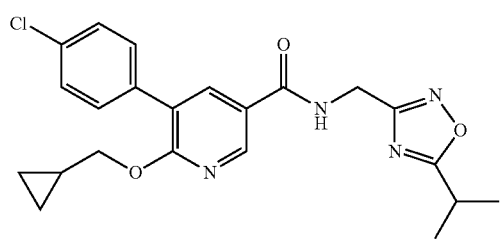 [SMILES: CC(C)c1nc(CNC(=O)c2cnc(OCC3CC3)c(-c3ccc(Cl)cc3)c2)no1]

The title compound was synthesized in analogy to Example 1, using 5-(4-chloro-phenyl)-6-(cyclopropylmethoxy)-3-pyridine carboxylic acid (CAN 1018782-76-7) and 5-(1-methylethyl)-1,2,4-oxadiazole-3-methanamine, (CAN 936940-30-6) as starting materials, MS 472.2 (M+H)$^+$.

Example 52

Preparation of 6-(4-chloro-phenyl)-5-cyclopropylmethoxy-pyridine-2-carboxylic acid (2-isopropyl-thiazol-4-ylmethyl)-amide

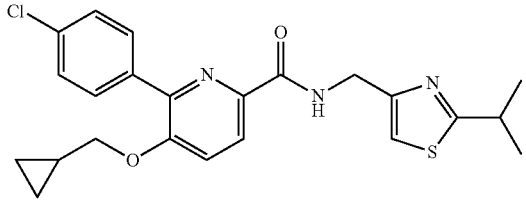 [SMILES: CC(C)c1nc(CNC(=O)c2ccc(OCC3CC3)c(-c3ccc(Cl)cc3)n2)cs1]

The title compound was synthesized in analogy to Example 41, using 6-(4-chloro-phenyl)-5-cyclopropylmethoxy-pyridine-2-carboxylic acid (example AW) and 2-(1-methylethyl)-4-thiazole-methanamine dihydrochloride (CAN 1171981-10-4) as starting materials, LC-MS (peak area/EIC) 97.9%, 442.0 (M+H)$^+$.

Example 53

Preparation of 6-(4-chloro-phenyl)-5-(2,2,2-trifluoro-ethoxy)-pyridine-2-carboxylic acid (5-isopropyl-isoxazol-3-ylmethyl)-amide

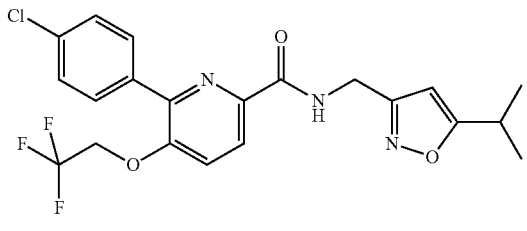 [SMILES: CC(C)c1cc(CNC(=O)c2ccc(OCC(F)(F)F)c(-c3ccc(Cl)cc3)n2)no1]

The title compound was synthesized in analogy to Example 41, using 6-(4-chloro-phenyl)-5-(2,2,2-trifluoroethoxy)-pyridine-2-carboxylic acid (example AF) and 5-(1-methylethyl)-3-isoxazolemethanamine (CAN 154016-49-6) as starting materials; LC-MS (UV peak area/ESI) 97.1%, 454.6 (M+H)$^+$.

Example 54

Preparation of N-((2-tert-butylthiazol-4-yl)methyl)-4-(4-chlorophenyl)-5-(cyclopropylmethoxy)picolinamide

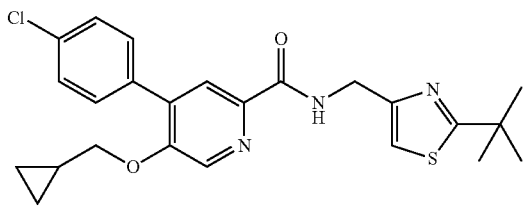 [SMILES: CC(C)(C)c1nc(CNC(=O)c2cc(-c3ccc(Cl)cc3)c(OCC3CC3)cn2)cs1]

The title compound was synthesized in analogy to Example 1, using 4-(4-chloro-phenyl)-5-(cyclopropylmethyloxy)-pyridine-2-carboxylic acid (example H) and 2-(1,1-dimethylethyl)-4-thiazolemethanamine(CAN 937656-81-0) as starting materials; LC-MS (UV peak area/ESI) 100%, 456.1491 (M+H)$^+$.

Example 55

Preparation of 6-(4-chloro-phenyl)-5-cyclopropylmethoxy-pyridine-2-carboxylic acid (5-isopropyl-isoxazol-3-ylmethyl)-amide

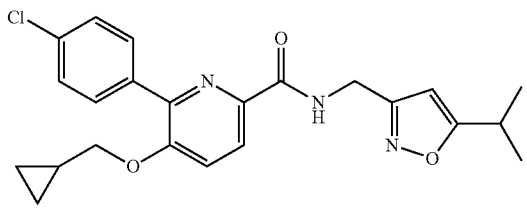

The title compound was synthesized in analogy to Example 41 using 6-(4-Chloro-phenyl)-5-cyclopropylmethoxy-pyridine-2-carboxylic acid (example AW) and 5-(1-methylethyl)-3-isoxazolemethanamine (CAN 154016-49-6) as starting materials, LC-MS (peak area/EIC) 98.2%, 426.4 (M+H)$^+$.

Example 56

Preparation of 6-(4-chloro-phenyl)-5-cyclopropyl-methoxy-pyridine-2-carboxylic acid (2-cyclopropyl-oxazol-4-ylmethyl)-amide

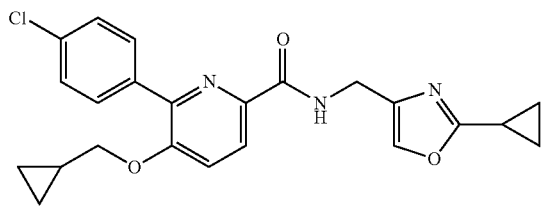 [SMILES: O=C(NCc1coc(C2CC2)n1)c1ccc(OCC2CC2)c(-c2ccc(Cl)cc2)n1]

The title compound was synthesized in analogy to Example 41, using 6-(4-Chloro-phenyl)-5-cyclopropyl-methoxy-pyridine-2-carboxylic acid (example AW) and 2-cyclopropyl-4-oxazolmethanamine (example BH) as starting materials, LC-MS (UV peak area/ESI) 97.6%, 424.0 (M+H)$^+$.

Example 57

Preparation of 6-(4-chloro-phenyl)-5-cyclopropyl-methoxy-pyridine-2-carboxylic acid (2-cyclopropyl-thiazol-4-ylmethyl)-amide

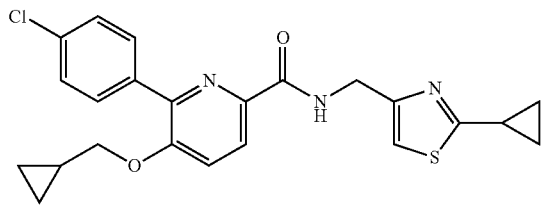

The title compound was synthesized in analogy to Example 41 using 6-(4-Chloro-phenyl)-5-cyclopropyl-methoxy-pyridine-2-carboxylic acid (example AW) and 2-cyclopropyl-4-thiazolemethanamine (CAN. 1083299-53-9) as starting materials, LC-MS (UV peak area/ESI) 95.5%, 440.2 (M+H)$^+$.

Example 58

Preparation of 6-(4-chloro-phenyl)-5-cyclopropyl-methoxy-pyridine-2-carboxylic acid (5-trifluoromethyl-isoxazol-3-ylmethyl)-amide

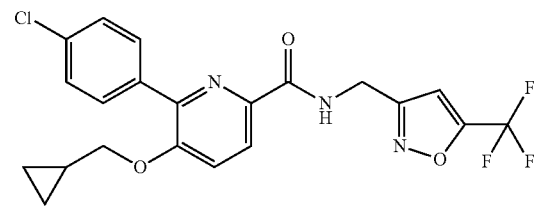 [SMILES: O=C(NCc1cc(C(F)(F)F)on1)c1ccc(OCC2CC2)c(-c2ccc(Cl)cc2)n1]

The title compound was synthesized in analogy to Example 41 using 6-(4-Chloro-phenyl)-5-cyclopropyl-methoxy-pyridine-2-carboxylic acid (example AW) and 5-trifluoromethyl-isoxazol-3-methanamine hydrochloride (example BF) as starting materials, LC-MS (UV peak area/ESI) 97.8%, 452.4 (M+H)$^+$.

Example 59

Preparation of 5-(4-chloro-phenyl)-6-(2,2,2-trifluoro-ethoxy)-N-(3-trifluoromethyl-isoxazol-5-ylmethyl)-nicotinamide

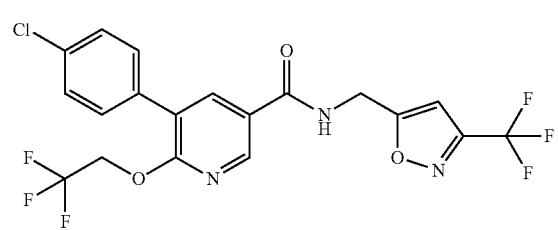

The title compound was synthesized in analogy to Example 1 using 5-(4-chloro-phenyl)-6-(2,2,2-trifluoro-ethoxy)-nicotinic acid (CAS Registry No. 1018782-82-5) and 3-trifluoromethyl-isoxazol-5-methanamine (example BA) as starting materials; MS: 478.0 (M+H)$^+$.

Example 60

Preparation of 5-(4-chloro-phenyl)-6-(2,2,2-trifluoro-ethoxy)-pyridazine-3-carboxylic acid (3-trifluoromethyl-isoxazol-5-ylmethyl)-amide

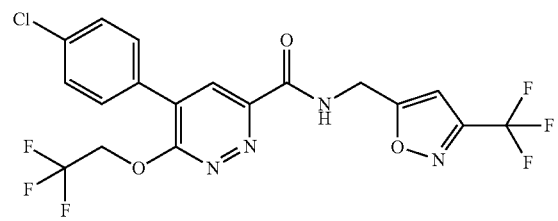 [SMILES: O=C(NCc1cc(C(F)(F)F)no1)c1cnc(OCC(F)(F)F)c(-c2ccc(Cl)cc2)c1]

The title compound was synthesized in analogy to Example 1, using 5-(4-chloro-phenyl)-6-(2,2,2-trifluoro-ethoxy)-pyridazine-3-carboxylic acid (example M) and 3-trifluoromethyl-isoxazol-5-methanamine (example BA) as starting materials; MS: 480.0 (M)$^+$.

Example 61

Preparation of 4-(4-chloro-phenyl)-5-(2,2,2-trifluoro-ethoxy)-pyrimidine-2-carboxylic acid (3-trifluoromethyl-isoxazol-5-ylmethyl)-amide

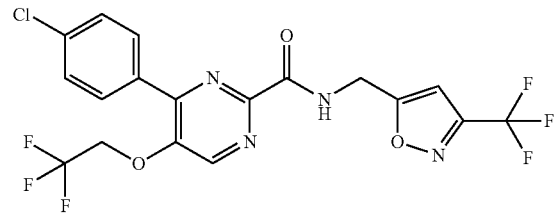 [SMILES: O=C(NCc1cc(C(F)(F)F)no1)c1ncc(OCC(F)(F)F)c(-c2ccc(Cl)cc2)n1]

The title compound was synthesized in analogy to Example 1, using 4-(4-chloro-phenyl)-5-(2,2,2-trifluoro-ethoxy)-pyrimidine-2-carboxylic acid (example AA) and 3-trifluoromethyl-isoxazol-5-methanamine (example BA) as starting materials; MS: 481.0 (M+H)⁺.

Example 62

Preparation of 4-(4-chloro-phenyl)-5-cyclopropyl-methoxy-pyrimidine-2-carboxylic acid (3-trifluoromethyl-isoxazol-5-ylmethyl)-amide

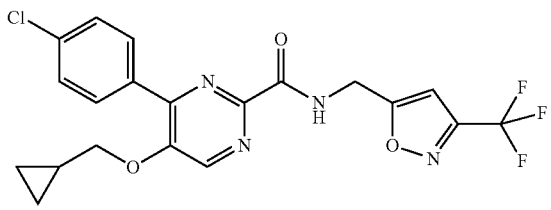 [SMILES: O=C(NCc1cc(C(F)(F)F)no1)c1ncc(OCC2CC2)c(-c2ccc(Cl)cc2)n1]

The title compound was synthesized in analogy to Example 1, using 4-(4-chloro-phenyl)-5-cyclopropyl-methoxy-pyrimidine-2-carboxylic acid (example T) and 3-trifluoromethyl-isoxazol-5-methanamine (example BA) as starting materials; MS: 453.1 (M+H)⁺.

Example 63

Preparation of 6-(4-chloro-phenyl)-5-cyclopropyl-methoxy-pyridine-2-carboxylic acid (2-tert-butyl-thiazol-4-ylmethyl)-amide

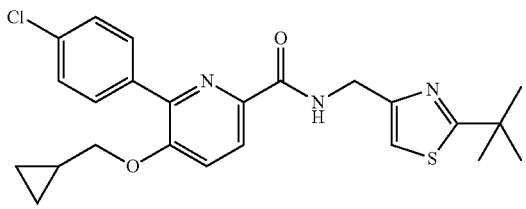 [SMILES: CC(C)(C)c1nc(CNC(=O)c2ccc(OCC3CC3)c(-c3ccc(Cl)cc3)n2)cs1]

The title compound was synthesized in analogy to Example 41, using 6-(4-Chloro-phenyl)-5-cyclopropyl-methoxy-pyridine-2-carboxylic acid (example AW) and 2-(1,1-dimethylethyl)-4-thiazolemethanamine (CAN 937656-81-0) as starting materials; LC-MS (UV peak area/ESI) 97.7%, 456.0 (M+H)⁺.

Example 64

Preparation of 6-(4-chloro-phenyl)-5-(2,2,2-trifluoro-ethoxy)-pyridine-2-carboxylic acid (3-isopropyl-isoxazol-5-ylmethyl)-amide

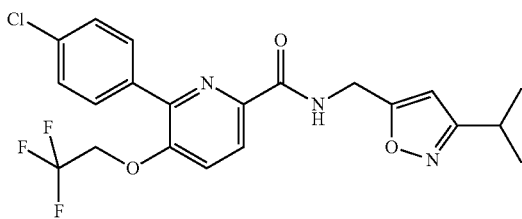 [SMILES: CC(C)c1cc(CNC(=O)c2ccc(OCC(F)(F)F)c(-c3ccc(Cl)cc3)n2)on1]

The title compound was synthesized in analogy to Example 41 using 6-(4-chloro-phenyl)-5-(2,2,2-trifluoro-ethoxy)-2-pyridine carboxylic acid (example AF) and 3-(1-methylethyl)-5-isoxazolemethanamine (CAN 543713-30-0) as starting materials; LC-MS (UV peak area/ESI) 100.0%, 454.4 (M+H)⁺.

Example 65

Preparation of 5-(4-chloro-phenyl)-6-(2,2,2-trifluoro-ethoxy)-pyridazine-3-carboxylic acid (2-tert-butyl-thiazol-4-ylmethyl)-amide

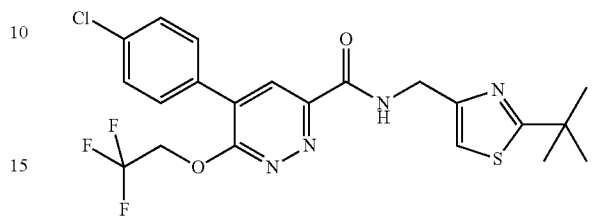

The title compound was synthesized in analogy to Example 41 using 5-(4-chloro-phenyl)-6-(2,2,2-trifluoro-ethoxy)-pyridazine-3-carboxylic acid (example M) and 2-(1,1-dimethylethyl)-4-thiazolemethanamine (CAS Registry No. 937656-81-0) as starting materials; LC-MS (UV peak area/ESI) 99.1%, 485.2 (M+H)⁺.

Example 66

Preparation of 5-(4-chloro-phenyl)-6-cyclopropyl-methoxy-N-(5-trifluoromethyl-isoxazol-3-ylmethyl)-nicotinamide

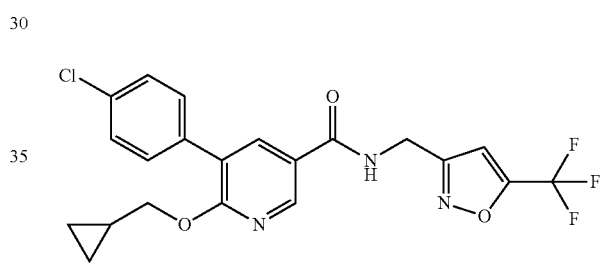

The title compound was synthesized in analogy to Example 1 using 5-(4-chlorophenyl)-6-(cyclopropyl-methoxy)-3-pyridinecarboxylic acid (CAN 1018782-76-7) and 5-trifluoromethyl-isoxazol-3-methanamine (example BF) as starting materials; LC-MS (UV peak area/ESI) 98%, 452.0975 (M+H)⁺.

Example 67

Preparation of 5-(4-chloro-phenyl)-6-(2,2,2-trifluoro-ethoxy)-pyridazine-3-carboxylic acid (5-trifluoromethyl-isoxazol-3-ylmethyl)-amide

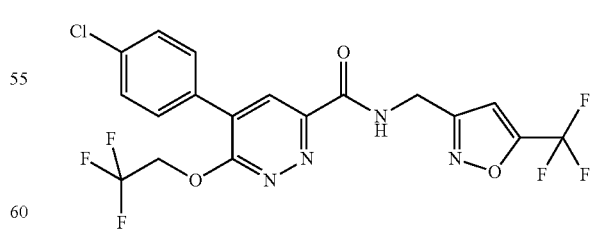

The title compound was synthesized in analogy to Example 41 using 5-(4-chlorophenyl)-6-(2,2,2-trifluoro-ethoxy)-pyridazine-3-carboxylic acid (example M) and 5-trifluoromethyl-isoxazol-3-methanamine (example BF) as starting materials; LC-MS (UV peak area/ESI), 94.3%, 481.3 (M+H)⁺.

Example 68

Preparation of (S)-4-(4-chlorophenyl)-N-((3-(trifluoromethyl)isoxazol-5-yl)methyl)-5-(1,1,1-trifluoropropan-2-yloxy)pyrimidine-2-carboxamide

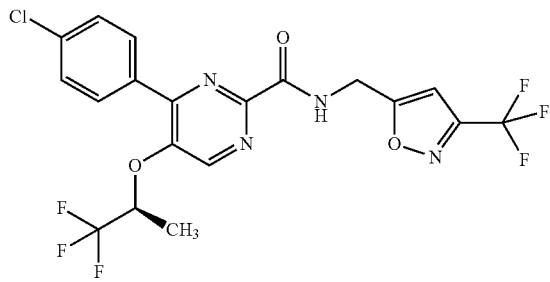 [SMILES: C[C@H](Oc1cnc(C(=O)NCc2cc(C(F)(F)F)no2)nc1-c1ccc(Cl)cc1)C(F)(F)F]

The title compound was synthesized in analogy to Example 1 using (S)-4-(4-chlorophenyl)-5-(1,1,1-trifluoropropan-2-yloxy)pyrimidine-2-carboxylic acid (example AQ) and 3-trifluoromethyl-isoxazol-5-methanamine (example BA) as starting materials; LC-MS (UV peak area/ESI) 100%, 495.0965 (M+H)$^+$.

Example 69

Preparation of (S)-6-(4-chlorophenyl)-N-(pyridin-2-ylmethyl)-5-(1,1,1-trifluoropropan-2-yloxy)pyrazine-2-carboxamide

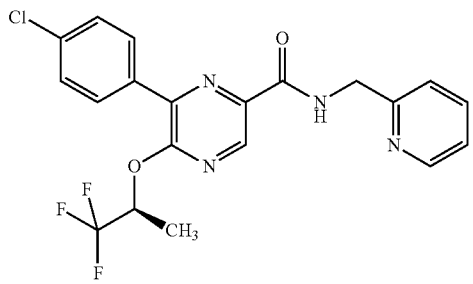 [SMILES: C[C@H](Oc1ncc(C(=O)NCc2ccccn2)nc1-c1ccc(Cl)cc1)C(F)(F)F]

The title compound was synthesized in analogy to Example 1 using (S)-6-(4-chlorophenyl)-5-(1,1,1-trifluoropropan-2-yloxy)pyrazine-2-carboxylic acid (example AH) and 2-pyridinemethanamine (CAN 3731-51-9) as starting materials; MS (ESI): 437.1 (M+H)$^+$.

Example 70

Preparation of 4-(4-chlorophenyl)-N-((2-cyclopropyloxazol-4-yl)methyl)-5-(2,2,2-trifluoroethoxy)picolinamide

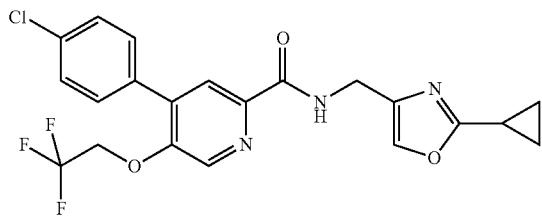 [SMILES: O=C(NCc1coc(C2CC2)n1)c1cc(-c2ccc(Cl)cc2)c(OCC(F)(F)F)cn1]

The title compound was synthesized in analogy to Example 1 using 4-(4-chlorophenyl)-5-(2,2,2-trifluoroethoxy)-pyridine-2-carboxylic acid (example D) and 2-cyclopropyl-oxazol-4-methanamine (example BH) as starting materials; LC-MS (UV peak area/ESI) 96.5%, 452.0987 (M+H)$^+$.

Example 71

Preparation of 5-(4-chloro-3-methylphenyl)-N-((2-cyclopropylthiazol-4-yl)methyl)-6-(2,2,2-trifluoroethoxy)nicotinamide

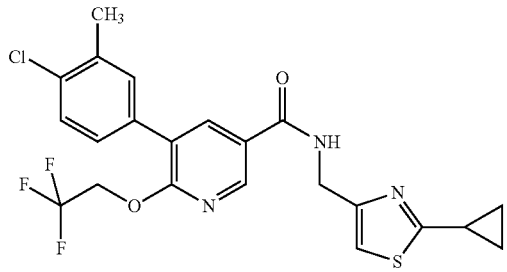 [SMILES: Cc1cc(-c2cc(C(=O)NCc3csc(C4CC4)n3)cnc2OCC(F)(F)F)ccc1Cl]

The title compound was synthesized in analogy to Example 1 using 5-(4-chloro-3-methylphenyl)-6-(2,2,2-trifluoroethoxy)nicotinic acid (example BJ) and 2-cyclopropyl-4-thiazolemethanamine (CAN 1083299-53-9) as starting materials; LC-MS (UV peak area/ESI) 95.4%, 482.09 (M+H)$^+$.

Example 72

Preparation of 5-(4-chloro-3-methylphenyl)-6-(2,2,2-trifluoroethoxy)-N-((3-(trifluoromethyl)-1,2,4-oxadiazol-5-yl)methyl)nicotinamide

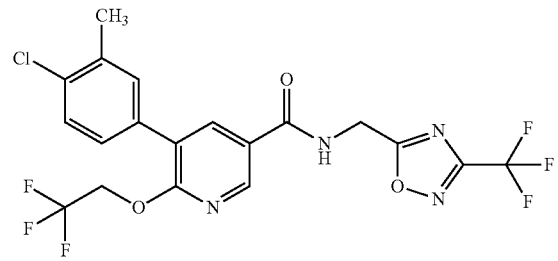 [SMILES: Cc1cc(-c2cc(C(=O)NCc3nc(C(F)(F)F)no3)cnc2OCC(F)(F)F)ccc1Cl]

The title compound was synthesized in analogy to Example 1 using 5-(4-chloro-3-methylphenyl)-6-(2,2,2-trifluoroethoxy)nicotinic acid (example BJ) and 3-trifluoromethyl-[1,2,4]oxadiazol-5-methanamine (example AK) as starting materials; LC-MS (UV peak area/ESI) 100%, 493.0523 (M+H)$^+$.

Example 73

Preparation of 4-(3-chloro-4-methylphenyl)-N-((3-methoxyisoxazol-5-yl)methyl)-5-(2,2,2-trifluoroethoxy)picolinamide

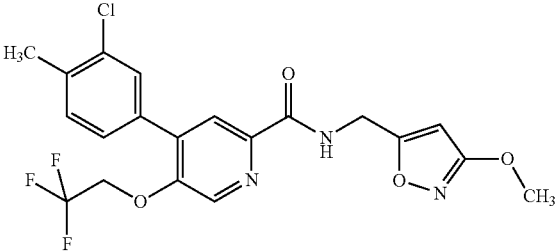

The title compound was synthesized in analogy to Example 1 using 4-(3-chloro-4-methylphenyl)-5-(2,2,2-trifluoroethoxy)picolinic acid (example BM) and 3-methoxy-5-isoxazolemethanamine (CAN 2763-94-2) as starting materials; LC-MS (UV peak area/ESI) 100%, 456.0934 (M+H)⁺.

Example 74

Preparation of 4-(4-chloro-3-methylphenyl)-N-((3-methoxyisoxazol-5-yl)methyl)-5-(2,2,2-trifluoroethoxy)picolinamide

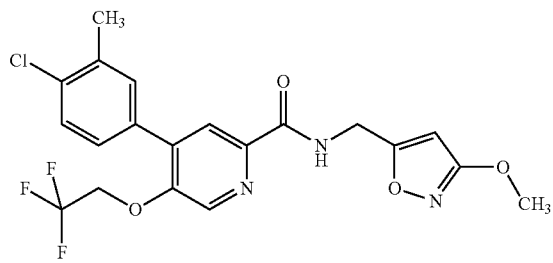 [SMILES: COc1cc(CNC(=O)c2cc(-c3ccc(Cl)c(C)c3)c(OCC(F)(F)F)cn2)on1]

The title compound was synthesized in analogy to Example 1 using 4-(4-chloro-3-methylphenyl)-5-(2,2,2-trifluoroethoxy)picolinic acid (example BN) and 3-methoxy-5-isoxazolemethanamine (CAN 2763-94-2) as starting materials; LC-MS (UV peak area/ESI) 100%, 456.0938 (M+H)⁺.

Example 75

Preparation of 4-(3,4-dimethylphenyl)-N-((3-methoxyisoxazol-5-yl)methyl)-5-(2,2,2-trifluoroethoxy)picolinamide

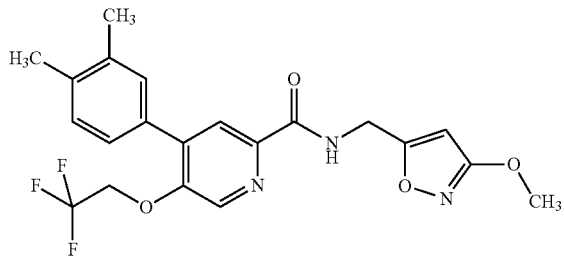

The title compound was synthesized in analogy to Example 1 using 4-(3,4-dimethylphenyl)-5-(2,2,2-trifluoroethoxy)picolinic acid (example BO) and 3-methoxy-5-isoxazolemethanamine (CAN 2763-94-2) as starting materials; LC-MS (UV peak area/ESI) 100%, 436.1476 (M+H)⁺.

Example 76

Preparation of 4-(4-chloro-3-methylphenyl)-N-((2-cyclopropylthiazol-4-yl)methyl)-5-(2,2,2-trifluoroethoxy)picolinamide

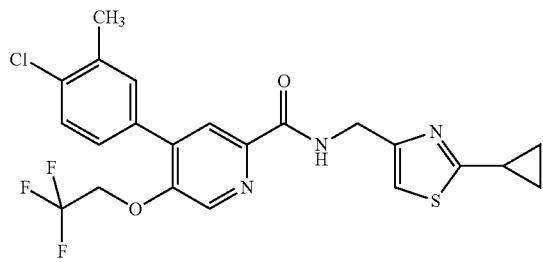 [SMILES: Cc1cc(-c2cc(C(=O)NCc3csc(C4CC4)n3)ncc2OCC(F)(F)F)ccc1Cl]

The title compound was synthesized in analogy to Example 1 using 4-(4-chloro-3-methylphenyl)-5-(2,2,2-trifluoroethoxy)picolinic acid (example BN) and 2-cyclopropyl-4-thiazolemethanamine (CAN 1083299-53-9) as starting materials; LC-MS (UV peak area/ESI) 100%, 482.0911 (M+H)⁺.

Example 77

Preparation of 4-(4-chloro-3-methylphenyl)-5-(2,2,2-trifluoroethoxy)-N-((3-(trifluoromethyl)-1,2,4-oxadiazol-5-yl)methyl)picolinamide

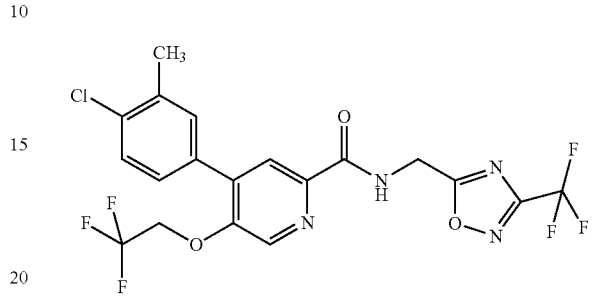

The title compound was synthesized in analogy to Example 1 using 4-(4-chloro-3-methylphenyl)-5-(2,2,2-trifluoroethoxy)picolinic acid (example BN) and 3-trifluoromethyl-[1,2,4]oxadiazol-5-methanamine (example AK) as starting materials; LC-MS (UV peak area/ESI) 100%, 493.0499 (M+H)⁺.

Example 78

Preparation of 4-(3,4-dimethylphenyl)-5-(2,2,2-trifluoroethoxy)-N-43-(trifluoromethyl)-1,2,4-oxadiazol-5-yl)methyl)picolinamide

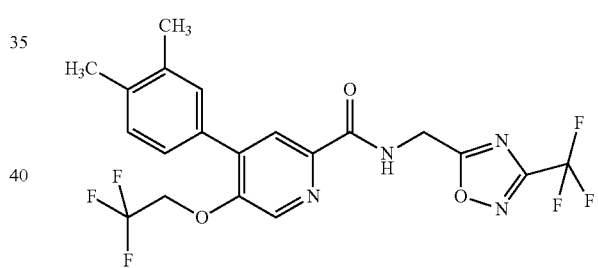

The title compound was synthesized in analogy to Example 1 using 4-(3,4-dimethyl-phenyl)-5-(2,2,2-trifluoroethoxy)picolinic acid (example BO) and 3-trifluoromethyl-[1,2,4]oxadiazol-5-methanamine (example AK) as starting materials; LC-MS (UV peak area/ESI) 100%, 475.1211 (M+H)⁺.

Example 79

Preparation of 5-p-tolyl-6-(2,2,2-trifluoroethoxy)-N-((3-(trifluoromethyl)-1,2,4-oxadiazol-5-yl)methyl)nicotinamide

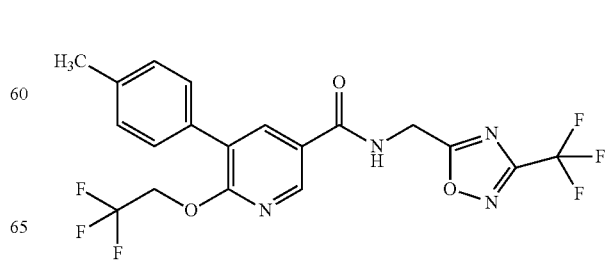

5-Bromo-6-(2,2,2-trifluoroethoxy)-N-((3-(trifluoromethyl)-1,2,4-oxadiazol-5-yl)methyl)nicotinamide (example BP; 100 mg, 223 µmol), p-tolylboronic acid (CAN 5720-05-8; 33 mg, 243 µmol), 1,1'-bis(diphenylphosphino)-ferrocenepalladium(II)dichloride dichloromethane complex (4 mg, 5.27 µmol) and Na$_2$CO$_3$ (35 mg, 330 µmol) were combined with tetrahydrofuran (5 mL) and water (1.5 mL). The reaction mixture was heated to 90° C., stirred for 15 h, cooled down and poured into 25 mL H$_2$O. The mixture was extracted with ethyl acetate (2×25 mL). The organic layers were combined, washed with brine (1×25 mL), dried with MgSO$_4$ and concentrated in vacuo. The crude material was purified twice by flash chromatography (silica gel, 20 g, 0% to 40% ethyl acetate in hexanes) to give 48 mg (46%) of the title compound as a light yellow solid; MS (ESI): 459.090 (M−H)$^-$.

Example 80

Preparation of 5-(3-chloro-4-methylphenyl)-6-(2,2,2-trifluoroethoxy)-N-((3-(trifluoromethyl)-1,2,4-oxadiazol-5-yl)methyl)nicotinamide

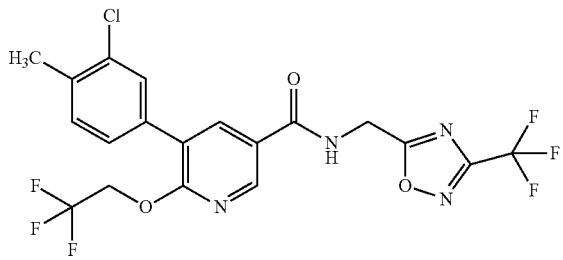 [SMILES: Cc1ccc(-c2cc(C(=O)NCc3nc(C(F)(F)F)no3)cnc2OCC(F)(F)F)cc1Cl]

The title compound was synthesized in analogy to Example 83 using 5-bromo-6-(2,2,2-trifluoroethoxy)-N-((3-(trifluoromethyl)-1,2,4-oxadiazol-5-yl)methyl)nicotinamide (example BP) and B-(3-chloro-4-methylphenyl)-boronic acid, (CAN 175883-63-3) as starting materials; LC-MS (UV peak area/ESI) 100%, 493.0516 (M+H)$^+$.

Example 81

Preparation of 5-(3-chloro-4-fluorophenyl)-6-(2,2,2-trifluoroethoxy)-N-((3-(trifluoromethyl)-1,2,4-oxadiazol-5-yl)methyl)nicotinamide

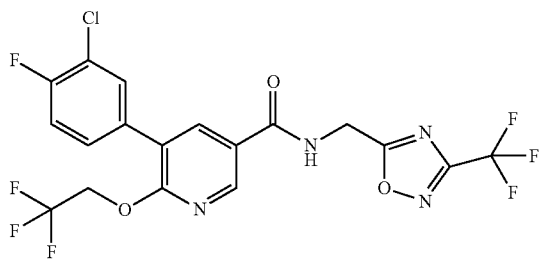 [SMILES: O=C(NCc1nc(C(F)(F)F)no1)c1cnc(OCC(F)(F)F)c(-c2ccc(F)c(Cl)c2)c1]

The title compound was synthesized in analogy to Example 1 using 5-(3-chloro-4-fluorophenyl)-6-(2,2,2-trifluoroethoxy)nicotinic acid (example BQ) and 3-trifluoromethyl-[1,2,4]oxadiazol-5-methanamine (example AK) as starting materials; LC-MS (UV peak area/ESI) 97.1%, 497.0259 (M−H)$^-$.

Example 82

Preparation of 5-(4-chloro-3-fluorophenyl)-6-(2,2,2-trifluoroethoxy)-N-((3-(trifluoromethyl)-1,2,4-oxadiazol-5-yl)methyl)nicotinamide

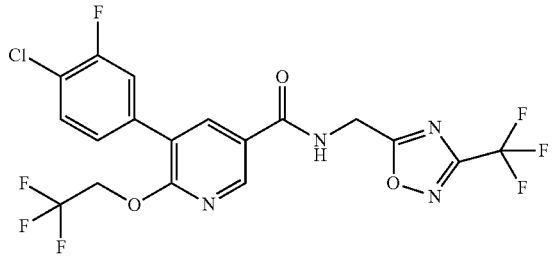 [SMILES: O=C(NCc1nc(C(F)(F)F)no1)c1cnc(OCC(F)(F)F)c(-c2ccc(Cl)c(F)c2)c1]

The title compound was synthesized in analogy to Example 1 using 5-(4-chloro-3-fluorophenyl)-6-(2,2,2-trifluoroethoxy)nicotinic acid (example BR) and 3-trifluoromethyl-[1,2,4]oxadiazol-5-methanamine (example AK) as starting materials; LC-MS (UV peak area/ESI) 98.8%, 497.0260 (M+H)$^+$.

Example 83

Preparation of 5-(4-ethylphenyl)-6-(2,2,2-trifluoroethoxy)-N-((3-(trifluoromethyl)-1,2,4-oxadiazol-5-yl)methyl)nicotinamide

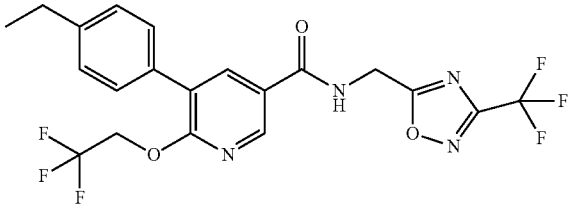 [SMILES: CCc1ccc(-c2cc(C(=O)NCc3nc(C(F)(F)F)no3)cnc2OCC(F)(F)F)cc1]

The title compound was synthesized in analogy to Example 1 using 5-(4-ethylphenyl)-6-(2,2,2-trifluoroethoxy)nicotinic acid (example BS) and 3-trifluoromethyl-[1,2,4]oxadiazol-5-methanamine (example AK) as starting materials; LC-MS (UV peak area/ESI) 100%, 473.1054 (M−H)$^-$.

Example 84

Preparation of 5-(4-chloro-2-fluorophenyl)-6-(2,2,2-trifluoroethoxy)-N-((3-(trifluoromethyl)-1,2,4-oxadiazol-5-yl)methyl)nicotinamide

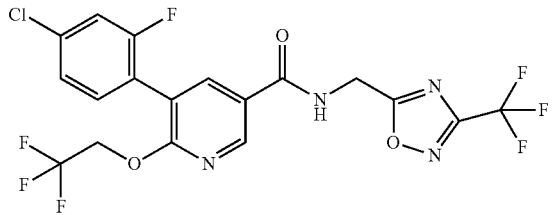 [SMILES: O=C(NCc1nc(C(F)(F)F)no1)c1cnc(OCC(F)(F)F)c(-c2ccc(Cl)cc2F)c1]

The title compound was synthesized in analogy to Example 1 using 5-(4-chloro-2-fluorophenyl)-6-(2,2,2-trifluoroethoxy)nicotinic acid (example BT) and 3-trifluoromethyl-[1,2,4]oxadiazol-5-methanamine (example AK) as starting materials; LC-MS (UV peak area/ESI) 98.6%, 497.0254 (M−H)$^-$.

Example 85

Preparation of 5-(2,3-dihydro-1H-inden-5-yl)-6-(2,2,2-trifluoroethoxy)-N-((3-(trifluoromethyl)-1,2,4-oxadiazol-5-yl)methyl)nicotinamide

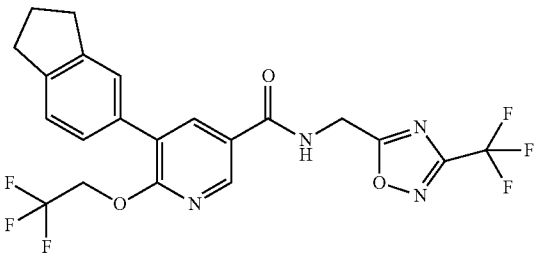 [SMILES: O=C(NCc1nc(C(F)(F)F)no1)c1cnc(OCC(F)(F)F)c(-c2ccc3c(c2)CCC3)c1]

The title compound was synthesized in analogy to Example 83 using 5-bromo-6-(2,2,2-trifluoroethoxy)-N-((3-(trifluoromethyl)-1,2,4-oxadiazol-5-yl)methyl)nicotinamide (example BP) and B-(2,3-dihydro-1H-inden-5-yl)-boronic acid (CAN 196861-31-1) as starting materials; LC-MS (UV peak area/ESI) 100%, 485.1016 (M−H)⁻.

Example 86

Preparation of 5-(4-chloro-3-fluorophenyl)-N-((3-methoxyisoxazol-5-yl)methyl)-6-(2,2,2-trifluoroethoxy)nicotinamide

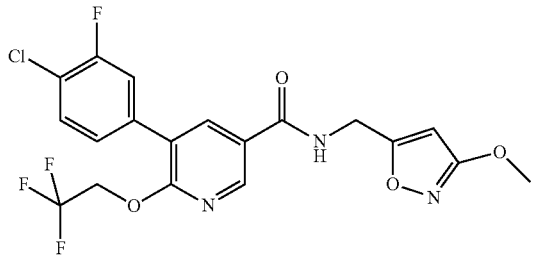 [SMILES: COc1cc(CNC(=O)c2cnc(OCC(F)(F)F)c(-c3ccc(Cl)c(F)c3)c2)on1]

The title compound was synthesized in analogy to Example 1 using 5-(4-chloro-3-fluorophenyl)-6-(2,2,2-trifluoroethoxy)nicotinic acid (example BR) and 3-methoxy-5-isoxazolemethanamine (CAN 2763-94-2) as starting materials; LC-MS (UV peak area/ESI) 100%, 458.0537 (M−H)⁻.

Example 87

Preparation of 5-(4-cyanophenyl)-6-(2,2,2-trifluoroethoxy)-N-((3-(trifluoromethyl)-1,2,4-oxadiazol-5-yl)methyl)nicotinamide

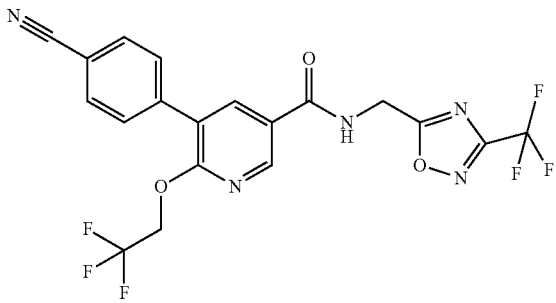 [SMILES: N#Cc1ccc(-c2cc(C(=O)NCc3nc(C(F)(F)F)no3)cnc2OCC(F)(F)F)cc1]

The title compound was synthesized in analogy to Example 1 using 5-(4-cyanophenyl)-6-(2,2,2-trifluoroethoxy)nicotinic acid (example BU) and 3-trifluoromethyl-[1,2,4]oxadiazole-5-methanamine (example AK) as starting materials; MS (ESI): 470.2 (M−H)⁻.

Example 88

Preparation of 5-(4-chlorophenyl)-N-((1-(cyclopropylmethyl)-1H-pyrazol-3-yl)methyl)-6-(2,2,2-trifluoroethoxy)nicotinamide

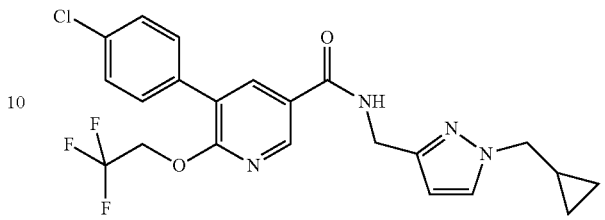

The title compound was synthesized in analogy to Example 1 using 5-(4-chloro-phenyl)-6-(2,2,2-trifluoroethoxy)-nicotinic acid (CAN 1018782-82-5) and (1-(cyclopropylmethyl)-1H-pyrazol-3-yl)methanamine (example BW) as starting materials, MS (EI) 465.3 (M+H)⁺.

Example 89

Preparation of 5-(3,4-difluorophenyl)-6-(2,2,2-trifluoroethoxy)-N-((3-(trifluoromethyl)-1,2,4-oxadiazol-5-yl)methyl)nicotinamide

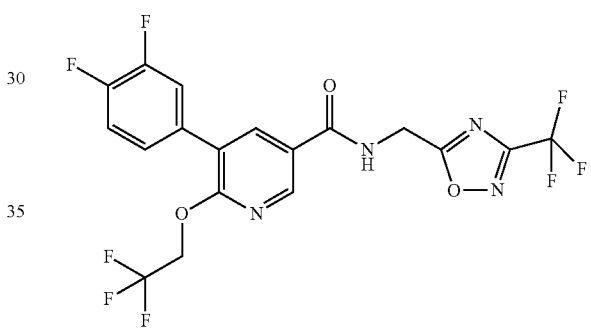

The title compound was synthesized in analogy to Example 1 using 5-(3,4-difluorophenyl)-6-(2,2,2-trifluoroethoxy)nicotinic acid (example BX) and 3-trifluoromethyl-[1,2,4]oxadiazol-5-methanamine (example AK) as starting materials; MS (ESI): 483.2 (M+H)⁺.

Example 90

Preparation of 5-(4-chlorophenyl)-N-((3-methyl-1,2,4-oxadiazol-5-yl)methyl)-6-(2,2,2-trifluoroethoxy)nicotinamide

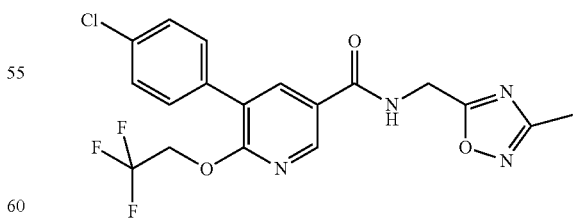

The title compound was synthesized in analogy to Example 1 using 5-(4-chloro-phenyl)-6-(2,2,2-trifluoroethoxy)-nicotinic acid (CAN 1018782-82-5) and 3-methyl-1,2,4-oxadiazole-5-methanamine (CAN 90928-92-0) as starting materials; LC-MS (UV peak area/ESI) 100%, 425.0644 (M−H)⁻.

Example 91

Preparation of 6-cyclobutoxy-5-(3,4-difluorophenyl)-N-((3-(trifluoromethyl)-1,2,4-oxadiazol-5-yl)methyl)nicotinamide

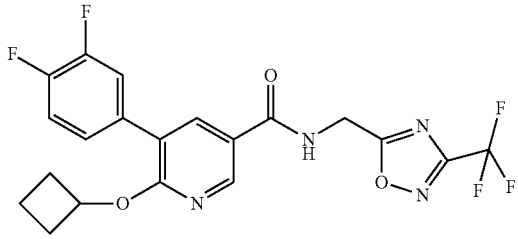 [SMILES: O=C(NCc1nc(C(F)(F)F)no1)c1cnc(OC2CCC2)c(-c2ccc(F)c(F)c2)c1]

The title compound was synthesized in analogy to Example 1 using 6-cyclobutoxy-5-(3,4-difluorophenyl)nicotinic acid (example BZ) and 3-trifluoromethyl-[1,2,4]oxadiazol-5-methanamine (example AK) as starting materials; LC-MS (UV peak area/ESI) 98.0%, 455.1 (M+H)+.

Example 92

Preparation of 5-(4-chlorophenyl)-6-cyclobutoxy-N-((3-(trifluoromethyl)-1,2,4-oxadiazol-5-yl)methyl)nicotinamide

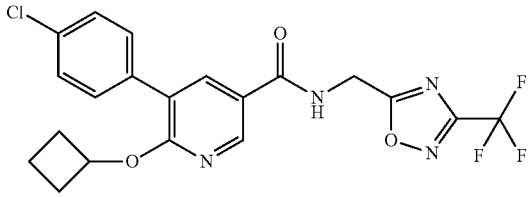 [SMILES: O=C(NCc1nc(C(F)(F)F)no1)c1cnc(OC2CCC2)c(-c2ccc(Cl)cc2)c1]

The title compound was synthesized in analogy to Example 1 using 5-(4-chlorophenyl)-6-cyclobutoxy-nicotinic acid (example CA) and 3-trifluoromethyl-[1,2,4]oxadiazol-5-methanamine (example AK) as starting materials; LC-MS (UV peak area/ESI) 92.8%, 451.1 (M−H)−.

Example 93

Preparation of 5-(4-chloro-3-fluorophenyl)-6-cyclobutoxy-N-((3-(trifluoromethyl)-1,2,4-oxadiazol-5-yl)methyl)nicotinamide

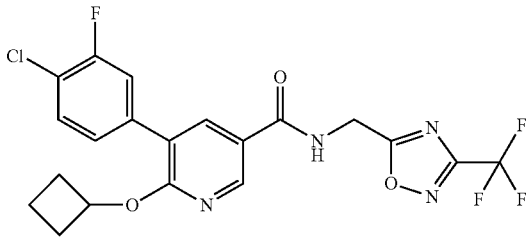 [SMILES: O=C(NCc1nc(C(F)(F)F)no1)c1cnc(OC2CCC2)c(-c2ccc(Cl)c(F)c2)c1]

The title compound was synthesized in analogy to Example 1 using 5-(4-chloro-3-fluorophenyl)-6-cyclobutoxy-nicotinic acid (example CB) and 3-trifluoromethyl-[1,2,4]oxadiazol-5-methanamine (example AK) as starting materials; LC-MS (UV peak area/ESI) 90.1%, 471.1 (M+H)+.

Example 94

Preparation of 5-(4-chloro-3-methylphenyl)-6-cyclobutoxy-N-((3-(trifluoromethyl)-1,2,4-oxadiazol-5-yl)methyl)nicotinamide

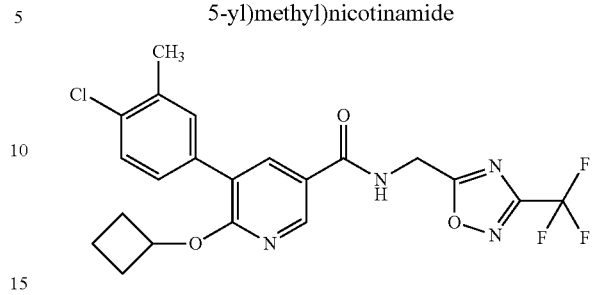

The title compound was synthesized in analogy to Example 1 using 5-(4-chloro-3-methylphenyl)-6-cyclobutoxy-nicotinic acid (example CC) and 3-trifluoromethyl-[1,2,4]oxadiazol-5-methanamine (example AK) as starting materials; LC-MS (UV peak area/ESI) 93.8%, 467.1 (M+H)+.

Example 95

Preparation of 6-(cyclopropylmethoxy)-5-(3,4-difluorophenyl)-N-((3-(trifluoromethyl)-1,2,4-oxadiazol-5-yl)methyl)nicotinamide

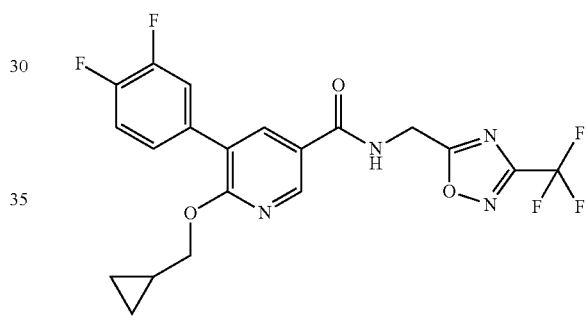

The title compound was synthesized in analogy to Example 1 using 6-(cyclopropylmethoxy)-5-(3,4-difluorophenyl)-nicotinic acid (example CD) and 3-trifluoromethyl-[1,2,4]oxadiazol-5-methanamine (example AK) as starting materials; LC-MS (UV peak area/ESI) 100.0%, 455.1 (M+H)+.

Example 96

Preparation of 5-(3,4-difluorophenyl)-6-(2-methoxyethoxy)-N-((3-(trifluoromethyl)-1,2,4-oxadiazol-5-yl)methyl)nicotinamide

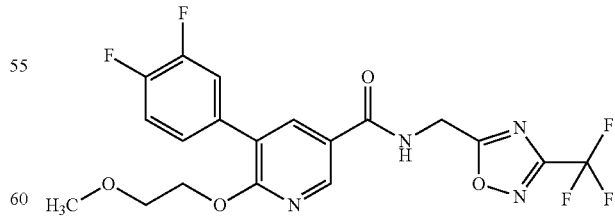

The title compound was synthesized in analogy to Example 1 using 5-(3,4-difluorophenyl)-6-(2-methoxyethoxy)-nicotinic acid (example CE) and 3-trifluoromethyl-[1,2,4]oxadiazol-5-methanamine (example AK) as starting materials; LC-MS (UV peak area/ESI) 87.6%, 459.1 (M+H)+.

Example 97

Preparation of 5-(4-chloro-3-fluorophenyl)-6-(2-methoxyethoxy)-N-((3-(trifluoromethyl)-1,2,4-oxadiazol-5-yl)methyl)nicotinamide

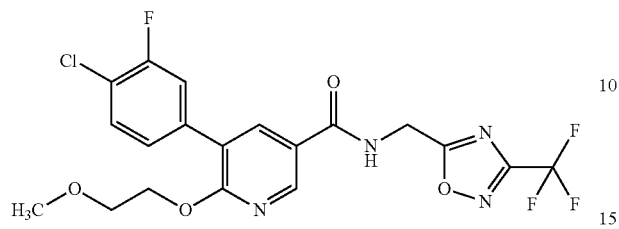

The title compound was synthesized in analogy to Example 1 using 5-(4-chloro-3-fluorophenyl)-6-(2-methoxyethoxy)-nicotinic acid (example CF) and 3-trifluoromethyl-[1,2,4]oxadiazol-5-methanamine (example AK) as starting materials; LC-MS (UV peak area/ESI) 100%, 473.0662 (M−H)−.

Example 98

Preparation of 5-(4-chloro-3-methylphenyl)-6-(2-methoxyethoxy)-N-((3-(trifluoromethyl)-1,2,4-oxadiazol-5-yl)methyl)nicotinamide

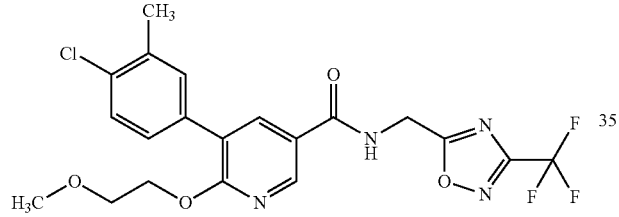

The title compound was synthesized in analogy to Example 1 using 5-(4-chloro-3-methylphenyl)-6-(2-methoxyethoxy)nicotinic acid (example CG) and 3-trifluoromethyl-[1,2,4]oxadiazol-5-methanamine (example AK) as starting materials; LC-MS (UV peak area/ESI) 100%, 469.0893 (M−H)−.

Example 99

Preparation of 5-(3,4-difluorophenyl)-N-((3-methoxyisoxazol-5-yl)methyl)-6-(2,2,2-trifluoroethoxy)nicotinamide

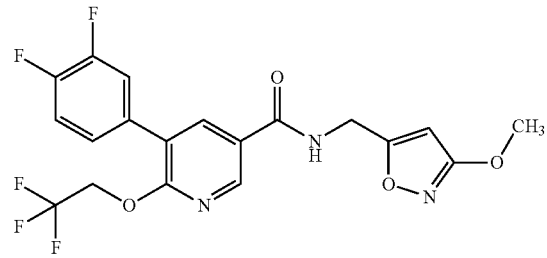 [SMILES: COc1cc(CNC(=O)c2cnc(OCC(F)(F)F)c(-c3ccc(F)c(F)c3)c2)on1]

The title compound was synthesized in analogy to Example 1 using 5-(3,4-difluorophenyl)-6-(2,2,2-trifluoroethoxy)nicotinic acid (example BX) and 3-methoxy-5-isoxazolemethanamine (CAN 2763-94-2) as starting materials; LC-MS (UV peak area/ESI) 84%, 407.9815 (M+H)+.

Example 100

Preparation of 5-Benzo[1,2,5]oxadiazol-5-yl-6-(2,2,2-trifluoro-ethoxy)-N-(3-trifluoromethyl-[1,2,4]oxadiazol-5-yl-methyl)-nicotinamide

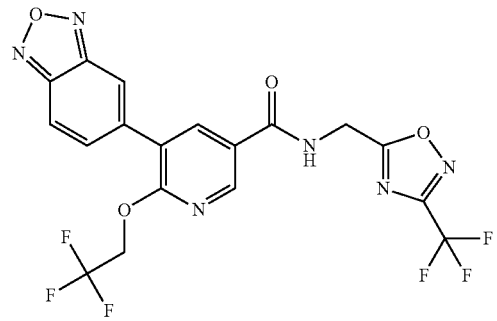 [SMILES: O=C(NCc1nc(C(F)(F)F)no1)c1cnc(OCC(F)(F)F)c(-c2ccc3nonc3c2)c1]

The title compound was synthesized in analogy to Example 1 using 5-benzo[1,2,5]oxadiazol-5-yl-6-(2,2,2-trifluoro-ethoxy)-nicotinic acid (example CH) and 3-trifluoromethyl-[1,2,4]oxadiazol-5-methanamine (example AK) as starting materials; MS (ESI) 489.2 (M+H)+.

Example 101

Preparation of 5-(4-chlorophenyl)-6-cyclobutoxy-N-(pyridin-2-ylmethyl)nicotinamide

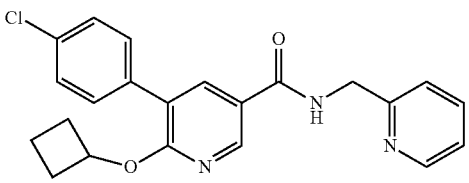 [SMILES: O=C(NCc1ccccn1)c1cnc(OC2CCC2)c(-c2ccc(Cl)cc2)c1]

The title compound was synthesized in analogy to Example 1 using 5-(4-chlorophenyl)-6-cyclobutoxy-nicotinic acid (example CA) and 2-pyridinemethanamine (CAN 3731-51-9) as starting materials; LC-MS (UV peak area/ESI) 99.0%, 394.1 (M+H)+.

Example 102

Preparation of 5-(4-chlorophenyl)-6-(2-hydroxyethoxy)-N-((3-(trifluoromethyl)-1,2,4-oxadiazol-5-yl)methyl)nicotinamide

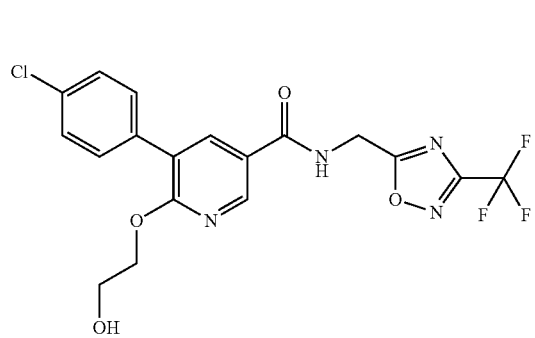 [SMILES: O=C(NCc1nc(C(F)(F)F)no1)c1cnc(OCCO)c(-c2ccc(Cl)cc2)c1]

The title compound was synthesized in analogy to Example 1 using 5-(4-chlorophenyl)-6-(2-hydroxyethoxy)nicotinic acid (example CI) and 3-trifluoromethyl-[1,2,4]oxadiazol-5-methanamine (example AK) as starting materials; LC-MS (UV peak area/ESI) 100.0%, 443.1 (M+H)+.

Example 103

Preparation of (R)-5-(4-chlorophenyl)-6-(tetrahydro-furan-3-yloxy)-N-((3-(trifluoromethyl)-1,2,4-oxadiazol-5-yl)methyl)nicotinamide

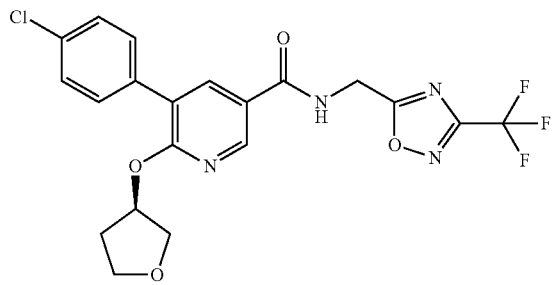 [SMILES: O=C(NCc1nc(C(F)(F)F)no1)c1cnc(O[C@@H]2CCOC2)c(-c2ccc(Cl)cc2)c1]

The title compound was synthesized in analogy to Example 1 using (R)-5-(4-chlorophenyl)-6-(tetrahydrofuran-3-yloxy)nicotinic acid (example CJ) and 3-trifluoromethyl-[1,2,4]oxadiazol-5-methanamine (example AK) as starting materials; LC-MS (UV peak area/ESI) 94.6%, 469.1 (M+H)+.

Example 104

Preparation of (SR)-5-(4-chlorophenyl)-6-((tetrahydrofuran-3-yl)methoxy)-N-((3-(trifluoromethyl)-1,2,4-oxadiazol-5-yl)methyl)nicotinamide

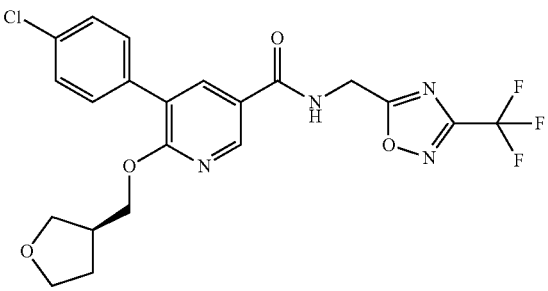 [SMILES: O=C(NCc1nc(C(F)(F)F)no1)c1cnc(OC[C@H]2CCOC2)c(-c2ccc(Cl)cc2)c1]

The title compound was synthesized in analogy to Example 1 using 5-(4-chloro-phenyl)-6-(tetrahydro-furan-3-ylmethoxy)-nicotinic acid (example CK) and 3-trifluoromethyl-[1,2,4]oxadiazol-5-methanamine (example AK) as starting materials; enantiomers were separated by chiral HPLC (ChiralPak AD, 30% ethanol/n-heptane (−) enantiomer isolated; LC-MS (UV peak area/ESI) 100%, 483.1038 (M+H)+; $\alpha_D^{20}$(MeOH)=−12.2°

Example 105

Preparation of 5-(4-Chloro-phenyl)-6-[(RS)-1-(tetrahydro-furan-3-yl)methoxy]-N-(3-trifluoromethyl-[1,2,4]oxadiazol-5-ylmethyl)-nicotinamide

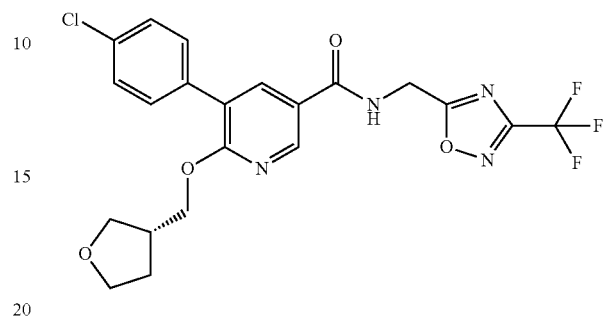

The title compound was synthesized in analogy to Example 1 using 5-(4-chloro-phenyl)-6-(tetrahydro-furan-3-ylmethoxy)-nicotinic acid (example CK) and 3-trifluoromethyl-[1,2,4]oxadiazol-5-methanamine (example AK) as starting materials; enantiomers were separated by chiral HPLC (ChiralPak AD, 30% ethanol/n-heptane (+) enantiomer isolated; LC-MS (UV peak area/ESI) 100%, 483.1038 (M+H)+.

$\alpha_D^{20}$(MeOH)=+13.2°

The invention claimed is:
1. A compound of formula I,

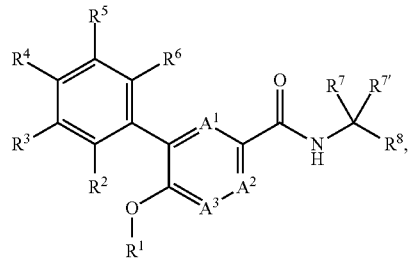

I wherein
$A^1$ and $A^3$ are CH and $A^2$ is N;
$R^1$ is selected from the group consisting of lower alkyl,
cycloalkyl,
lower cycloalkylalkyl,
lower hydroxyalkyl,
lower alkoxyalkyl,
lower halogenalkyl,
lower carbamoylalkyl,
lower alkylcarbonylaminoalkyl,
lower phenylalkyl,
lower heterocyclylalkyl wherein the heterocyclyl group is unsubstituted or substituted by oxo,
lower heteroarylalkyl wherein the heteroaryl group is unsubstituted or mono- or di-substituted by lower alkyl, and
phenyl which is unsubstituted or mono- or di-substituted by halogen;

$R^2$ and $R^6$ independently from each other are hydrogen or halogen;

$R^3$ and $R^5$ independently from each other are selected from the group consisting of hydrogen, lower alkyl, lower alkoxy, halogen, lower halogenalkyl, lower halogenalkoxy and cyano;

$R^4$ is selected from the group consisting of hydrogen, lower alkoxy, halogen, lower halogenalkyl, lower halogenalkoxy and cyano;

$R^7$ and $R^{7'}$ independently from each other are hydrogen or lower alkyl; and $R^8$ is a five-membered heteroaryl group containing one, two or three heteroatoms selected from the group consisting of N, O and S, said heteroaryl group being unsubstituted or substituted by one or two substituents independently selected from the group consisting of lower alkyl, lower alkoxy, halogen, lower halogenalkyl and cycloalkyl;

or a pharmaceutically acceptable salt thereof.

2. A compound according to claim 1, wherein $R^1$ is lower cycloalkylalkyl or lower halogenalkyl.

3. A compound according to claim 1, wherein $R^2$ and $R^6$ are hydrogen.

4. A compound according to claim 1, wherein $R^3$ and $R^5$ are hydrogen.

5. A compound according to claim 1, wherein $R^4$ is halogen.

6. A compound according to claim 1, wherein $R^7$ and $R^{7'}$ are hydrogen.

7. A compound according to claim 1, wherein the five-membered heteroaryl group is selected from the group consisting of oxazolyl, isoxazolyl, pyrazolyl, thiazolyl and [1,2,4]oxadiazolyl, said heteroaryl group being unsubstituted or substituted by one or two substituents independently selected from the group consisting of lower alkyl, lower alkoxy, halogen, lower halogenalkyl and cycloalkyl.

8. A compound according to claim 1, selected from the group consisting of:

4-(4-chloro-phenyl)-5-(2,2,2-trifluoro-ethoxy)-pyridine-2-carboxylic acid (3-methoxy-isoxazol-5-ylmethyl)-amide, 4-(4-chloro-phenyl)-5-(2,2,2-trifluoro-ethoxy)-pyridine-2-carboxylic acid (3-isopropyl-isoxazol-5-ylmethyl)-amide, 4-(4-chloro-phenyl)-5-(2,2,2-trifluoro-ethoxy)-pyridine-2-carboxylic acid (3-ethyl-isoxazol-5-ylmethyl)-amide, 4-(4-chloro-phenyl)-5-(2,2,2-trifluoro-ethoxy)-pyridine-2-carboxylic acid (1-propyl-1H-1-pyrazol-3-ylmethyl)-amide, 4-(4-chloro-phenyl)-5-(2,2,2-trifluoro-ethoxy)-pyridine-2-carboxylic acid (2-isopropyl-thiazol-4-ylmethyl)-amide, and pharmaceutically acceptable salts thereof.

9. A pharmaceutical composition comprising a compound according to claim 1 and a pharmaceutically acceptable carrier and/or adjuvant.

* * * * *